(12) United States Patent
Wang et al.

(10) Patent No.: US 12,343,331 B2
(45) Date of Patent: Jul. 1, 2025

(54) METHODS AND AGENTS THAT STIMULATE MITOCHONDRIAL TURNOVER FOR TREATING DISEASE

(71) Applicant: Capacity Bio, Inc., Palo Alto, CA (US)

(72) Inventors: Amy E. Wang, Santa Monica, CA (US); Alejandro Martorell-Riera, Walnut, CA (US); Kevin John Gaffney, Chicago, IL (US)

(73) Assignee: Capacity Bio, Inc., Palo Alto, CA (US)

( * ) Notice: Subject to any disclaimer, the term of this patent is extended or adjusted under 35 U.S.C. 154(b) by 0 days.

(21) Appl. No.: 17/587,565

(22) Filed: Jan. 28, 2022

(65) Prior Publication Data

US 2022/0233507 A1 Jul. 28, 2022

Related U.S. Application Data

(60) Provisional application No. 63/142,683, filed on Jan. 28, 2021.

(51) Int. Cl.
*A61K 31/4178* (2006.01)
*A61K 31/56* (2006.01)
*A61K 45/06* (2006.01)

(52) U.S. Cl.
CPC .......... *A61K 31/4178* (2013.01); *A61K 31/56* (2013.01); *A61K 45/06* (2013.01)

(58) Field of Classification Search
CPC ..... A61K 31/4178; A61K 31/56; A61K 45/06
See application file for complete search history.

(56) References Cited

U.S. PATENT DOCUMENTS

| | | | |
|---|---|---|---|
| 9,732,074 B2 | 8/2017 | Petasis et al. | |
| 9,943,509 B2 * | 4/2018 | Gaffney | A61K 31/4439 |
| 10,301,298 B2 | 5/2019 | Petasis et al. | |
| 11,446,285 B2 | 9/2022 | Gaffney et al. | |
| 2011/0281805 A1 | 11/2011 | Walther et al. | |
| 2016/0296591 A1 | 10/2016 | Franklin | |
| 2017/0119748 A1 * | 5/2017 | Gaffney | A61K 31/4439 |
| 2018/0030042 A1 | 2/2018 | Petasis et al. | |
| 2019/0351009 A1 | 11/2019 | Hay et al. | |
| 2020/0215037 A1 | 7/2020 | Gaffney et al. | |
| 2021/0283128 A1 | 9/2021 | Jadhav et al. | |

FOREIGN PATENT DOCUMENTS

| | | | | |
|---|---|---|---|---|
| WO | WO 2015/054005 A1 * | 4/2015 | | A61P 25/00 |
| WO | WO 2019/027890 A1 | 2/2019 | | |
| WO | WO 2019/036267 A1 * | 2/2019 | | A61K 31/4427 |

OTHER PUBLICATIONS

Garrett R. Ainslie, K. Michael Gibson, Kara R. Vogel, Chapter 9—mTOR, Autophagy, Aminoacidopathies, and Human Genetic Disorders, Molecules to Medicine with mTOR, Academic Press, 2016, Chapter 9, Section 7.3, ISBN 9780128027332 (Year: 2016).*
Price, Nathan L. et al. SIRT1 is required for AMPK activation and the beneficial effects of resveratrol on mitochondrial function. Cell Metab. May 2, 2012;15(5):675-90 (Year: 2012).*
Liu Y, Wang J, Luo S, Zhan Y, Lu Q. The roles of PPARγ and its agonists in autoimmune diseases: A comprehensive review. J Autoimmun. Sep. 2020;113:102510. (Year: 2020).*
Santos, R.A.S. and Ferreira, A.J. (2006), Pharmacological Effects of AVE 0991, a Nonpeptide Angiotensin-(1-7) Receptor Agonist. Cardiovascular Drug Reviews, 24: 239-246 (Year: 2006).*
Zhang QS, Deater M, Schubert K, Marquez-Loza L, Pelz C, Sinclair DA, Grompe M. The Sirt1 activator SRT3025 expands hematopoietic stem and progenitor cells and improves hematopoiesis in Fanconi anemia mice. Stem Cell Res. Jul. 2015;15(1):130-40 (Year: 2015).*
Fanconi Anemia; www.hoacny.com/patient-resources/blood-disorders/fanconi-anemia; archived via Wayback Machine on Apr. 2, 2018. (Year: 2018).*
Tang X, Drotar J, Li K, Clairmont CD, Brumm AS, Sullins AJ, Wu H, Liu XS, Wang J, Gray NS, Sur M, Jaenisch R. Pharmacological enhancement of KCC2 gene expression exerts therapeutic effects on human Rett syndrome neurons and Mecp2 mutant mice. Sci Transl Med., 2019, 11(503):eaau0164 (Year: 2019).*
International Search Report & Written Opinion dated May 3, 2022 for PCT/US2022/014330. 17 pages.
Hay, et al. A novel angiotensin-(1-7) glycosylated mas receptor agonist for treating vascular cognitive impairment and inflammation-related memory dysfunction. Journal of Pharmacology and Experimental Therapeutics Apr. 2019, 369 (1) 9-25.
International Preliminary Report on Patentability dated Aug. 10, 2023 for PCT/US2022/014330. 10 pages.
Partial Supplementary European Search Report dated Nov. 12, 2024 for European Application No. 22746702.4. 20 pages.
Nakanishi, et al. Effect of enalapril on 24-hour blood pressure in patents with essential hypertension. Current Therapeutic Research, Excerpta Medica, Trenton, NJ. Sep. 1, 1992; 52(3):361-367.

* cited by examiner

*Primary Examiner* — Alicia L Otton
*Assistant Examiner* — David M Shim
(74) *Attorney, Agent, or Firm* — Sheppard Mullin Richter & Hampton LLP

(57) ABSTRACT

Provided herein are methods of stimulating mitophagy in a subject in need thereof administering to the subject a mitophagy-stimulating amount of a MAS receptor agonist or substance that triggers endogenous production of a MAS receptor agonist. The present disclosure also relates to medical intervention methods and agents, namely methods and agents for stimulation of mitochondrial turnover for treatment of disease in a mammal. The disclosure comprises a method of stimulating increased mitochondrial turnover in a mammal comprising administering to the mammal a pharmacologically suitable dose of a MAS receptor agonist; MAS receptor modulator; a substance that triggers endogenous production of a MAS receptor agonist; a substance that triggers endogenous production of a MAS receptor modulator; or any combination thereof. The pharmacological activity acting on MAS receptor in turn stimulates an increase in mitochondrial turnover in host cells, alleviating a disease state in the host mammalian organism.

4 Claims, 26 Drawing Sheets

DMSO

A(1-7) 5nM

Nle$^3$-A(1-7) 5nM

Compound 7 5nM

A(1-7) 50nM

Nle³-A(1-7) 50nM

Compound 7 50nM

A(1-7) 500nM

Nle³-A(1-7) 500nM

Compound 7 500nM

A(1-7) 5µM

Nle³-A(1-7) 5µM

Compound 7 5µM

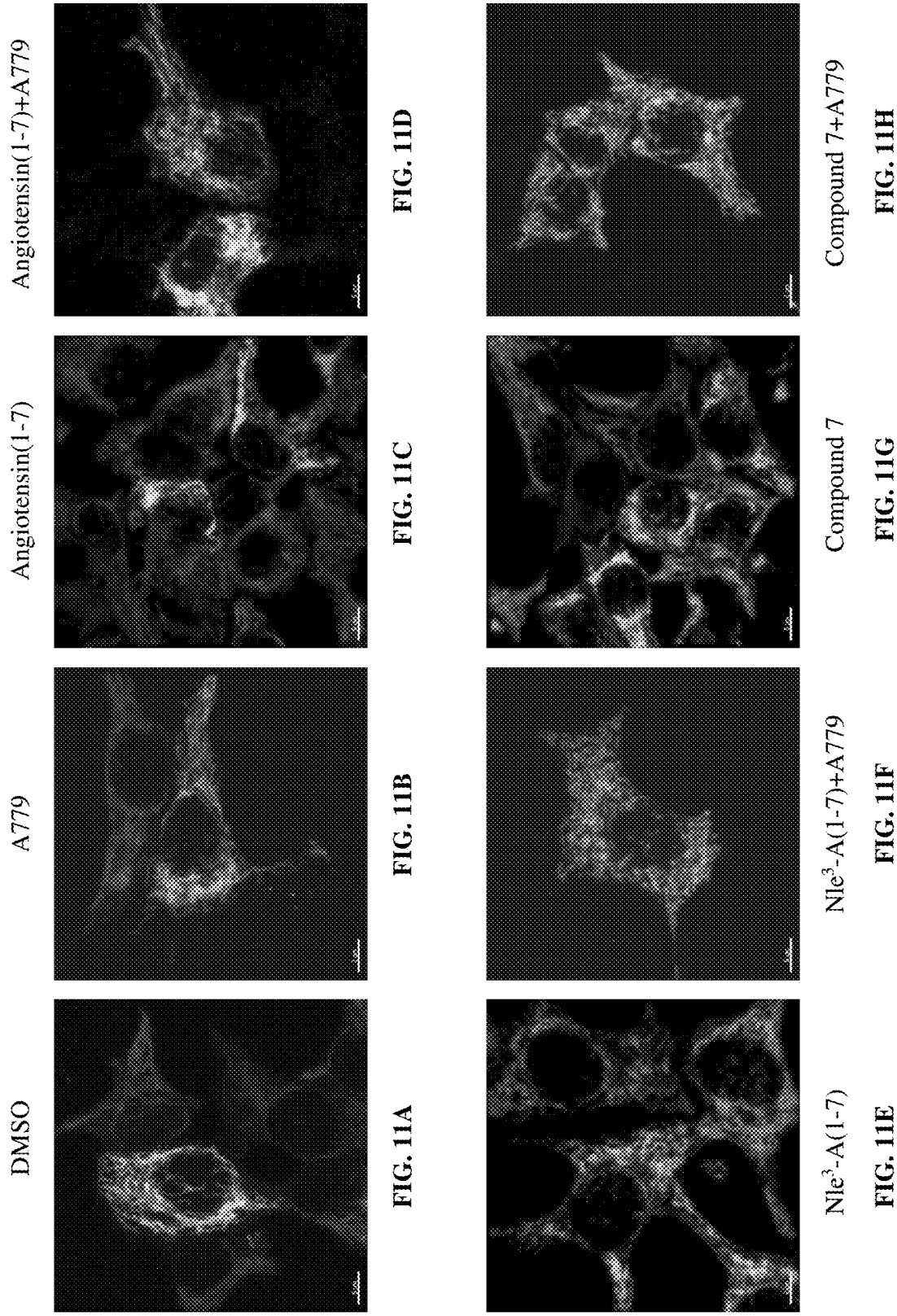

| Compounds | Concentration | Morphology | | |
|---|---|---|---|---|
| | | 8h | 24h | 72h |
| A(1-7) | 50 nM | Elongated mitochondria | Elongated mitochondria | Elongated mitochondria |
| Nle$^3$-A(1-7) | 50 nM | Elongated mitochondria | Elongated mitochondria | Elongated mitochondria |
| Compound 7 | 50 nM | Elongated mitochondria | Elongated mitochondria | Elongated mitochondria |

FIG. 12

METHODS AND AGENTS THAT STIMULATE MITOCHONDRIAL TURNOVER FOR TREATING DISEASE

CROSS-REFERENCE TO RELATED APPLICATIONS

This application claims the benefit under 35 U.S.C. § 119(e) of U.S. Provisional Application No. 63/142,683, filed Jan. 28, 2021, which is hereby incorporated by reference in its entirety.

FIELD

The present disclosure relates to medical intervention methods and agents, namely methods and agents for stimulation of mitochondrial turnover for treatment of disease in a mammal.

INCORPORATION BY REFERENCE

The following documents are incorporated by reference in their entireties herein: Bakula & Scheibye-Knudsen, FRONT. CELL. DEV. BIOL. 2020, 8: 239; Bose & Beal, J. NEUROCHEM., 2016 Oct. 139 Suppl.( ) 216-231; Joshi & Kundu, AUTOPHAGY 2013 Nov. 1 9(11) 1737-49, Killackey et al., J. CELL BIOL., 2020, 219:11; Morciano et al., J CLIN. MED., 2020 March; 9(3): 892; Morgia et al., J. INT. MED. 2020, 287; 592-608.; U.S. Pat. Nos. 6,235,766; 6,538,144; 9,943,509 B2; U.S. Pat. No. 10,301,298 B2; U.S. 2008/0039363; U.S. 2020/0179407; and EP 2 991 663 B1.

BACKGROUND

Mitochondria are the respiratory organelles of eukaryotic cells. Aerobic eukaryotes require mitochondria to produce most of their cells' adenosine triphosphate (ATP), the principal medium of intracellular chemical energy transfer, via oxidative phosphorylation (OXPHOS).

Without sufficient mitochondria, cells lack the chemical energy needed to perform basic functions, and the cells malfunction and/or die.

Mitochondria are semi-autonomous, having their own genome and cell cycle independent from the host organism's nuclear genome and cell cycle. Each mitochondrion lives, grows, maintains homeostasis, divides, and dies within our cells, guided by a complex array of signals between it, its host cell, and the host cell's environment.

Since healthy mitochondria are essential for cellular survival, it is therefore no surprise that many serious medical disorders are associated with mitochondria dysfunction. For instance, mitochondrial dysfunction has been discussed as an important contributor to pathogenesis of familial Parkinson's disease. (Bose & Beal, J. NEUROCHEM., 2016 Oct. 139 Suppl.( ) 216-231.) And mitochondrial genetic diseases, although individually rare, are collectively the most common form of genetic disease in humans. (Morgia et al., J. INT. MED. 2020, 287; 592-608.)

Cells maintain healthy populations of mitochondria through a homeostatic "turnover" process, whereby new mitochondria generate and grow while old mitochondria die and recycle. Whole categories of diseases are associated with lower-than-normal rates of mitochondrial maintenance and turnover. (Bakula & Scheibye-Knudsen, FRONT. CELL. DEV. BIOL. 2020, 8: 239; Killackey et al., J. CELL BIOL., 2020, 219:11.) Thus, new agents and methods for treating such diseases would be highly desirable.

SUMMARY

Heretofore, it was not known that MAS agonists would stimulate mitophagy, which is distinct from mitochondrial dysfunction, and therefore provides desired therapeutic benefits in a variety of diseases. Provided herein are methods of stimulating mitophagy in a subject in need thereof administering to the subject a mitophagy-stimulating amount of a MAS receptor agonist or substance that triggers endogenous production of a MAS receptor agonist.

It is contemplated that MAS agonists target mitophagy pathways and can promote mitophagy via several mechanisms (such as mTORC1; NRF2 activation; TFEB expression; inhibition of ATP hydrolysis by mitochondrial Complex V; mitochondrial dynamics) in a tissue specific manner. It is further contemplated that such mitophagy pathways may include stimulation of biogenesis (i.e. maintenance of mitochondrial mass by mitochondrial biogenesis), promotion of autophagosome formation, lysosome formation and acidification, autophagosome/lysosome fusion, and degradation of the autophagolysosome content.

The present disclosure relates to methods and agents for stimulation of mitochondrial turnover for treatment of disease in a mammal.

In some aspects, the present disclosure comprises a method of stimulating increased mitochondrial turnover in a mammal comprising administering to the mammal a pharmacologically suitable dose of a MAS receptor agonist; MAS receptor modulator; a substance that triggers endogenous production of a MAS receptor agonist; a substance that triggers endogenous production of a MAS receptor modulator; or any combination thereof. In some embodiments, the mammal is a human patient.

In some aspects, the substance that triggers endogenous production of a MAS receptor agonist is a substance that triggers endogenous production of angiotensin(1-7). In some embodiments, the substance that triggers endogenous production of angiotensin(1-7) is any of an ACE2 enzyme or analogue thereof; an ACE2 activator or analogue thereof; an ACE inhibitor or analogue thereof; or any combination thereof. In some embodiments, the substance that triggers endogenous production of angiotensin(1-7) is any of an ACE2 enzyme; an ACE2 activator; an ACE inhibitor; or any combination thereof. In some embodiments, the ACE2 enzyme is a recombinant human ACE2 enzyme. In some embodiments, the ACE2 activator is xanthenon or diminazene aceturate. In some embodiments, the ACE inhibitor is enazepril; captopril; enalapril; fosinopril; lisinopril; moexipril; perindopril; quinapril; ramipril; trandolapril; or any combination thereof.

In some embodiments, the MAS receptor agonist of the present disclosure is selected from the group consisting of a heterocyclic non-peptidic angiotensin(1-7) mimetic (such as defined herein as Formula (III)) of an analogue thereof; $Nle^3$-A(1-7) or an analogue thereof; angiotensin(1-7) or an analogue thereof; 20-hydroxyecdysone or an analogue thereof; and an 1-(p-thienylbenzyl)imidazole analogue. In one embodiment, the $Nle^3$-A(1-7) or an analogue thereof, or angiotensin(1-7) or an analogue thereof is glycosylated.

In another aspect, the MAS receptor agonist is selected from the group consisting of 5-formyl-4-methoxy-2-phenyl-1-[[4-[2-(ethylaminocarbonylsulfonamido)-5-isobutyl-3-thienyl]phenyl]methyl]imidazole.

In still another aspect, the MAS receptor agonist is selected from the group consisting of Compound 7 (defined in the disclosure herein); Compound 10 (defined in the disclosure herein); Nle$^3$-A(1-7); angiotensin(1-7); and the Ang-1-6-Ser-O-glycosylated analogue of angiotensin(1-7); and 1-(p-thienylbenzyl)imidazole. In still another aspect, the MAS receptor agonist is selected from the group consisting of Compound 7; Compound 10; Nle$^3$-A(1-7); and angiotensin(1-7).

In some embodiments, stimulating increased mitochondrial turnover results in treatment of a mammalian (such as a human) disease, disorder, or condition. In some embodiments, stimulating increased mitochondrial turnover results in treatment of a disease. In some embodiments, the disease is a disease associated with having below-normal mitochondrial turnover. In some embodiments, the disease associated with below-normal mitochondrial turnover is an inflammatory disease, a neurodegenerative disease, an ocular disease, or combination thereof.

In some embodiments, the inflammatory disease is primary biliary cirrhosis/cholangitis (PBC), sepsis, and/or renal injury/damage; wherein the neurodegenerative disease is schizophrenia; and wherein the ocular disease is Fuchs endothelial dystrophy, microphthalmia syndromic 7, Werner syndrome, and/or Fanconi anemia.

In some embodiments, the disease associated with below-normal mitochondrial turnover is any of Alzheimer's disease; amyotrophic lateral sclerosis (ALS); cardiovascular disease; frontotemporal dementia; hematopoietic disorders; Parkinson's disease; primary biliary cirrhosis/cholangitis (PBC); sepsis; renal injury/damage, or any combination thereof.

In some embodiments, the disease associated with below-normal mitochondrial turnover is any of ataxia-telangiectasia; autosomal dominant optic atrophy; Barth syndrome; Charcot-Marie-Tooth disease; Charlevoix-Saguenay spastic ataxia; Cockayne syndrome; Danon disease; Fabry disease; Fanconi anemia; Friedrich's ataxia; Fuchs endothelial dystrophy; Gaucher disease; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Pearson syndrome; Pompe disease; rhabdomyosarcoma; schizophrenia; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof.

In another embodiment, the disease associated with below-normal mitochondrial turnover is any of Alzheimer's disease; amyotrophic lateral sclerosis (ALS); ataxia-telangiectasia; autosomal dominant optic atrophy; Barth syndrome; cardiovascular disease; Charcot-Marie-Tooth disease; Charlevoix-Saguenay spastic ataxia; Cockayne syndrome; Danon disease; Fabry disease; Fanconi anemia; Friedrich's ataxia; frontotemporal dementia; Fuchs endothelial dystrophy; Gaucher disease; hematopoietic disorders; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Parkinson's disease; Pearson syndrome; Pompe disease; primary biliary cirrhosis/cholangitis (PBC); rhabdomyosarcoma; schizophrenia; sepsis; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof.

In still another embodiment, the disease associated with below-normal mitochondrial turnover is any of mitochondrial DNA depletion syndromes (MDDS); mitochondrial neurogastrointestinal encephalomyopathy (MNGIE); mitochondrial recessive ataxia syndrome (MIRAS); Leber's hereditary optic neuropathy (LHON); myoclonus epilepsy with ragged red fibers (MERRF); neuropathy, ataxia, and retinitis pigmentosa (NARP); maternally inherited diabetes and deafness syndrome (MIDD); mitochondrial encephalopathy, lactic acidosis, and stroke-like episodes (MELAS); Pearson syndrome; Barth syndrome; mtDNA heteroplasmy; rhabdomyosarcoma; Friedrich's ataxia; methylmalonic acidemia (MMA); lactic acidosis; Leigh syndrome; Kearns-Sayre syndrome; or any combination thereof.

In yet another embodiment, the disease associated with below-normal mitochondrial turnover is Alzheimer's disease; amyotrophic lateral sclerosis (ALS); ataxia-telangiectasia; autosomal dominant optic atrophy; Barth syndrome; cardiovascular disease; Charcot-Marie-Tooth disease; Charlevoix-Saguenay spastic ataxia; Cockayne syndrome; Danon disease; Fabry disease; Fanconi anemia; frontotemporal dementia; Gaucher disease; hematopoietic disorders; intellectual developmental disorder with short stature and variable skeletal anomalies; Krabbe disease; Lafora disease; microcephaly 18; mental retardation, X-linked, syndromic, Turner type (MRXST); mucolipidosis II; multiple sulfatase deficiency; neurodegeneration with ataxia, dystonia, and gaze palsy (NADGP); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; Parkinson's disease; Pompe disease; spastic paraplegia type 15; spastic paraplegia 49; spinocerebellar ataxia 4; spinocerebellar ataxia 25; Vici syndrome; Wolfram syndrome; xeroderma pigmentosum (XP) group A; Zellweger syndrome; or any combination thereof.

In some embodiments, stimulating increased mitochondrial turnover in a mammal comprises administering to the mammal a pharmacologically suitable dose of a MAS receptor agonist; MAS receptor modulator; a substance that triggers endogenous production of a MAS receptor agonist; a substance that triggers endogenous production of a MAS receptor modulator; or any combination thereof, further includes co-administering a pharmaceutically acceptable excipient, carrier, adjuvant, buffer, preservative, chelator, nuclease, anti-fungal agent, anti-bacterial agent, or any combination thereof. In some embodiments, the MAS receptor agonist; MAS receptor modulator; substance that triggers endogenous production of a MAS receptor agonist; substance that triggers endogenous production of a MAS receptor modulator; or any combination thereof further includes a pharmaceutically acceptable excipient, carrier, adjuvant, buffer, preservative, chelator, nuclease, anti-fungal agent, anti-bacterial agent, or any combination thereof.

In some embodiments, the pharmacologically suitable dose of MAS receptor agonist is 0.01-500 $mg_{agent}/kg_{patient}$. In some embodiments, the pharmacologically suitable dose of MAS receptor agonist; MAS receptor modulator; substance that triggers endogenous production of a MAS receptor agonist; substance that triggers endogenous production of a MAS receptor modulator; or any combination thereof is 0.01-500 $mg_{agent}/kg_{patient}$.

In some embodiments, the MAS receptor agonist; MAS receptor modulator; substance that triggers endogenous production of a MAS receptor agonist; substance that triggers endogenous production of a MAS receptor modulator; or any combination thereof is administered topically, orally, intravenously, intramuscularly, intraocularly, intradermally, rectally, by oral inhalation, by nasal inhalation, parenterally, buccally, epidurally, intracerebrally, intracerebroventricularly, or any combination thereof. In some embodiments, the MAS receptor agonist; MAS receptor modulator; substance that triggers endogenous production of a MAS receptor agonist; substance that triggers endogenous production of a MAS receptor modulator; or any combination thereof is delivered via intravenous drip, hypodermic needle, capsule, tablet, topical gel/cream/solution, dermal patch, or any combination thereof. In another embodiment, the MAS receptor agonist is administered topically, orally, intravenously, intramuscularly, intraocularly, intradermally, rectally, by oral inhalation, by nasal inhalation, parenterally, buccally, epidurally, intracerebrally, intracerebroventricularly, or any combination thereof. In some embodiments, the MAS receptor agonist; MAS receptor modulator; substance that triggers endogenous production of a MAS receptor agonist; substance that triggers endogenous production of a MAS receptor modulator; or any combination thereof is delivered via intravenous drip, hypodermic needle, capsule, tablet, topical gel/cream/solution, dermal patch, or any combination thereof. In one embodiment, the MAS receptor agonist is delivered via intravenous drip, hypodermic needle, capsule, tablet, topical gel/cream/solution, dermal patch, or any combination thereof.

In another aspect, the present disclosure comprises a method of treating a human patient having a disease associated with lower-than-normal mitochondrial turnover, comprising the steps of: diagnosing the patient with a disease associated with lower-than-normal mitochondrial turnover; and administering a pharmacologically effective dose of a mitochondrial-turnover-stimulating drug. In some embodiments, the mitochondrial-turnover-stimulating drug is selected from the group consisting of: an analogue of a heterocyclic non-peptidic angiotensin(1-7) mimetic compound; angiotensin(1-7) or an analogue thereof; $Nle^3$-A(1-7) analogue thereof; 20-hydroxyecdysone or an analogue thereof; and an analogue of a 1-(p-thienylbenzyl)imidazole. In some embodiments, the mitochondrial-turnover-stimulating drug is selected from the group consisting of: a heterocyclic non-peptidic angiotensin(1-7) mimetic or an analogue thereof; $Nle^3$-A(1-7) or an analogue thereof; angiotensin(1-7) or an analogue thereof; a 1-(p-thienylbenzyl)imidazole analogue; and 20-hydroxyecdysone or an analogue thereof. In some embodiments, the mitochondrial-turnover-stimulating drug further includes a pharmaceutically acceptable excipient, carrier, adjuvant, buffer, preservative, chelator, nuclease, anti-fungal agent, anti-bacterial agent, or any combination thereof. In some embodiments, the mitochondrial-turnover-stimulating drug is delivered via intravenous drip, hypodermic needle, capsule, tablet, topical gel/cream/solution, dermal patch, or any combination thereof. In some embodiments, the mitochondrial-turnover-stimulating drug is administered topically, orally, intravenously, intramuscularly, intraocularly, intradermally, rectally, by oral inhalation, by nasal inhalation, parenterally, buccally, epidurally, intracerebrally, intracerebroventricularly, or any combination thereof.

In an embodiment, the disease associated with below-normal mitochondrial turnover is Alzheimer's disease; amyotrophic lateral sclerosis (ALS); ataxia-telangiectasia; autosomal dominant optic atrophy; Barth syndrome; cardiovascular disease; Charcot-Marie-Tooth disease; Charlevoix-Saguenay spastic ataxia; Cockayne syndrome; Danon disease; Fabry disease; Fanconi anemia; Friedrich's ataxia; frontotemporal dementia; Fuchs endothelial dystrophy; Gaucher disease; hematopoietic disorders; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Parkinson's disease; Pearson syndrome; Pompe disease; primary biliary cirrhosis/cholangitis (PBC); rhabdomyosarcoma; schizophrenia; sepsis; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof.

In one embodiment, the patient is diagnosed using at least a mitophagy assay. In some embodiments, the mitophagy assay is used to assess mitochondrial function and is an assay that measures: oxygen consumption; the amount of mitochondrial DNA (mtDNA) mutations, or deletions, or mutations and deletions; the mtDNA copy number; or the activity of a mitochondrial enzyme.

In some embodiments, the pharmacologically effective dose of mitochondrial-turnover-stimulating drug, i.e., MAS receptor agonist; MAS receptor modulator; substance that triggers endogenous production of a MAS receptor agonist; substance that triggers endogenous production of a MAS receptor modulator; or any combination thereof, is 0.01-500 $mg_{agent}/kg_{patient}$.

In still another embodiment, the MAS receptor agonist further includes a pharmaceutically acceptable excipient, carrier, adjuvant, buffer, preservative, chelator, nuclease, anti-fungal agent, anti-bacterial agent, or any combination thereof. In some embodiments, the MAS receptor agonist is administered topically, orally, intravenously, intramuscularly, intraocularly, intradermally, rectally, by oral inhalation, by nasal inhalation, parenterally, buccally, epidurally, intracerebrally, intracerebroventricularly, or any combination thereof. The MAS receptor agonist may be delivered via intravenous drip, hypodermic needle, capsule, tablet, topical gel/cream/solution, dermal patch, or any combination thereof.

In one embodiment, the present disclosure comprises a method of treating a human patient having a disease associated with lower-than-normal mitochondrial turnover, comprising the steps of: diagnosing the patient with a disease associated with lower-than-normal mitochondrial turnover, wherein the diagnosis is rendered using at least a mitophagy assay; wherein the disease associated with lower-than-normal mitochondrial turnover is Alzheimer's disease; amyotrophic lateral sclerosis (ALS); ataxia-telangiectasia; autosomal dominant optic atrophy; Barth syndrome; cardiovascular disease; Charcot-Marie-Tooth disease; Charlevoix-Saguenay spastic ataxia; Cockayne syndrome; Danon disease; Fabry disease; Fanconi anemia; Friedrich's ataxia; frontotemporal dementia; Fuchs endothelial dystrophy; Gaucher disease; hematopoietic disorders; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Parkinson's disease; Pearson syndrome; Pompe disease; primary biliary cirrhosis/cholangitis (PBC); rhabdomyosarcoma; schizophrenia; sepsis; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof; and administering a pharmacologically effective dose of a mitochondrial-turnover-stimulating drug, wherein the mitochondrial-turnover-stimulating drug is selected from the group consisting of a heterocyclic non-peptidic angiotensin(1-7) mimetic compound or an analogue thereof; angiotensin(1-7) or an analogue thereof; $Nle^3$-A(1-7) or an analogue thereof; 20-hydroxyecdysone or an analogue thereof; and an analogue of a 1-(p-thienylbenzyl)imidazole.

In some embodiments, the pharmacologically effective dose of mitochondrial-turnover-stimulating drug, i.e., MAS receptor agonist; MAS receptor modulator; substance that triggers endogenous production of a MAS receptor agonist; substance that triggers endogenous production of a MAS receptor modulator; or any combination thereof, is 0.01-500 $mg_{agent}/kg_{patient}$.

In an embodiment, the MAS receptor agonist further includes a pharmaceutically acceptable excipient, carrier, adjuvant, buffer, preservative, chelator, nuclease, anti-fungal agent, anti-bacterial agent, or any combination thereof. In another embodiment of the method, the MAS receptor agonist is administered topically, orally, intravenously, intramuscularly, intraocularly, intradermally, rectally, by oral inhalation, by nasal inhalation, parenterally, buccally, epidurally, intracerebrally, intracerebroventricularly, or any combination thereof.

In an embodiment, the present disclosure comprises a method of treating a human patient having a disease associated with lower-than-normal mitochondrial turnover, comprising: administering a pharmacologically effective dose of MAS receptor agonist; wherein the disease associated with lower-than-normal mitochondrial turnover is Alzheimer's disease; amyotrophic lateral sclerosis (ALS); ataxia-telangiectasia; autosomal dominant optic atrophy; Barth syndrome; cardiovascular disease; Charcot-Marie-Tooth disease; Charlevoix-Saguenay spastic ataxia; Cockayne syndrome; Danon disease; Fabry disease; Fanconi anemia; Friedrich's ataxia; frontotemporal dementia; Fuchs endothelial dystrophy; Gaucher disease; hematopoietic disorders; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Parkinson's disease; Pearson syndrome; Pompe disease; primary biliary cirrhosis/cholangitis (PBC); rhabdomyosarcoma; schizophrenia; sepsis; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof.

In some embodiments, the pharmacologically effective dose of MAS receptor agonist; MAS receptor modulator; substance that triggers endogenous production of a MAS receptor agonist; substance that triggers endogenous production of a MAS receptor modulator; or any combination thereof is 0.01-500 $mg_{agent}/kg_{patient}$. In some embodiments, the pharmacologically effective dose of MAS receptor agonist is 0.01-500 $mg_{agent}/kg_{patient}$.

In one embodiment, the MAS receptor agonist further includes a pharmaceutically acceptable excipient, carrier, adjuvant, buffer, preservative, chelator, nuclease, anti-fungal agent, anti-bacterial agent, or any combination thereof. In another embodiment, the MAS receptor agonist is administered topically, orally, intravenously, intramuscularly, intraocularly, intradermally, rectally, by oral inhalation, by nasal inhalation, parenterally, buccally, epidurally, intracerebrally, intracerebroventricularly, or any combination thereof.

In any one of the embodiments of the present disclosure, the 1-(p-thienylbenzyl)imidazole analogue is a compound of Formula (I):

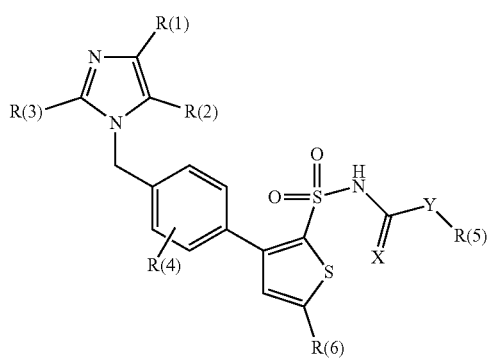

(I)

in which: R(1) is (1) halogen; (2) hydroxyl; (3) $(C_1-C_4)$-alkoxy; (4) $(C_1-C_8)$-alkoxy, wherein 1 to 6 carbon atoms are replaced by the heteroatoms O, S, or NH, (5) $(C_1-C_4)$-alkoxy, substituted by a saturated cyclic ether; (6) O—$(C_1-C_4)$-alkenyl; (7) O—$(C_1-C_4)$-alkylaryl; or (8) phenoxy, unsubstituted or substituted by a substituent selected from halogen, $(C_1-C_3)$-alkyl, $(C_1-C_3)$-alkoxy, and trifluoromethyl; R(2) is (1) CHO; R(3) is (1) $(C_1-C_4)$-alkyl; or (2) aryl; R(4) is (1) hydrogen; (2) halogen; or (3) $(C_1-C_4)$-alkyl; X is (1) oxygen; or (2) sulfur; Y is (1) oxygen; or (2) —NH—; R(5) is (1) hydrogen; (2) $(C_1-C_6)$-alkyl; or (3) $(C_1-C_4)$-alkylaryl; where R(5) can only be hydrogen if Y has the meaning mentioned under (2); and R(6) is (1) $(C_1-C_5)$-alkyl; in any stereoisomeric form or mixture thereof in any ratio, or a physiologically acceptable salt thereof.

In any one of the embodiments of the present disclosure, the 1-(p-thienylbenzyl)imidazole analogue is a compound of Formula (II):

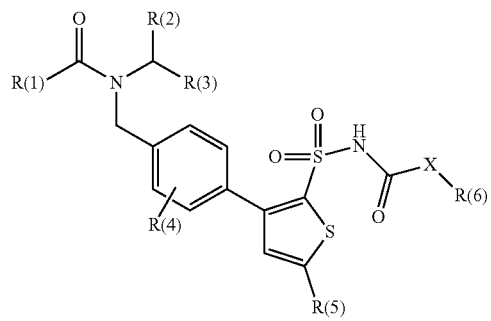

(II)

in which: R(1) is chosen from among 1. $(C_1-C_5)$-alkyl, unsubstituted or substituted by a radical chosen from among $NH_2$, halogen, O$(C_1-C_3)$-alkyl, CO—O—$(C_1-C_3)$-alkyl and $CO_2H$; 2. $(C_3-C_8)$-cycloalkyl; 3. $(C_1-C_3)$-alkyl-$(C_3-C_5)$-cycloalkyl; 4. $(C_6-C_{10})$-aryl, unsubstituted or substituted by a radical chosen from halogen and O—$(C_1-C_3)$-alkyl; 5. $(C_1-C_3)$-alkyl-$(C_6-C_{10})$-aryl, where the aryl radical is unsubstituted or substituted by a radical chosen from halogen and O—$(C_1-C_3)$-alkyl; 6. $(C_3-C_5)$-heteroaryl; and 7. $(C_1-C_3)$-alkyl-$(C_1-C_5)$-heteroaryl; R(2) is chosen from among 1. hydrogen; 2. $(C_1-C_6)$-alkyl, unsubstituted or substituted by a radical chosen from halogen and O—$(C_1-C_3)$-alkyl; 3. $(C_3-C_5)$-cycloalkyl; 4. $(C_1-C_3)$-alkyl-$(C_3-C_5)$-cycloalkyl; 5. $(C_6-C_{10})$-aryl, unsubstituted or substituted by a radical chosen from among halogen, O—$(C_1-C_3)$-alkyl and CO—O—$(C_1-C_3)$-alkyl; and 6. $(C_1-C_3)$-alkyl-$(C_6-C_{10})$-aryl, unsubstituted or substituted by a radical chosen from halogen and O—$(C_1-C_3)$-alkyl; R(3) is chosen from among 1. hydrogen; 2. COOH; and 3. COO—$(C_1-C_4)$-alkyl; R(4) is chosen from among 1. hydrogen; 2. halogen; and 3. $(C_1-C_4)$-alkyl; R(5) is chosen from 1. hydrogen, and 2. $(C_1-C_6)$-alkyl; R(6) is chosen from among hydrogen; 2. $(C_1-C_6)$-alkyl; 3. $(C_1-C_3)$-alkyl-$(C_3-C_5)$-cycloalkyl; and 4. $(C_2-C_6)$-alkenyl; X is chosen from 1. oxygen, and 2. NH; in all the stereoisomeric forms thereof, and mixtures thereof in all ratios, and the physiologically tolerated salts thereof.

In some embodiments, the 1-(p-thienylbenzyl)imidazole is 5-formyl-4-methoxy-2-phenyl-1-[[4-[2-(ethylaminocarbonylsulfonamido)-5-isobutyl-3-thienyl]phenyl]methyl]imidazole, which is the compound pictured below:

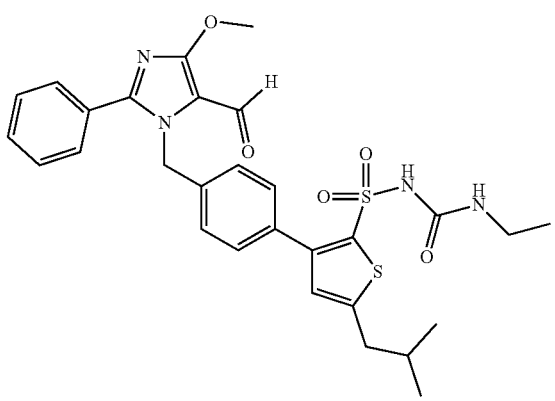 [SMILES: CCNC(=O)NS(=O)(=O)c1sc(CC(C)C)cc1-c1ccc(Cn2c(-c3ccccc3)nc(OC)c2C=O)cc1]

In any embodiment of the present disclosure, the heterocyclic non-peptidic angiotensin(1-7) mimetic compound is a compound of formula (III):

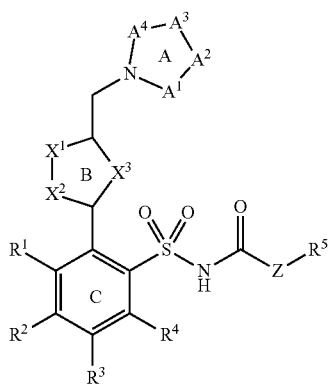

(III)

wherein: ring A is a five-membered or six-membered heteroaryl or heterocyclyl ring containing either a combination of two non-adjacent nitrogen or oxygen atoms, or a combination of three or four nitrogen or oxygen atoms; ring B is a five-membered or six-membered heteroaryl ring that contains at least one nitrogen atom; ring C is an optionally substituted aryl ring; $A^1$, $A^2$, $A^3$, $A^4$ are independently selected from a group consisting of =N—, —C(=O)—, —C($R^a$)=, =C($R^b$)—, —C($R^c$)($R^d$)—N($R^e$)—, —C($R^c$)($R^d$)—O—, or —[C($R_c$)($R^d$)]$_n$— with n being 1 or 2; $X^1$—$X^2$ is ($R^6$)C—N, N—C($R^6$), N—N, N—O, O—N, N—S or S—N; $X^3$ is ($R^7$)C=C($R^8$), O, S, or N($R^9$); Z is O, NH or a bond to $R^5$; $R^a$ and $R^b$ are independently selected from the group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^a$ and $R^b$ can also join to form a ring of up to 6 atoms; $R^c$ and $R^d$ are independently selected from a group consisting of hydrogen, alkyl, aryl, or heteroaryl, provided that $R^c$ and $R^d$ can also join to form a ring of up to 6 atoms; $R^e$ is hydrogen, alkyl, aryl, heteroaryl, acyl, alkoxyacyl, aminoacyl, dialkylaminoacyl, or dialkylaminoacyl; $R^1$, $R^3$, $R^4$, $R^6$, $R^7$, and $R^8$ are independently selected from a group consisting of hydrogen, alkyl, alkenyl, alkynyl, aryl, heteroaryl, arylmethyl, heteroarylmethyl, fluoro, bromo, iodo, cyano, hydroxy, amino, alkylamino, alkoxy, aryloxy, alkoxyalkyl, or aryloxyalkyl; $R^2$ is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl; $R^5$ is alkyl, aryl, heteroaryl, hydroxyalkyl, carboxyalkyl, alkoxyalkyl, or aryloxyalkyl; and $R^9$ is hydrogen, alkyl, aryl, heteroaryl, acyl, alkoxyacyl, aminoacyl, dialkylaminoacyl, or dialkylaminoacyl; or a pharmaceutically acceptable salt thereof.

In any embodiment of the present disclosure, the 20-hydroxyecdysone analogue is a compound of formula (IV):

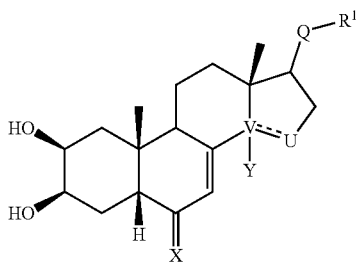

(IV)

wherein: V—U is a single carbon-carbon bond and Y is a hydroxyl group or a hydrogen, or V—U is a C=C ethylene bond; X is an oxygen, Q is a carbonyl group; $R^1$ is chosen from: a group ($C_1$-$C_6$)W($C_1$-$C_6$); a group ($C_1$-$C_6$)W($C_1$-$C_6$)W($C_1$-$C_6$); a group ($C_1$-$C_6$)W($C_1$-$C_6$)CO$_2$($C_1$-$C_6$); a group ($C_1$-$C_6$)A, A representing a heterocycle optionally substituted by a group of the type OH, OMe, ($C_1$-$C_6$), N($C_1$-$C_6$), CO$_2$($C_1$-$C_6$); a CH$_2$Br group; W being a heteroatom chosen from N, O and S.

In any embodiment of the present disclosure, the angiotensin(1-7) analogue is a sequence consisting of at least three contiguous amino acids of groups $R_1$—$R_8$ in the sequence of general formula (i) $R_1$-$R_2$-$R_3$-$R_4$-$R_5$-$R_6$-$R_7$-$R_8$ in which $R_1$ and $R_2$ together form a group of formula X—$R_A$-$R_B$—, wherein X is H or a one- to three-peptide group; $R_A$ is selected from Asp, Glu, Asn, Acpc, Ala, Me2Gly, Pro, Bet, Glu(NH$_2$), Gly, Asp(NH$_2$), Suc, and glycosylated forms thereof; $R_B$ is selected from Arg, Lys, Ala, Orn, Ser(Ac), Sar, D-Arg, D-Lys, His, and glycosylated forms thereof; $R_3$ is selected from the group consisting of Val, Ala, Leu, Nle, Ile, Gly, Pro, Aib, Acpc, Lys, Tyr, and glycosylated forms thereof; $R^4$ is selected from the group consisting of Tyr, Tyr(PO$_3$)$_2$, Thr, Ser, Hse, Ala, azaTyr, Tyr, Phe, and glycosylated forms thereof; $R_5$ is selected from the group consisting of Ile, Ala, Leu, Nle, Val, Gly, and glycosylated forms thereof; $R_6$ is His, Arg, 6-NH$_2$-Phe, Lys, and glycosylated forms thereof; $R_7$ is Pro, Ala, Gly, Ser, or glycosylated forms thereof; and $R^8$ is selected from the group consisting of Phe, Phe(Br), Ile, Tyr, Ser, Thr, Hyp, and glycosylated forms thereof. In some embodiments of formula (i), formula (i) excludes sequences including $R_4$ as a terminal Tyr group.

In any embodiment of the present disclosure, an analogue of angiotensin(1-7) may also comprise a sequence of the general formula (ii) Ala$_1$-$R_2$—$R_3$—$R_4$—$R_5$—$R_6$—$R_7$ wherein $R_2$ is selected from Arg, Lys, Ala, Cit, Orn, Ser(Ac), Sar, D-Arg, and D-Lys; $R_3$ is selected from the group consisting of Val, Ala, Leu, Nle, Ile, Gly, Pro, Aib, Acpc, Lys, and Tyr; $R_4$ is Ser, or forms a cyclic thioether with $R_7$; $R_5$ is selected from the group consisting of Ile, Ala, Leu, Nle, Val, and Gly; $R_6$ is His, Arg, 6-NH$_2$-Phe, Lys, and glycosylated forms thereof; and $R_7$ is Cys or forms a cyclic thioether with $R_4$.

In any embodiment of the present disclosure, the disease may be a disease associated with having higher-than-normal levels of mitophagy. In any embodiment of the present disclosure, the disease is a disease associated with having lower-than-normal levels of mitochondrial biogenesis.

BRIEF DESCRIPTION OF DRAWINGS

Exemplary embodiments of the present disclosure will be better understood and readily apparent to one of ordinary skill in the art from the following written description, by way of example only, and in conjunction with the drawings, in which:

FIGS. 11A, 11B, 11C, 11D, 11E, 11F, 11G, and 11H depict super-resolution micrographs cells following treatment with DMSO negative control; A779 (MAS receptor inhibitor); angiotensin(1-7); angiotensin(1-7)+A779; $Nle^3$-A(1-7); $Nle^3$-A(1-7)+A779; Compound 7; and Compound 7+A779.

FIG. 12 depicts a table briefly describing the morphology of cellular mitochondria in cells following 8 hours, 24 hours, and 72 hours treatment with angiotensin(1-7), $Nle^3$-A(1-7), or Compound 7.

DETAILED DESCRIPTION

Figure 1A:
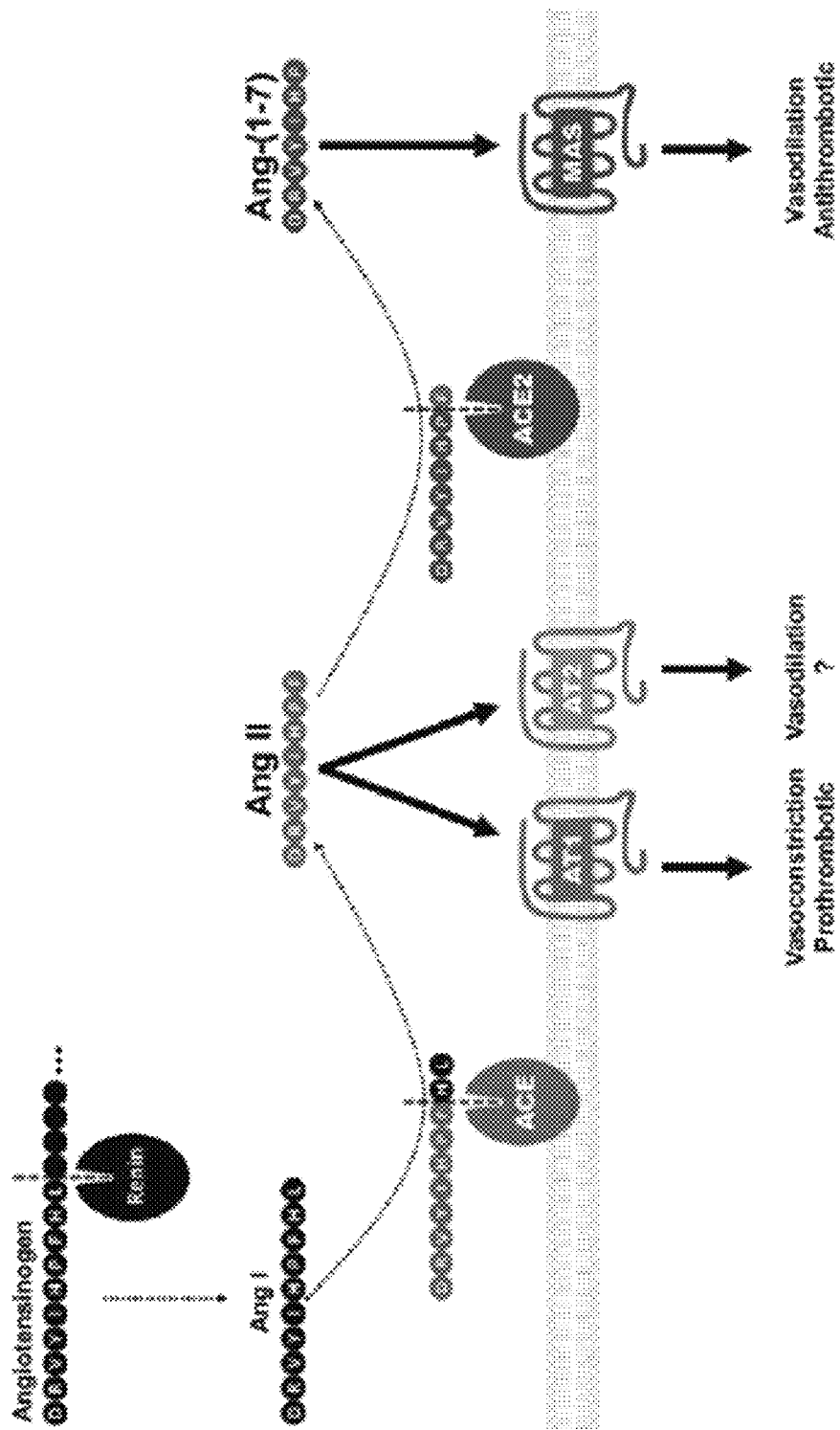
FIG. 1A depicts an exemplary schematic of MAS receptor's role in the angiotensin cell signaling pathway.

The present subject matter may be understood more readily by reference to the following detailed description which forms a part of this disclosure. It is to be understood that this disclosure is not limited to the specific products, methods, conditions or parameters described and/or shown herein, and that the terminology used herein is for the purpose of describing particular embodiments by way of example only and is not intended to be limiting of the claimed disclosure.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings:

In the present disclosure, the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value.

Similarly, when values are expressed as approximations, by use of the antecedent "about," it is understood that the particular value forms another embodiment. All ranges are inclusive and combinable. In the context of the present disclosure, by "about" a certain amount it is meant that the amount is within ±20% of the stated amount, or within ±10% of the stated amount, or within ±5% of the stated amount.

As used herein, the terms "treat", "treatment", or "therapy" (as well as different forms thereof) refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. Those in need of treatment include those already with the disease or condition as well as those prone to having the disease or condition or those in which the disease or condition is to be prevented.

The terms "subject," "individual," and "patient" are used interchangeably herein, and refer to an animal, for example a human, to whom treatment with a composition or formulation in accordance with the present disclosure, is provided. The term "subject" as used herein refers to human and non-human animals. The human can be any human of any age. In an embodiment, the human is an adult. In another embodiment, the human is a child. The human can be male, female, pregnant, middle-aged, adolescent, or elderly.

Conditions and disorders in a subject for which a particular drug, compound, composition, formulation (or combination thereof) is said herein to be "indicated" are not restricted to conditions and disorders for which that drug or compound or composition or formulation has been expressly approved by a regulatory authority, but also include other conditions and disorders known or reasonably believed by a physician or other health or nutritional practitioner to be amenable to treatment with that drug or compound or composition or formulation or combination thereof.

An "analogue" (or "analog") will be readily understood to one having ordinary skill in the art as a compound having substantially the same chemical structure as a comparator compound, but differing in substitutions of atoms and/or functional groups and/or sub-structures. Where a chemical-structural definition of analogues of a particular compound is not otherwise provided in the disclosure herein, the ordinary definition provided in this paragraph shall apply.

It should be readily understood to one having ordinary skill in the art that a disease may have multiple interchangeable names (i.e., amyotrophic lateral sclerosis (ALS) is the same condition as Lou Gehrig's disease, Charcot disease, and motor neurone disease (MND)).

"Mitochondrial turnover" refers to the processes by which defective mitochondria are eliminated while new mitochondria are biogenerated and grown. Mitochondria divide and proliferate by fission, while old and defective mitochondria are primarily eliminated by mitophagy (i.e., autophagy/macroautophagy). In general, a higher rate of mitochondrial turnover is associated with having a population of younger, healthier mitochondria. Conversely, a lower rate of mitochondrial turnover is associated with having a population of older, defective mitochondrial, leading to diminished cellular function. Impaired mitophagy disrupts the mitochondrial turnover process, and is associated with numerous pathologies. (Bakula & Scheibye-Knudsen, FRONT. CELL. DEV. BIOL. 2020, 8: 239; Killackey et al., J. CELL BIOL., 2020, 219:11.)

Recently, it was discovered that certain compounds that modulate the G-protein-coupled receptor MAS cause an increased rate of mitochondrial turnover. MAS receptor had previously not been regarded as at all related to mitochondrial function-MAS receptor is best known to play an essential signaling role in the renin-angiotensin-aldosterone system (RAAS), an endocrine signaling system traditionally understood to regulate kidney function and blood pressure. The discovery of MAS receptor's role in mitochondrial turnover was exciting and unexpected, as MAS receptor may now provide a new avenue for ameliorating numerous diseases attributable to mitochondrial dysfunction.

The present disclosure relates to medical intervention methods and agents, namely methods and agents for stimulation of mitochondrial turnover for treatment of disease in a mammal.

By increasing MAS receptor signaling by, e.g., (1) activating MAS receptor; (2) increasing the sensitivity of MAS receptor; (3) increasing the steric availability of MAS receptor; (4) increasing the membrane surface presentation and/or quantity of MAS receptor; (5) other means; or any combination thereof, the rate of mitochondrial turnover in the cell is made to increase.

MAS Agonists or Substances that Trigger Endogenous Production of a MAS Receptor Agonist.

The agent which effectuating the increase in MAS receptor signaling may be a small molecule drug, peptide, protein, or any other biomolecule. The agent may act directly on MAS receptor, or may be upstream to another effectuator. For example, ACE enzyme is known to catalyze production of angiotensin(1-7), which in turn is a MAS receptor agonist.

Figure 1B:
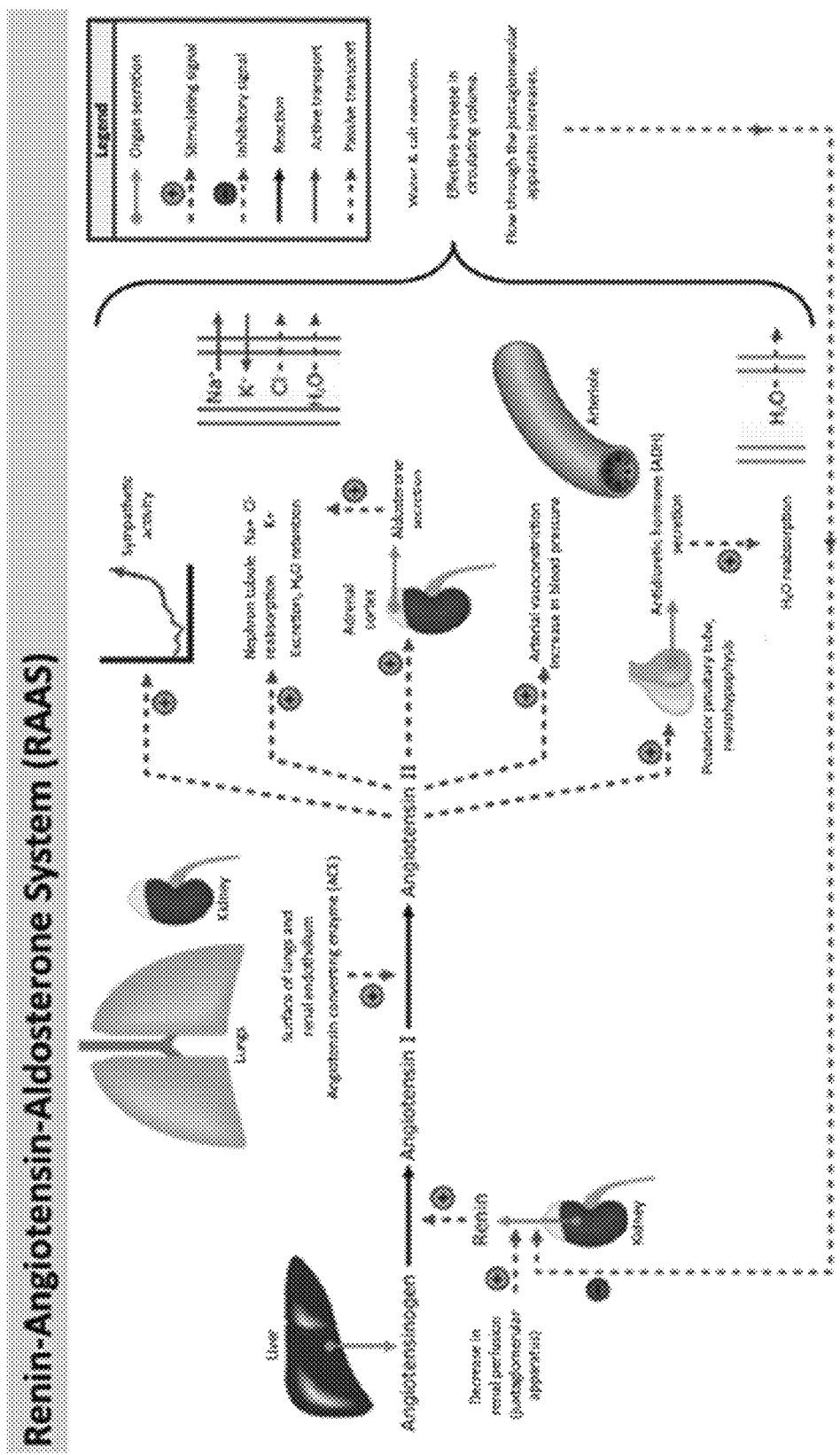
FIG. 1B depicts an exemplary schematic of the canonical renin-angiotensin-aldosterone system (RAAS).
Figure 2A:
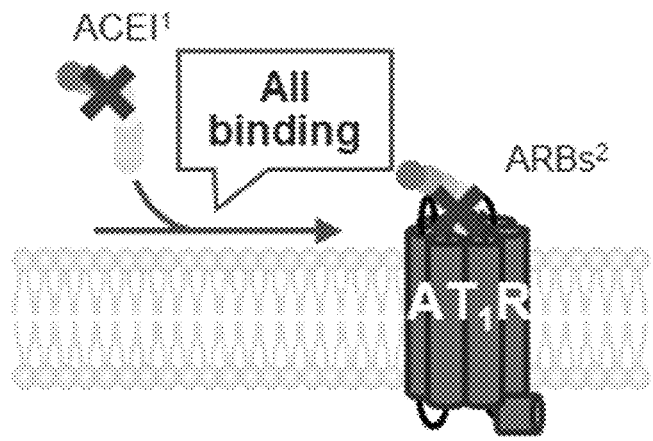
FIG. 2A depicts a cell-signaling schematic of a traditional pharmacological intervention strategy in the RAAS system, using, e.g., ACE inhibitors or angiotensin II receptor blockers.
Figure 2B:
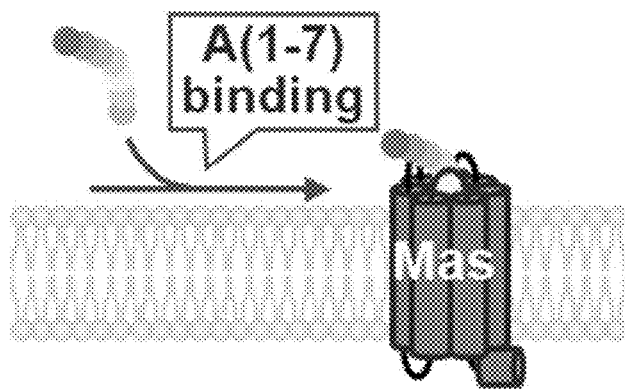
FIG. 2B depicts a cell-signaling schematic of angiotensin (1-7) affecting MAS receptor.
Figure 3A:
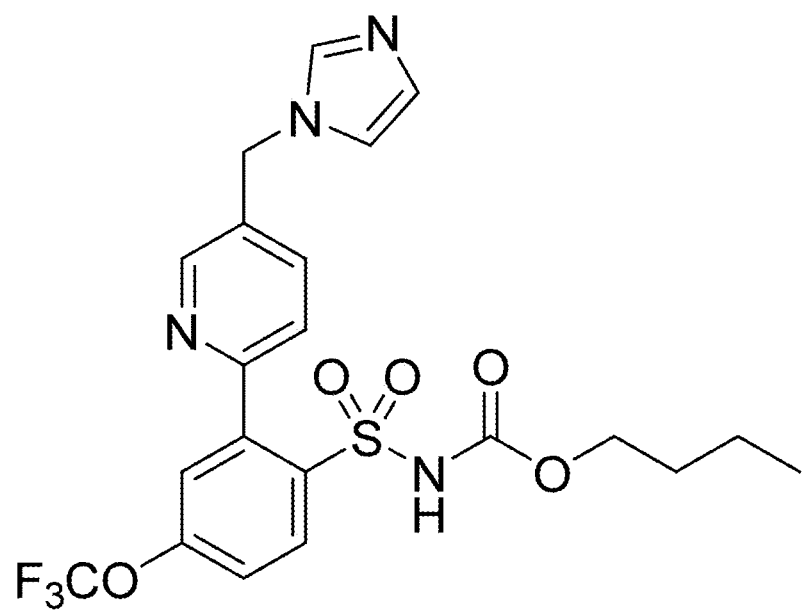
FIG. 3A depicts the chemical structure of the small molecule defined herein as "Compound 7".
Figure 3B:
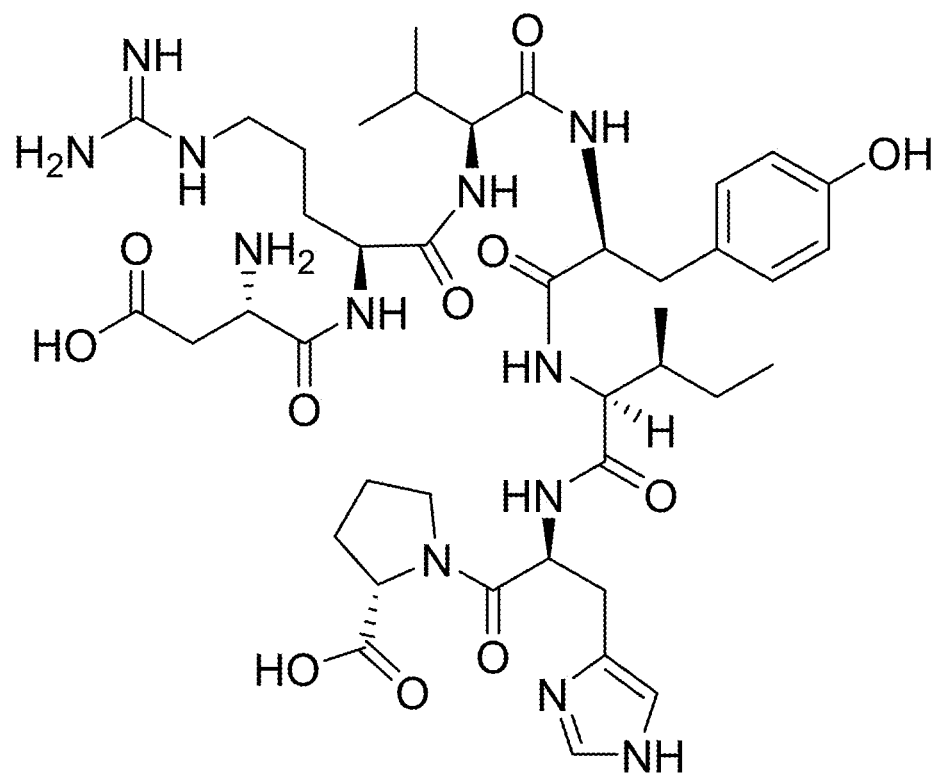
FIG. 3B depicts the chemical structure of the heptapeptide angiotensin(1-7).
Figure 3C:
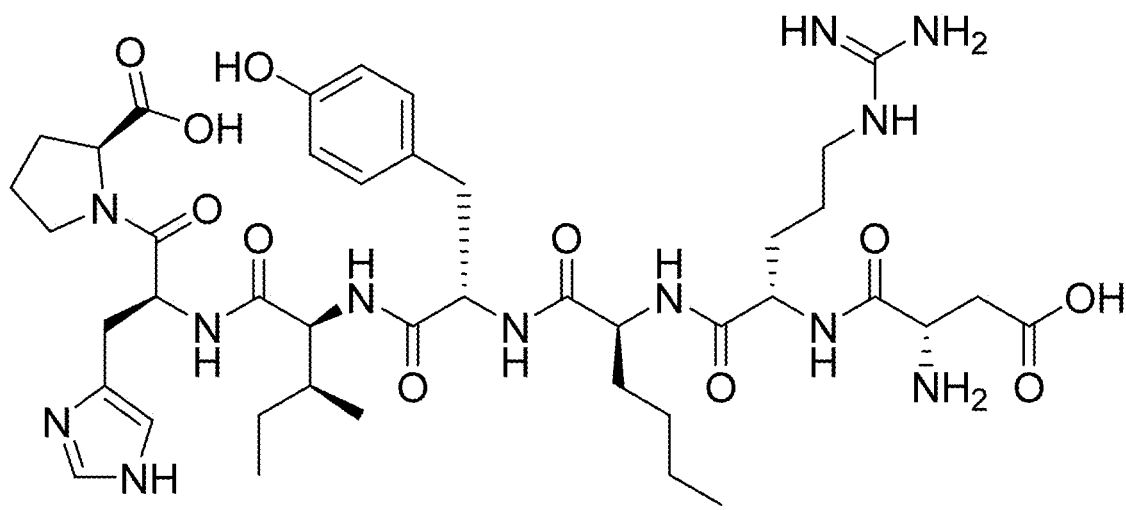
FIG. 3C depicts the chemical structure of the synthetic peptide $Nle^3$-A(1-7), also known as aclerastide.
Figure 3D:
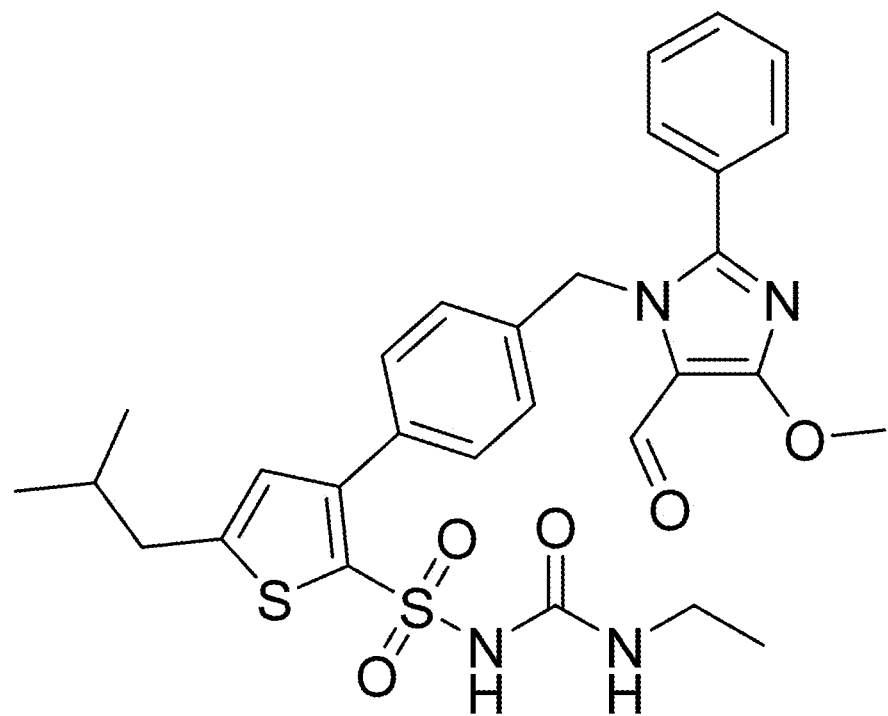
FIG. 3D depicts the chemical structure of the small molecule 5-formyl-4-methoxy-2-phenyl-1-[[4-[2-(ethylaminocarbonylsulfonamido)-5-isobutyl-3-thienyl]phenyl]methyl]imidazole.
Figure 4:
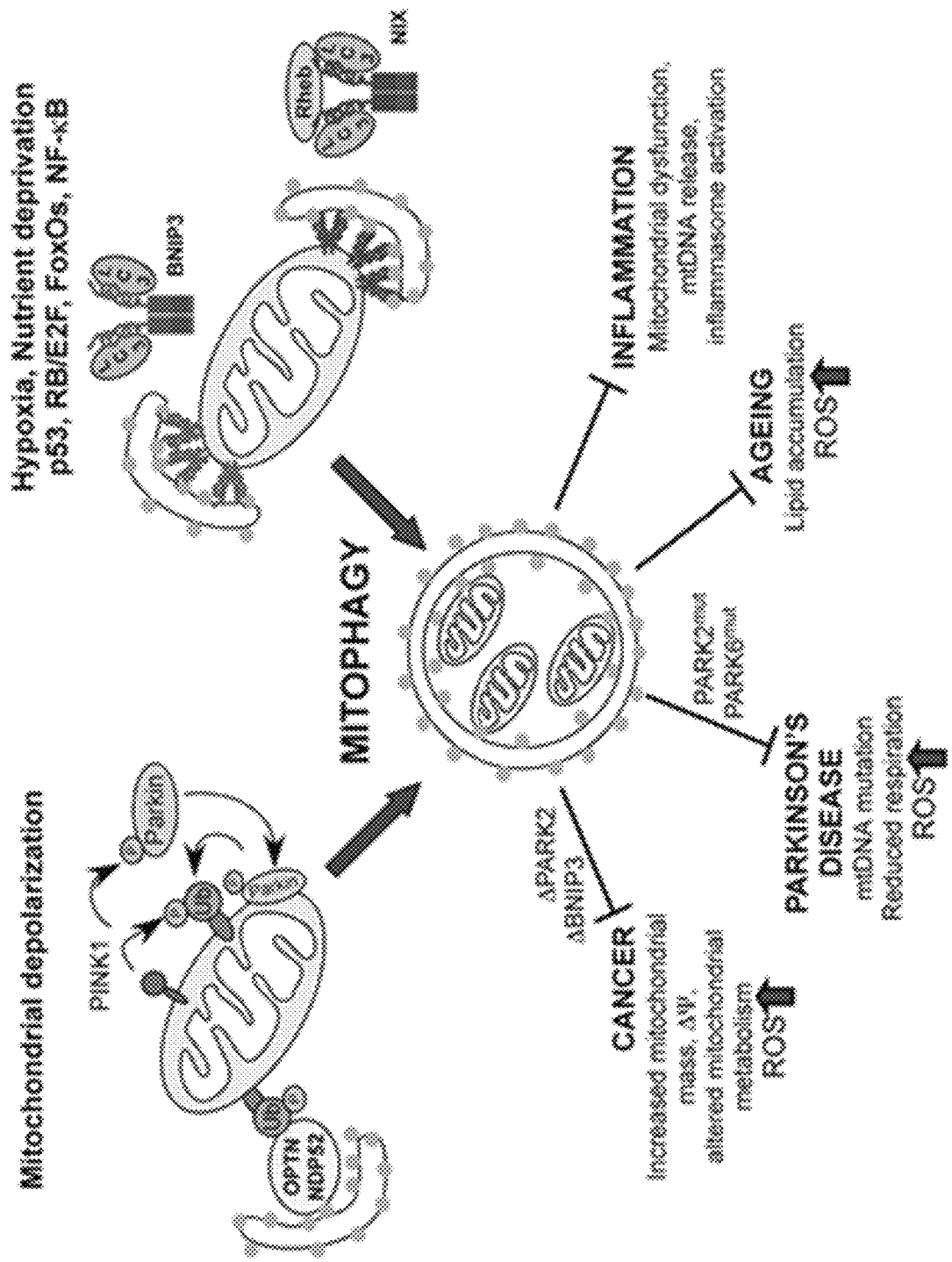
FIG. 4 depicts a schematic of biomolecular causes of mitophagy, and some exemplary downstream pathogeneses therefrom.
Figure 5:
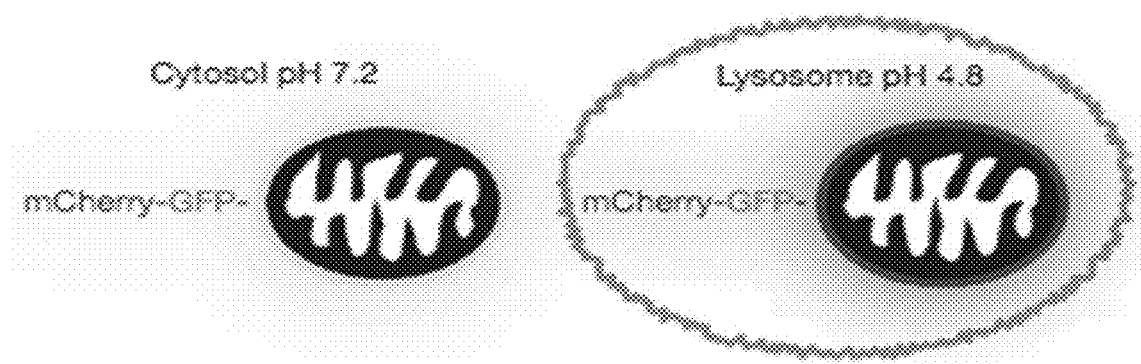
FIG. 5 depicts a fluorescent probe assay for mitophagy in a eukaryotic cell.

The MAS receptor (also called MAS1 or MASR) is a G-protein-coupled receptor (GPCR) encoded by Mas1, having a well-characterized role in the renin-angiotensin-aldosterone system (RAAS) cardiovascular endocrine pathway, outlined at FIG. 1B. RAAS (also sometimes abbreviated RAS) is a hormone system acting on the heart, kidneys, liver, lungs, pituitary gland, arteries, and sympathetic nervous system that regulates systemic blood pressure, fluid retention and volume, ion/electrolyte balance, and systemic vascular resistance. The canonical MAS signaling pathway at it relates to RAAS is depicted in FIG. 1A. Angiotensin-converting enzyme 2 (ACE2) is an enzyme that catalyzes the conversion of angiotensin II protein into angiotensin(1-7) heptapeptide. Human recombinant ACE2 GSK2586881 is one example of a synthetic ACE2 agent that may stimulate MAS receptor activity in vivo. ACE2 activators are classes of compounds that promote or enhance ACE2 activity. Examples of ACE2 activators include xanthenone (XNT) and diminazene aceturate (DIZE). An ACE inhibitor (ACE1) is any of a class of agents that inhibit angiotensin-converting enzyme (ACE), which in turn decreases formation of angiotensin II. Examples of ACEIs include enazepril (Lotensin™); captopril (Capoten™); enalapril (Vasotec™, Epaned™, Lexxel™); fosinopril (Monopril™); lisinopril (Prinivil™ Zestril™, Qbrelis™); moexipril (Univasc™); perindopril (Aceon™); quinapril (Accupril™); ramipril (Altace™); and trandolapril (Mavik™).

For purposes of the present disclosure, a "MAS receptor modulator" means an agent that alters the biochemical activity of MAS receptor, for example, by increasing its binding affinity to an agonist or antagonist, decreasing its binding affinity to an agonist or antagonist, increasing the steric availability of MAS receptor to a binding agent, increasing or decreasing the cell-surface availability of MAS receptor; deceasing the steric availability of MAS receptor to a binding agent, or any combination thereof.

As used herein, a "MAS receptor agonist" or "MAS agonist" means an agent that activates the biochemical activity of the MAS receptor. Non-limiting examples of MAS receptor agonists are described herein.

The prefix "$C_{u-v}$" or "$C_u-C_v$" indicates that the following group has from u to v carbon atoms. For example, "$C_{1-6}$ alkyl" or "$C_1-C_6$ alkyl" or "$(C_1-C_6)$-alkyl" indicates that the alkyl group has from 1 to 6 carbon atoms.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —$CH(CH_3)CH_2CH_3$), isobutyl (i.e., —$CH_2CH(CH_3)_2$), and tert-butyl (i.e., —$C(CH_3)_3$); and "propyl" includes n-propyl (i.e., —$(CH_2)_2CH_3$) and isopropyl (i.e., —$CH(CH_3)_2$).

"Alkenyl" refers to an alkyl group containing at least one (e.g., 1-3, or 1) carbon-carbon double bond and having from 2 to 20 carbon atoms (i.e., $C_{2-20}$ alkenyl), 2 to 12 carbon atoms (i.e., $C_{2-12}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one (e.g., 1-3, or 1) carbon-carbon triple bond and having from 2 to 20 carbon atoms (i.e., $C_{2-20}$ alkynyl), 2 to 12 carbon atoms (i.e., $C_{2-12}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy, and 1,2-dimethylbutoxy.

"Acyl" refers to a group —$C(O)R^y$, wherein $R^y$ is hydrogen, alkyl, alkenyl, alkynyl, cycloalkyl, heterocyclyl, aryl, heteroalkyl, or heteroaryl; each of which may be optionally substituted, as defined herein. Examples of acyl include, e.g., formyl, acetyl, cyclohexylcarbonyl, cyclohexylmethylcarbonyl, and benzoyl.

"Amido" refers to both a "C-amido" group which refers to the group —$C(O)NR^yR^z$ and an "N-amido" group which refers to the group —$NR^yC(O)R^z$, wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein, or $R^y$ and $R^z$ are taken together to form a cycloalkyl or heterocyclyl; each of which may be optionally substituted, as defined herein.

"Amino" refers to the group —$NR^yR^z$ wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl, and anthryl. Aryl, however, does not encompass or overlap in any way with heteroaryl defined below. If one or more aryl groups are fused with a heteroaryl, the resulting ring system is heteroaryl regardless of point of attachment. If one or more aryl groups are fused with a heterocyclyl, the resulting ring system is heterocyclyl regardless of point of attachment. If one or more aryl groups are fused with a cycloalkyl, the resulting ring system is cycloalkyl regardless of point of attachment.

"Aryloxy" refers to "aryl-O—."

"Carboxy" refers to —$CO_2H$.

"Carboxyalkyl" refers to an alkyl group as defined above, wherein one or more (e.g., 1 to 6 or 1 to 3) hydrogen atoms are replaced by a carboxy group.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_{3-20}$ cycloalkyl), 3 to 14 ring carbon atoms (i.e., $C_{3-14}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl, and cyclooctyl.

Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl, and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" or "heterocycle" refers to a saturated or partially unsaturated cyclic alkyl group, with one or more ring heteroatoms independently selected from nitrogen, oxygen, and sulfur. The term "heterocyclyl" includes heterocycloalkenyl groups (i.e., the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro, and may comprise one or more (e.g., 1 to 3) oxo (=O) or N-oxide (—O⁻) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to a cycloalkyl, an aryl, or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur, or oxygen. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), thiomorpholinyl, thiamorpholinyl, 1-oxo-thiomorpholinyl, and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as oxabicyclo[2.2.2]octanyl, 2-oxa-7-azaspiro[3.5]nonanyl, 2-oxa-6-azaspiro[3.4]octanyl, and 6-oxa-1-azaspiro[3.3]heptanyl.

Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system.

"Halogen" or "halo" refers to atoms occupying group VIIA of the periodic table, such as fluoro, chloro, bromo, or iodo.

"Hydroxyalkyl" refers to an alkyl group as defined above, wherein one or more (e.g., 1 to 6 or 1 to 3) hydrogen atoms are replaced by a hydroxy group.

The following compounds and pharmaceutical compositions thereof are useful for the purposes described herein.

5-Formyl-4-methoxy-2-phenyl-1-[[4-[2-(ethylaminocarbonylsulfonamido)-5-isobutyl-3-thienyl]phenyl]methyl]imidazole is a chemical compound of the formula:

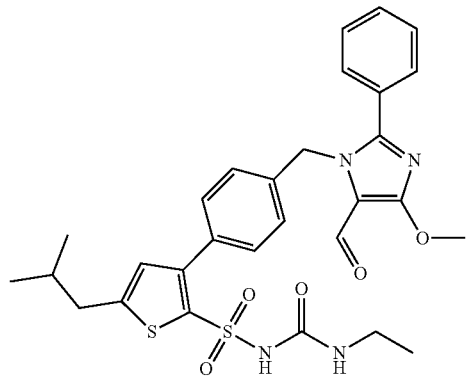 [SMILES: CCNC(=O)NS(=O)(=O)c1sc(CC(C)C)cc1-c1ccc(Cn2c(-c3ccccc3)nc(OC)c2C=O)cc1]

A 1-(p-thienylbenzyl)imidazole analogue may be any compound of Formula (I):

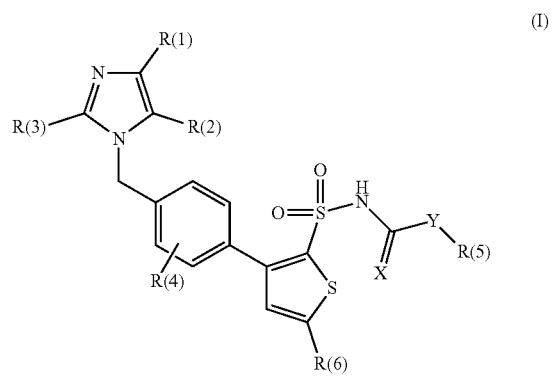

in which: R(1) is (1) halogen; (2) hydroxyl; (3) $(C_1-C_4)$-alkoxy; (4) $(C_1-C_8)$-alkoxy, wherein 1 to 6 carbon atoms are replaced by the heteroatoms O, S, or NH, (5) $(C_1-C_4)$-alkoxy, substituted by a saturated cyclic ether; (6) O—$(C_1-C_4)$-alkenyl; (7) O—$(C_1-C_4)$-alkylaryl; or (8) phenoxy, unsubstituted or substituted by a substituent selected from halogen, $(C_1-C_3)$-alkyl, $(C_1-C_3)$-alkoxy, and trifluoromethyl; R(2) is (1) CHO; R(3) is (1) $(C_1-C_4)$-alkyl; or (2) aryl; R(4) is (1) hydrogen; (2) halogen; or (3) $(C_1-C_4)$-alkyl; X is (1) oxygen; or (2) sulfur; Y is (1) oxygen; or (2) —NH—; R(5) is (1) hydrogen; (2) $(C_1-C_6)$-alkyl; or (3) $(C_1-C_4)$-alkylaryl; where R(5) can only be hydrogen if Y has the meaning mentioned under (2); and R(6) is (1) $(C_1-C_5)$-alkyl; in any stereoisomeric form or mixture thereof in any ratio, or a physiologically acceptable salt thereof.

Analogues of a 1-(p-thienylbenzyl)imidazole may also comprise any compound of Formula (II):

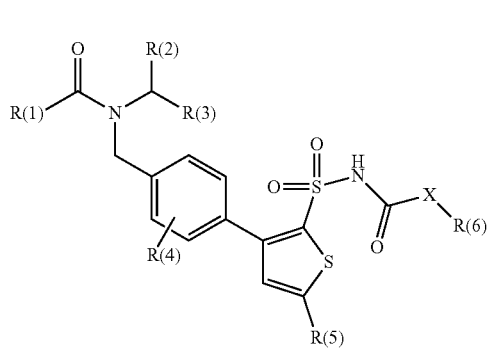

in which: R(1) is chosen from among 1. $(C_1-C_5)$-alkyl, unsubstituted or substituted by a radical chosen from among $NH_2$, halogen, O—$(C_1-C_3)$-alkyl, CO—O—$(C_1-C_3)$-alkyl and $CO_2H$; 2. $(C_3-C_8)$-cycloalkyl; 3. $(C_1-C_3)$-alkyl-$(C_3-C_8)$-cycloalkyl; 4. $(C_6-C_{10})$-aryl, unsubstituted or substituted by a radical chosen from halogen and O—$(C_1-C_3)$-alkyl; 5. $(C_1-C_3)$-alkyl-$(C_6-C_{10})$-aryl, where the aryl radical is unsubstituted or substituted by a radical chosen from halogen and O—$(C_1-C_3)$-alkyl; 6. $(C_3-C_5)$-heteroaryl; and 7. $(C_1-C_3)$-alkyl-$(C_1-C_5)$-heteroaryl; R(2) is chosen from among hydrogen; 2. $(C_1-C_6)$-alkyl, unsubstituted or substituted by a radical chosen from halogen and O—$(C_1-C_3)$-alkyl; 3. $(C_3-C_8)$-cycloalkyl; 4. $(C_1-C_3)$-alkyl-$(C_3-C_8)$-cycloalkyl; 5. $(C_6-C_{10})$-aryl, unsubstituted or substituted by a radical chosen from among halogen, O—$(C_1-C_3)$-alkyl and CO—O—$(C_1-C_3)$-alkyl; and 6. $(C_1-C_3)$-alkyl-$(C_6-C_{10})$-aryl, unsubstituted or substituted by a radical chosen from halogen and O—$(C_1-C_3)$-alkyl; R(3) is chosen from among 1. hydrogen; 2. COOH; and 3. COO—$(C_1-C_4)$-alkyl; R(4) is chosen from among 1. hydrogen; 2. halogen; and 3. $(C_1-C_4)$-alkyl; R(5) is chosen from 1. hydrogen, and 2. $(C_1-C_6)$-alkyl; R(6) is chosen from among 1. hydrogen; 2. $(C_1-C_6)$-alkyl; 3. $(C_1-C_3)$-alkyl-$(C_3-C_5)$-cycloalkyl; and 4. $(C_2-C_6)$-alkenyl; X is chosen from 1. oxygen, and 2. NH; in all the stereoisomeric forms thereof, and mixtures thereof in all ratios, and the physiologically tolerated salts thereof. In some embodiments, 1-(p-thienylbenzyl)imidazole analogues are those in which R(1) is(1) chlorine; (2) hydroxyl; (3) methoxy, ethoxy, or propyloxy; (4) methoxyethoxy or methoxypropoxy; (5) allyloxy; or (6) phenoxy; R(4) is(1) hydrogen; or (2) chlorine; R(5) is (1) hydrogen; or (2) $(C_1-C_4)$-alkyl; R(6) is (1) n-propyl or 2-isobutyl; and the other radicals are as defined above, in any stereoisomeric form or mixture thereof in any ratio, or a physiologically tolerable salt thereof.

In some embodiments, analogues of a 1-(p-thienylbenzyl) imidazole are compounds of formula (a):

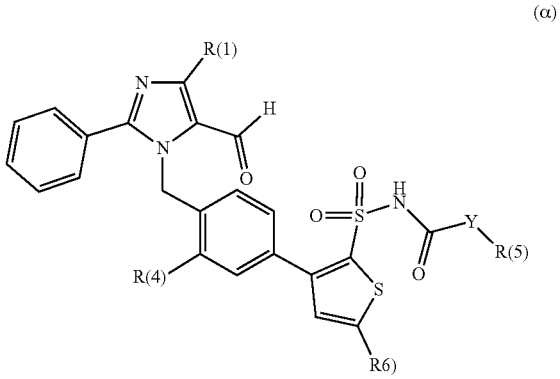

in which the radicals R(1) is (1) chlorine; (2) hydroxyl; (3) methoxy, ethoxy, or propyloxy; (4) methoxyethoxy or methoxypropoxy; (5) allyloxy; or (6) phenoxy; R(4) is (1) hydrogen; or (2) chlorine; R(5) is (1) hydrogen; or (2) $(C_1-C_4)$-alkyl; R(6) is (1) n-propyl or 2-isobutyl;, and Y is oxygen or NH.

Exemplary 1-(p-thienylbenzyl)imidazole analogues may include, but are not limited to: 4-chloro-5-formyl-2-phenyl-1-[[4-[2-(n-butyloxycarbonylsulfonamido)-5-isobutyl-3-thienyl]phenyl]methyl]imidazole, the structure of which is provided below:

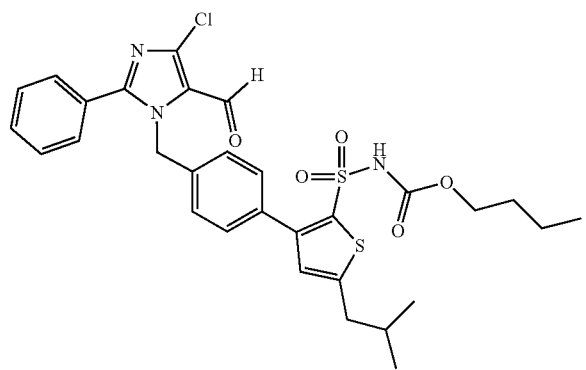

5-formyl-4-methoxy-2-phenyl-1-[[4-[2-(n-butyloxycarbonylsulfonamido)-5-isobutyl-3 thienyl]phenyl]methyl]imidazole:

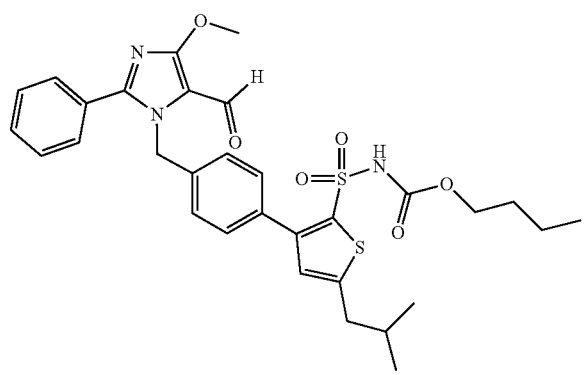 [SMILES: CCCCOC(=O)NS(=O)(=O)c1sc(CC(C)C)cc1-c1ccc(Cn2c(-c3ccccc3)nc(OC)c2C=O)cc1]

23

5-formyl-4-methoxy-2-phenyl-1-[[4-[2-(n-propyloxycarbonylsulfonamido)-5-isobutyl-3-thienyl]phenyl]methyl]imidazole, the structure for which is provided below:

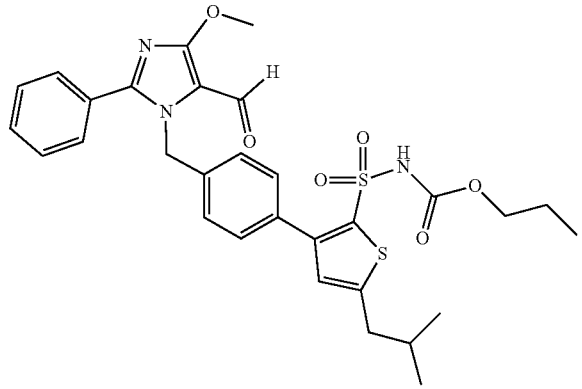 [SMILES: CCCOC(=O)NS(=O)(=O)c1sc(CC(C)C)cc1-c1ccc(Cn2c(-c3ccccc3)nc(OC)c2C=O)cc1]

5-formyl-4-methoxy-2-phenyl-1-[[4-[2-(ethoxycarbonylsulfonamido)-5-isobutyl-3-thienyl]phenyl]methyl]imidazole:

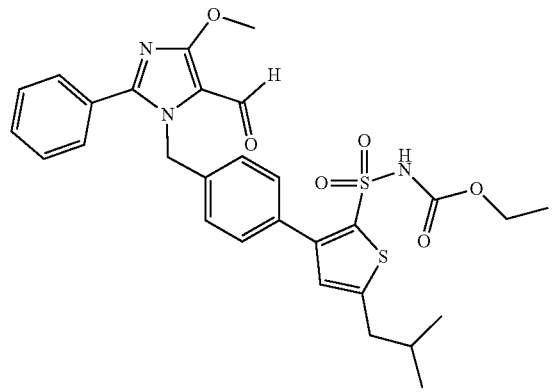 [SMILES: CCOC(=O)NS(=O)(=O)c1sc(CC(C)C)cc1-c1ccc(Cn2c(-c3ccccc3)nc(OC)c2C=O)cc1]

5-formyl-4-methoxy-2-phenyl-1-[[4-[2-(methoxycarbonylsulfonamido)-5-isobutyl-3-thienyl]phenyl]methyl]imidazole:

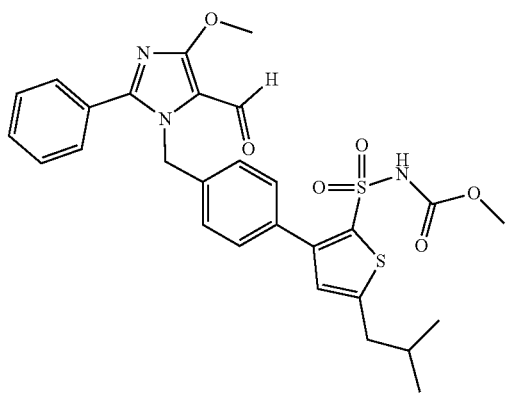 [SMILES: COC(=O)NS(=O)(=O)c1sc(CC(C)C)cc1-c1ccc(Cn2c(-c3ccccc3)nc(OC)c2C=O)cc1]

24

5-formyl-4-methoxy-2-phenyl-1-[[4-[2-(n-butylaminocarbonylsulfonamido)-5-isobutyl-3-thienyl]phenyl]methyl]imidazole:

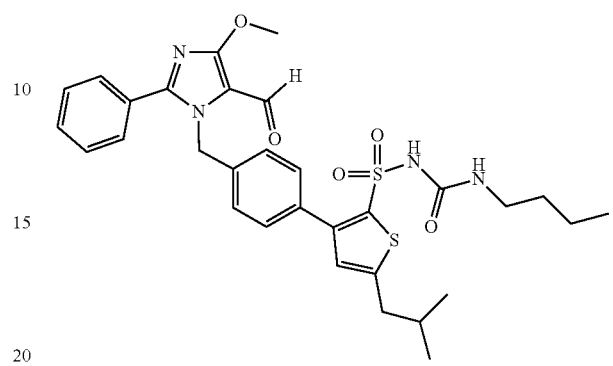

5-formyl-4-methoxy-2-phenyl-1-[[4-[2-(methylaminocarbonylsulfonamido)-5-isobutyl-3-thienyl]phenyl]methyl]imidazole:

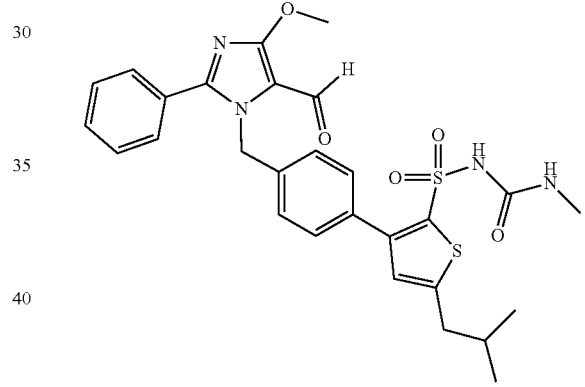

5-formyl-4-methoxyethoxy-2-phenyl-1-[[4-[2-(n-butyloxycarbonylsulfonamido)-5-isobutyl-3-thienyl]phenyl]methyl]imidazole:

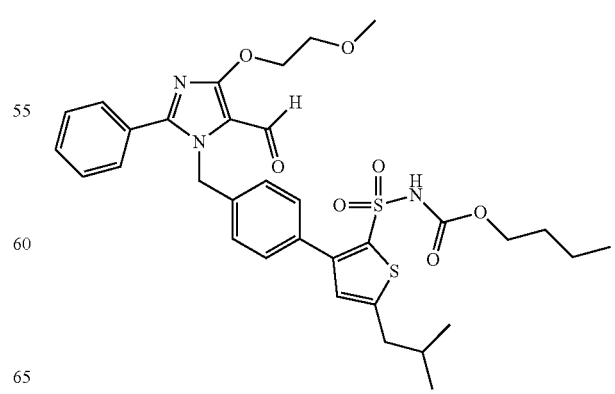

5-formyl-4-methoxy-2-phenyl-1-[[4-[2-(n-butyloxycarbonylsulfonamido)-5-isobutyl-3-thienyl]-2-chlorophenyl]methyl]imidazole:

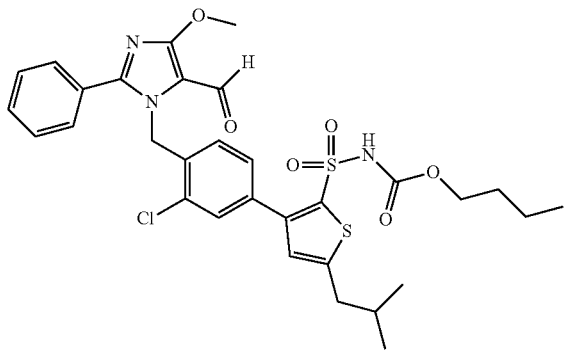 [SMILES: CCCCOC(=O)NS(=O)(=O)c1sc(CC(C)C)cc1-c1ccc(Cn2c(-c3ccccc3)nc(OC)c2C=O)c(Cl)c1]

5-formyl-4-methoxy-2-phenyl-1-[[4-[2-(n-butyloxycarbonylsulfonamido)-5-isobutyl-3-thienyl]-2-chlorophenyl]methyl]imidazole:

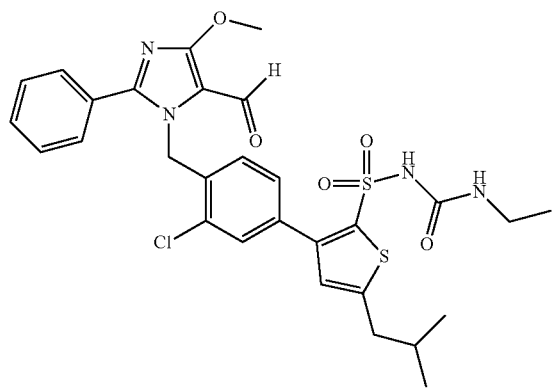 [SMILES: CCNC(=O)NS(=O)(=O)c1sc(CC(C)C)cc1-c1ccc(Cn2c(-c3ccccc3)nc(OC)c2C=O)c(Cl)c1]

4-chloro-5-formyl-2-phenyl-1-[[4-[2-(n-butyloxycarbonylsulfonamido)-5-n-propyl-3-thienyl]phenyl]methyl]imidazole:

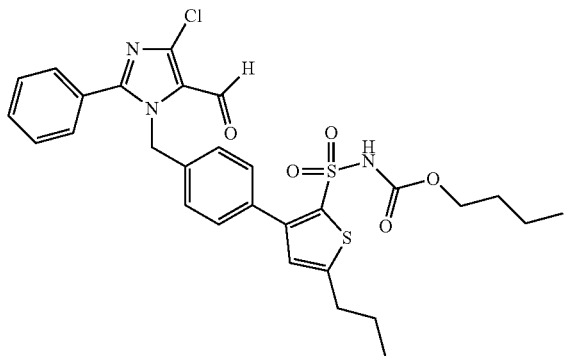 [SMILES: CCCCOC(=O)NS(=O)(=O)c1sc(CCC)cc1-c1ccc(Cn2c(-c3ccccc3)nc(Cl)c2C=O)cc1]

5-formyl-4-methoxy-2-phenyl-1-[[4-[2-(n-butyloxycarbonylsulfonamido)-5-n-propyl-3-thienyl]phenyl]methyl]imidazole:

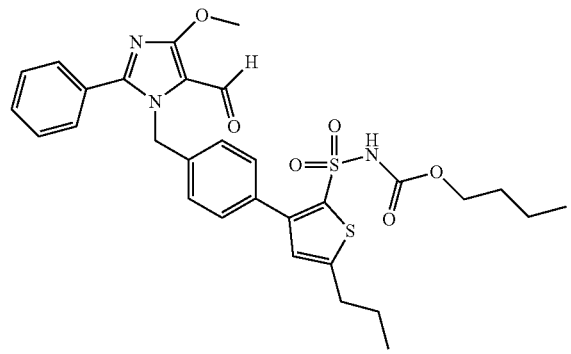 [SMILES: CCCCOC(=O)NS(=O)(=O)c1sc(CCC)cc1-c1ccc(Cn2c(-c3ccccc3)nc(OC)c2C=O)cc1]

5-formyl-4-methoxy-2-phenyl-1-[[4-[2-(methoxycarbonylsulfonamido)-5-n-propyl-3-thienyl]phenyl]methyl]imidazole:

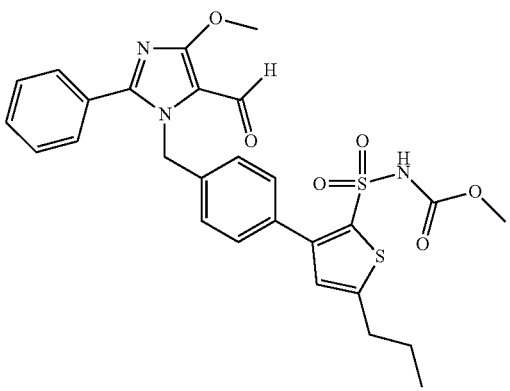 [SMILES: CCCc1cc(-c2ccc(Cn3c(-c4ccccc4)nc(OC)c3C=O)cc2)c(S(=O)(=O)NC(=O)OC)s1]

5-formyl-4-methoxy-2-phenyl-1-[[4-[2-(n-butylaminocarbonylsulfonamido)-5-n-proyl-3-thienyl]phenyl]methyl]imidazole:

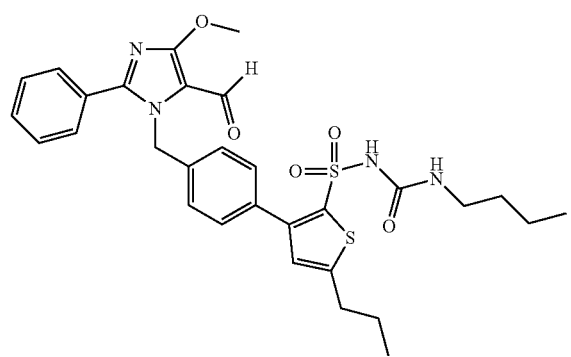 [SMILES: CCCCNC(=O)NS(=O)(=O)c1sc(CCC)cc1-c1ccc(Cn2c(-c3ccccc3)nc(OC)c2C=O)cc1]

5-formyl-4-methoxy-2-phenyl-1-[[4-[2-(methylaminocarbonylsulfonamido)-5-n-propyl-3-thienyl]phenyl]methyl]imidazole:

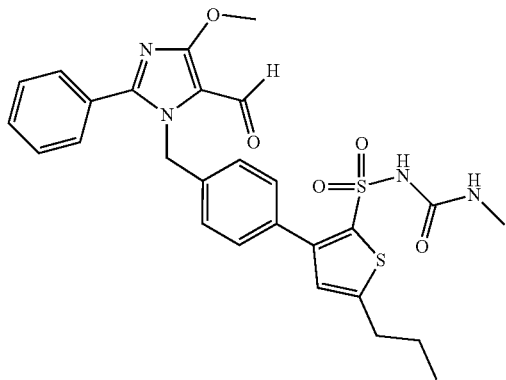 [SMILES: CCCc1cc(-c2ccc(Cn3c(-c4ccccc4)nc(OC)c3C=O)cc2)c(S(=O)(=O)NC(=O)NC)s1]

5-formyl-4-methoxy-2-phenyl-1-[[4-[2-(ethylaminocarbonylsulfonamido)-5-isobutyl-3-thienyl]phenyl]methyl]imidazole sodium salt:

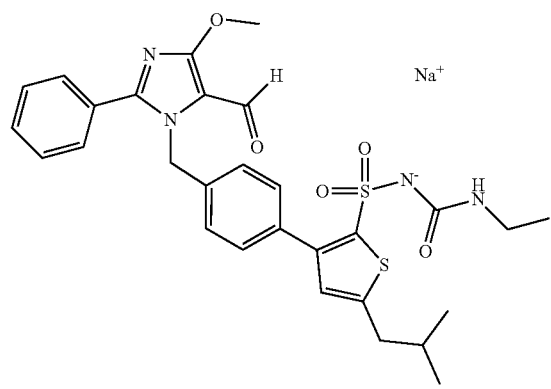 [SMILES: CCNC(=O)[N-]S(=O)(=O)c1sc(CC(C)C)cc1-c1ccc(Cn2c(-c3ccccc3)nc(OC)c2C=O)cc1 ; [Na+]]

5-formyl-4-methoxy-2-phenyl-1-[[4-[2-(ethylaminocarbonylsulfonamido)-5-isobutyl-3-thienyl]phenyl]methyl]imidazole L-lysine salt:

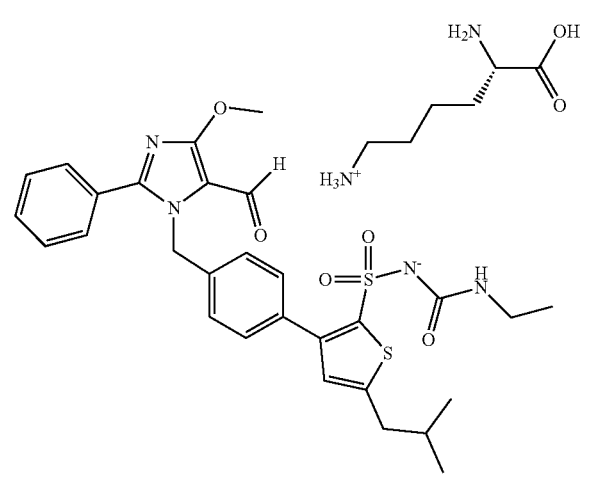 [SMILES: CCNC(=O)[N-]S(=O)(=O)c1sc(CC(C)C)cc1-c1ccc(Cn2c(-c3ccccc3)nc(OC)c2C=O)cc1 ; N[C@@H](CCCC[NH3+])C(=O)O]

5-formyl-4-methoxy-2-phenyl-1-[[4-[2-(ethylaminocarbonylsulfonamido)-5-isobutyl-3-thienyl]phenyl]methyl]imidazole tris(hydroxymethyl)aminomethane salt:

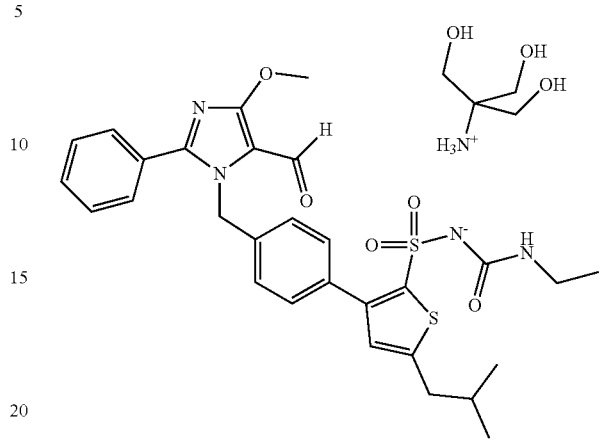

Compound 7 is a heterocyclic non-peptidic compound of the formula:

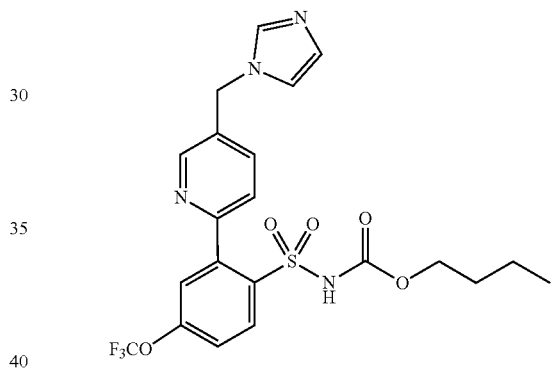

Heterocyclic non-peptidic angiotensin(1-7) mimetic compounds may be any compound of the formula (III):

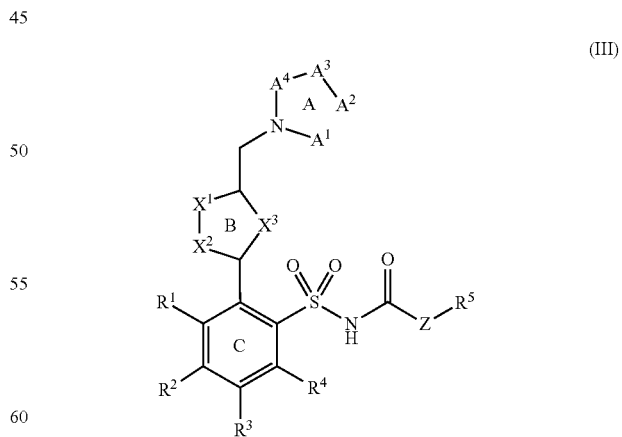

wherein: ring A is a five-membered or six-membered heteroaryl or heterocyclyl ring containing either a combination of two non-adjacent nitrogen or oxygen atoms, or a combination of three or four nitrogen or oxygen atoms; ring B is a five-membered or six-membered heteroaryl ring that contains at least one nitrogen atom; ring C is an optionally substituted aryl ring; $A^1$, $A^2$, $A^3$, $A^4$ are independently selected from a group consisting of =N—, —C(=O)—, —C($R^a$)=, =C($R^b$)—, —C($R^c$)($R^d$)—N($R^e$)—, —C($R^c$)($R^d$)—O—, or —[C($R^c$)($R^d$)]$_n$— with n being 1 or 2; $X^1$—$X^2$ is ($R^6$)C—N, N—C($R^6$), N—N, N—O, O—N, N—S or S—N; $X^3$ is ($R^7$)C=C($R^8$), O, S, or N($R^9$); Z is O, NH or a bond to $R^5$; $R^a$ and $R^b$ are independently selected from the group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^a$ and $R^b$ can also join to form a ring of up to 6 atoms; $R^c$ and $R^d$ are independently selected from a group consisting of hydrogen, alkyl, aryl, or heteroaryl, provided that $R^c$ and $R^d$ can also join to form a ring of up to 6 atoms; $R^e$ is hydrogen, alkyl, aryl, heteroaryl, acyl, alkoxyacyl, aminoacyl, dialkylaminoacyl, or dialkylaminoacyl; $R^1$, $R^3$, $R^4$, $R^6$, $R^7$, and $R^8$ are independently selected from a group consisting of hydrogen, alkyl, alkenyl, alkynyl, aryl, heteroaryl, arylmethyl, heteroarylmethyl, fluoro, bromo, iodo, cyano, hydroxy, amino, alkylamino, alkoxy, aryloxy, alkoxyalkyl, or aryloxyalkyl; $R^2$ is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl; $R^5$ is alkyl, aryl, heteroaryl, hydroxyalkyl, carboxyalkyl, alkoxyalkyl, or aryloxyalkyl; and $R^9$ is hydrogen, alkyl, aryl, heteroaryl, acyl, alkoxyacyl, aminoacyl, dialkylaminoacyl, or dialkylaminoacyl; or a pharmaceutically acceptable salt thereof.

In some embodiments of formula (III), $R^2$ is trifluoromethoxy. In some embodiments, Z is O or NH. In exemplary embodiments, ring A includes but is not limited to a ring selected from the group consisting of:

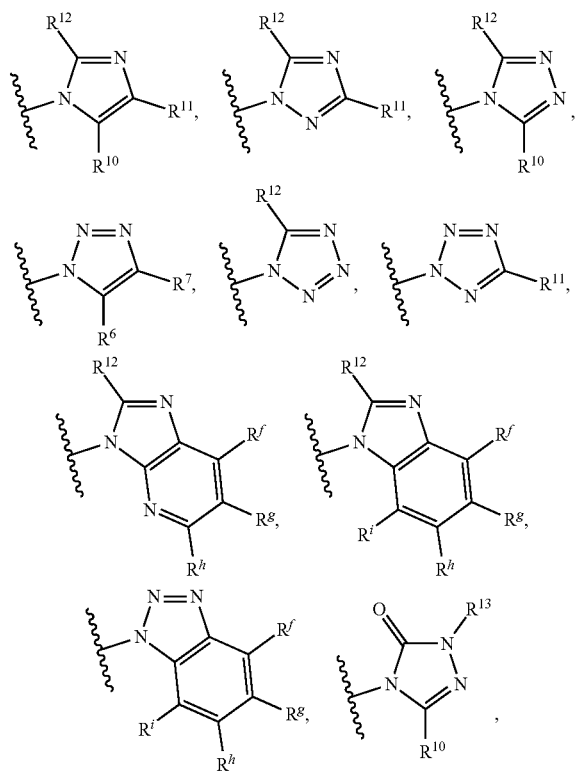

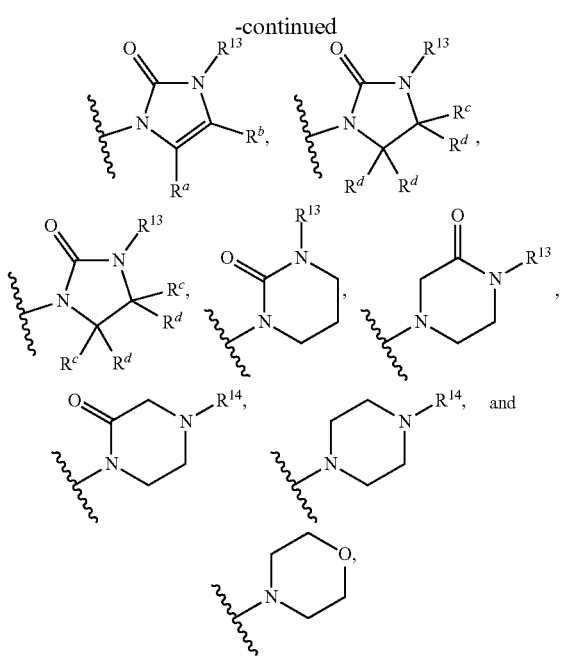

wherein, $R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring; $R^{12}$ is hydrogen, alkyl, alkenyl, alkynyl, aryl, heteroaryl, halo, hydroxy, hydroxyalkyl, alkoxyalkyl, alkoxy, aryloxy, or acylamido; $R^{13}$ is hydrogen, alkyl, aryl or heteroaryl; $R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, bromo, iodo, hydroxy, amino, alkylamino, alkoxy, aryloxy, alkoxyalkyl, or aryloxyalkyl.

In other exemplary embodiments, ring B includes but is not limited to a five- or six-membered heteroaryl ring selected from the group consisting of

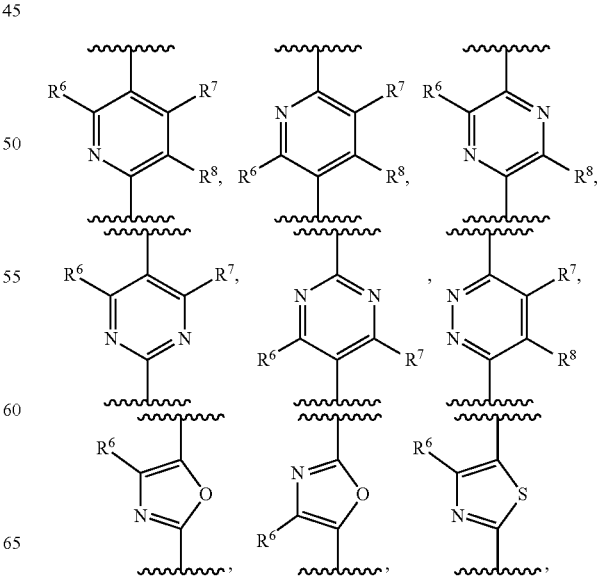

-continued
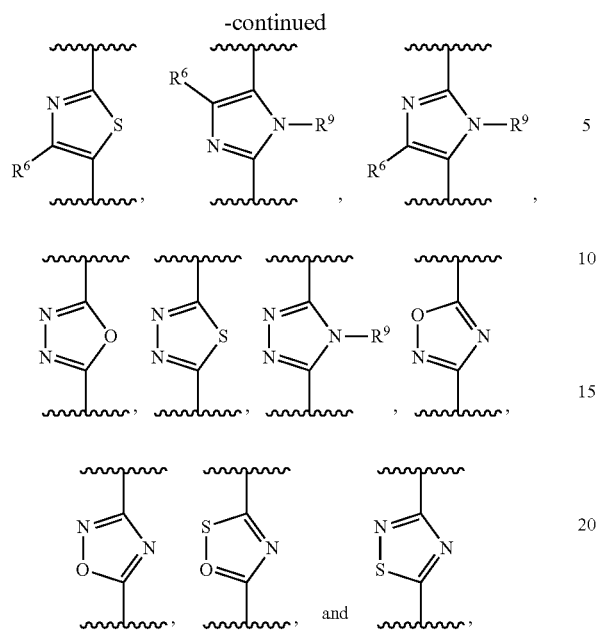
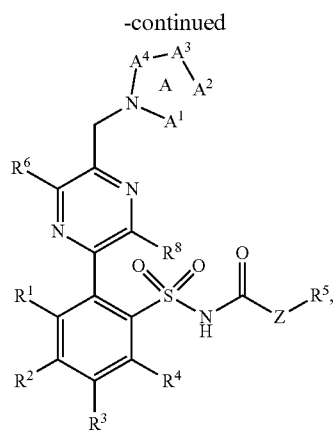
wherein groups R⁶, R⁷, R⁸, and R⁹ are defined as in the general formula (III), in the paragraphs above.
In some exemplary embodiments, the provided compounds have the general formula selected from a group consisting of:
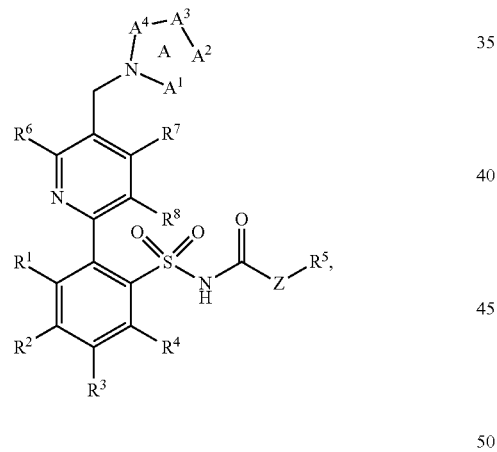
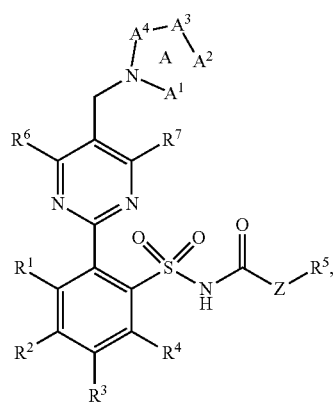
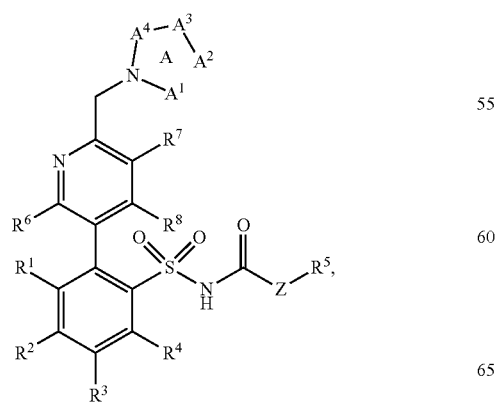
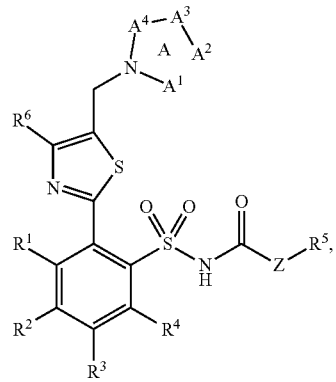
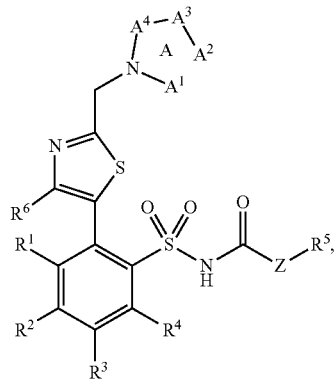

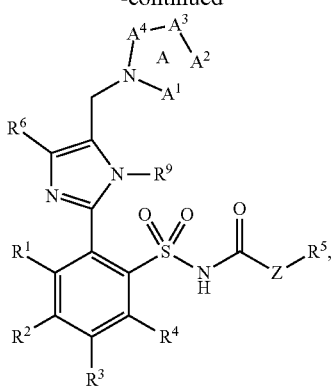
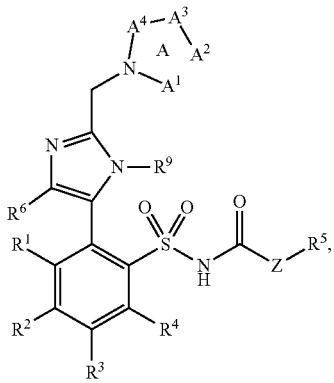
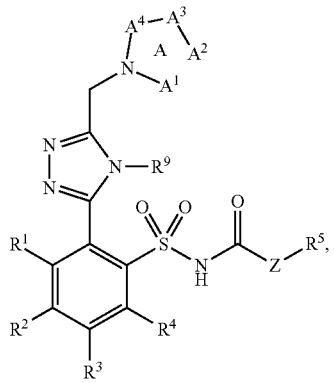
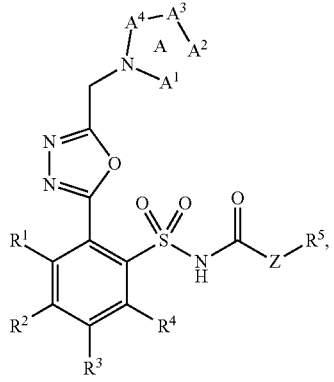
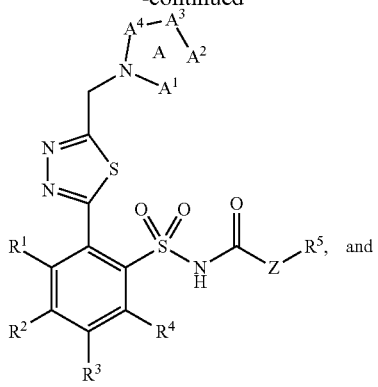
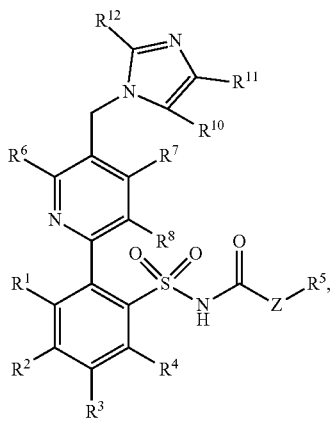
wherein groups $R^1$, $R^2$, $R^3$, $R^4$, $R^5$, $R^6$, $R^7$, $R^8$, $R^9$, $A^1$, $A^2$, $A^3$, $A^4$ and Z are defined as in general formula (III) in the paragraphs above.
In other exemplary embodiments, the provided compounds have the general formula selected from a group consisting of:

-continued
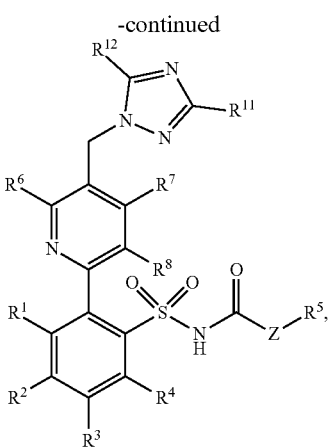
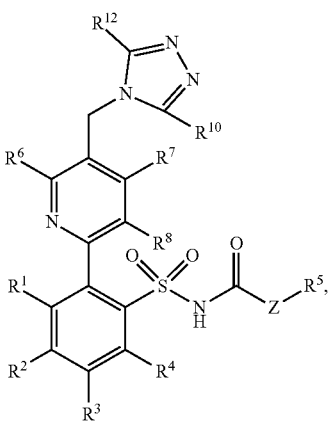
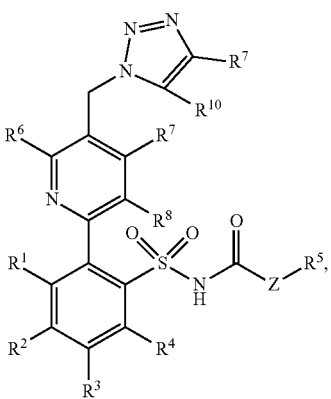
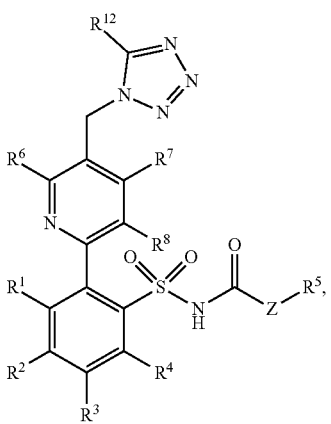
-continued
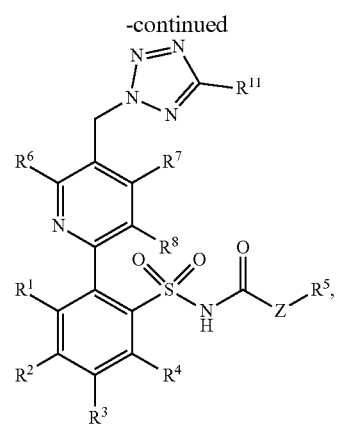
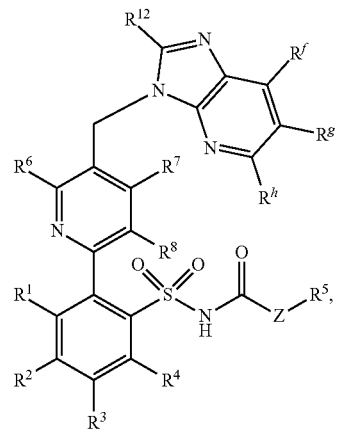
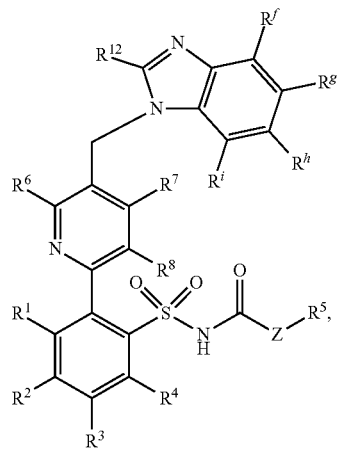
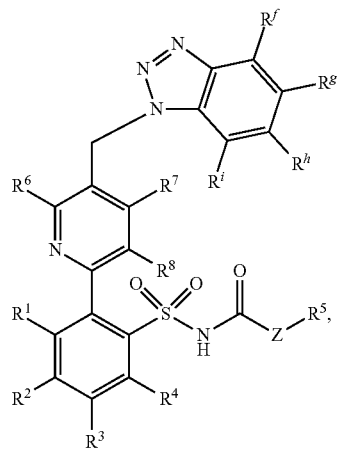

37
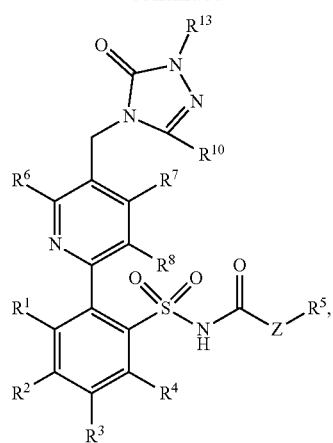
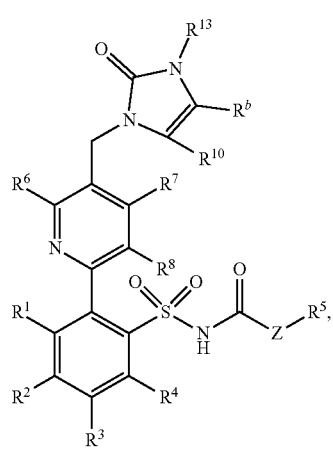
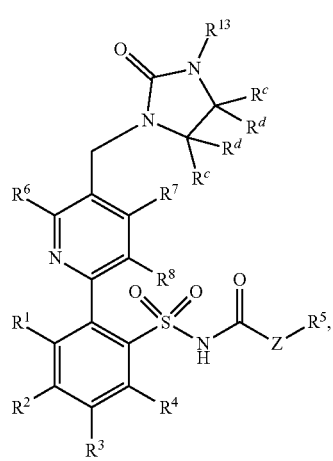
38
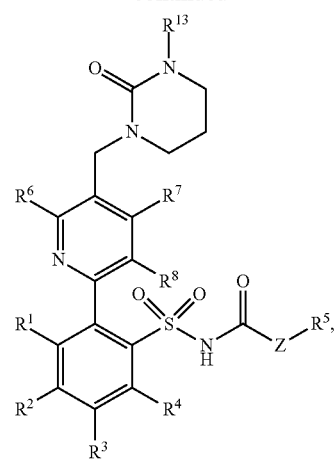
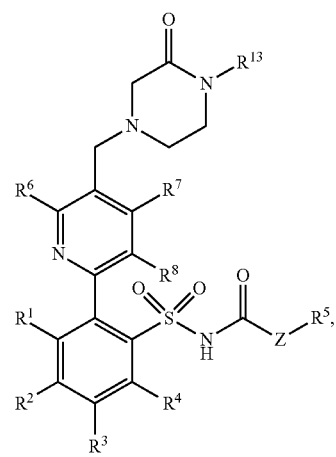
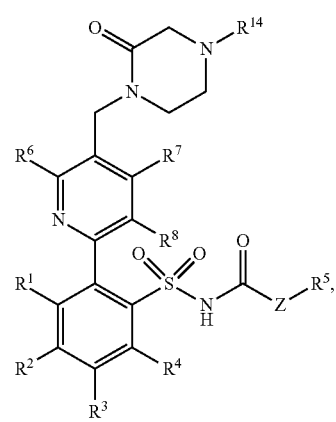

-continued

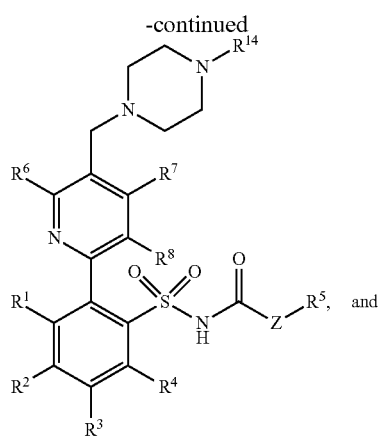

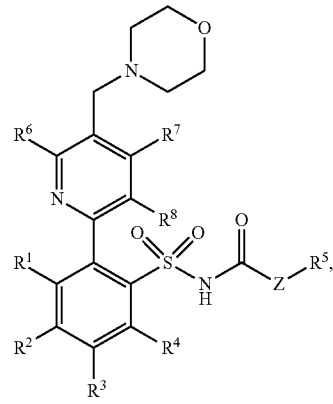

wherein:
R$^1$, R$^2$, R$^3$, R$^4$, R$^5$, R$^6$, R$^7$, R$^8$, R$^9$, R$^a$, R$^b$, R$^c$, R$^d$ and Z are defined as in general formula (III) in the paragraphs above;

R$^{10}$ and R$^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that R$^{10}$ and R$^{11}$ can also be joined to form a carbocyclic, heterocyclic, aryl or hetoaryl ring;

R$^{12}$ is hydrogen, alkyl, alkenyl, alkynyl, aryl, heteroaryl, halo, hydroxy, hydroxy alkyl alkoxyalkyl, alkoxy, aryloxv, or acylamido;

R$^{13}$ is hydrogen, alkyl, aryl or heteroaryl;

R$^{14}$ is hydrogen, alkyl, aryl, heteroaryl, acyl, alkoxyacyl, aminoacyl thalkylaminoacyl, or dialkylaninoacyl; and R$^f$, R$^g$, R$^h$, and R$^i$, are independently selected from a group consisting of hydrogen, alkyl, alkenyl, alkynyl, aryl, heteroaryl, arylmethyl, heteroarylmethyl, fluoro, bromo, iodo, hydroxy, amino, alkylamino, alkoxy, aryloxy, alkoxyalkyl, or aryloxyalkyl, Additional heterocyclic non-peptidic angiotensin(1-7) mimetic analogues may be found in the description of U.S. Pat. No. 10,301,298 B2, which is incorporated by reference in its entirety herein.

Compound 10 is a heterocyclic non-peptidic compound of formula:

Nle$^3$-A(1-7) (also called aclerastide, and which may alternatively styled Nle3-A(1-7)) is a peptide consisting of the amino acid sequence Asp-Arg-Nle-Tyr-Ile-His-Pro, of the formula:

20-Hydroxyecdysone (also commonly called ecdysterone, hydroxyecdysone, or "20E")) is a chemical compound of formula:

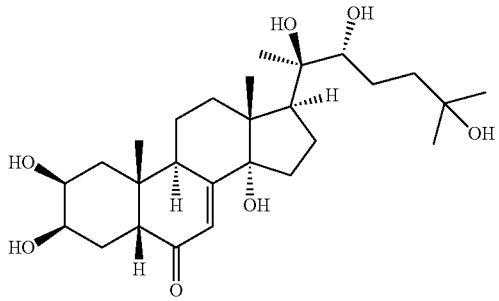

Analogues of 20-hydroxyecdysone are compounds of formula (IV):

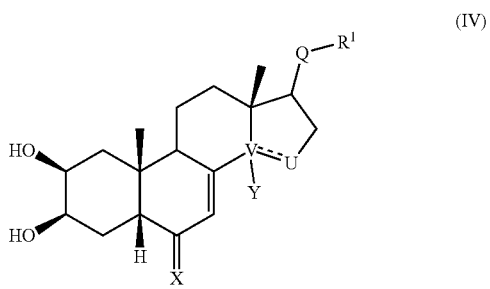

wherein: V—U is a single carbon-carbon bond and Y is a hydroxyl group or a hydrogen, or V—U is a C=C ethylene bond; X is an oxygen, Q is a carbonyl group; $R^1$ is chosen from: a group $(C_1-C_6)W(C_1-C_6)$; a group $(C_1-C_6)W(C_1-C_6)W(C_1-C_6)$; a group $(C_1-C_6)W(C_1-C_6)CO_2(C_1-C_6)$; a group $(C_1-C_6)A$, A representing a heterocycle optionally substituted by a group of the type OH, OMe, $(C_1-C_6)$, $N(C_1-C_6)$, $C_{O2}(C_1-C_6)$; a $CH_2Br$ group; W being a heteroatom chosen from N, O and S.

Angiotensin(1-7) is a seven-amino-acid peptide (i.e., heptapeptide) fragment of the protein angiotensin, consisting of the amino acid sequence Asp-Arg-Val-Tyr-Ile-His-Pro, of the formula:

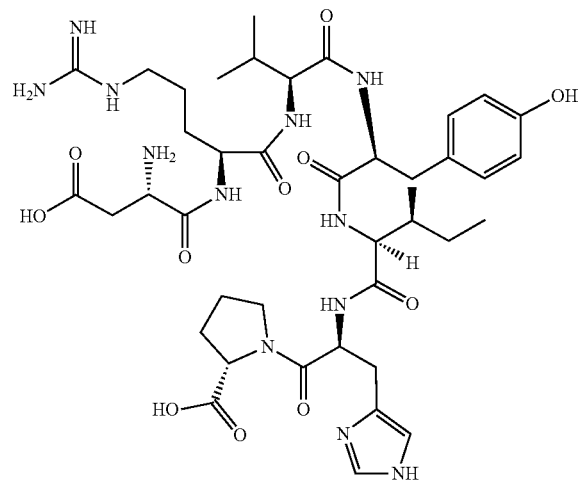 [SMILES: CC[C@H](C)[C@H](NC(=O)[C@H](Cc1ccc(O)cc1)NC(=O)[C@@H](NC(=O)[C@H](CCCNC(=N)N)NC(=O)[C@@H](N)CC(=O)O)C(C)C)C(=O)N[C@@H](Cc1c[nH]cn1)C(=O)N1CCC[C@H]1C(=O)O]

Angiotensin(1-7) (also styled "A(1-7)") comprises the amino acid sequence: H-Asp-Arg-Val-Tyr-Ile-His-Pro-OH.

Analogues of angiotensin(1-7) are any peptide having a sequence consisting of at least three contiguous amino acids of groups $R^1$—$R^8$ in the sequence of general formula (i) $R_1$—$R_2$—$R_3$—$R_4$—$R_5$—$R_6$—$R_7$—$R^8$ in which $R^1$ and $R_2$ together form a group of formula X $R_A$ $R_B$, wherein X is H or a one- to three-peptide group; $R_A$ is selected from Asp, Glu, Asn, Acpc, Ala, Me2Gly, Pro, Bet, Glu(NH_2), Gly, Asp(NH_2) and Suc, and glycosylated forms thereof; $R_B$ is selected from Arg, Lys, Ala, Orn, Ser(Ac), Sar, D-Arg, D-Lys, His, and glycosylated forms thereof; $R_3$ is selected from the group consisting of Val, Ala, Leu, Nle, Ile, Gly, Pro, Aib, Acpc, Lys, Tyr, and glycosylated forms thereof; $R_4$ is selected from the group consisting of Tyr, Tyr(PO_3)_2, Thr, Ser, Hse, Ala, and azaTyr, Tyr, Phe, and glycosylated forms thereof; $R_5$ is selected from the group consisting of Ile, Ala, Leu, Nle, Val, Gly, and glycosylated forms thereof; $R_6$ is His, Arg or 6-NH_2-Phe, Lys, and glycosylated forms thereof; $R_7$ is Pro, Ala, Gly, Ser, and glycosylated forms thereof; and $R_8$ is selected from the group consisting of Phe, Phe(Br), Ile, Tyr, Ser, Tr, Hyp, and glycosylated forms thereof. In some embodiments of formula(i), formula(i) sequences including $R_4$ as a terminal Tyr group are excluded.

In some embodiments, analogues of angiotensin(1-7) may include peptides and nonpeptide agents (i.e., peptidomimetics) that have the requisite biological activity. In some embodiments, combinations for $R_A$ and $R_B$ are Asp-Arg, Asp-Lys, Glu-Arg and Glu-Lys. Some embodiments of this class include the following: Arg-Val-Tyr-Ile-His-Pro-Phe; Val-Tyr-Ile-His-Pro-Phe; Asp-Arg-Val-Tyr-Ile-His-Pro; Arg-Val-Tyr-Ile-His-Pro; Val-Tyr-Ile-His-Pro; Ile-His-Pro-Phe; Asp-Arg-Val-Tyr-Ile-His; Asp-Arg-Val-Tyr-Ile; Asp-Arg-Val-Tyr; and Asp-Arg-Val. Some embodiments include: Arg-Nle-Tyr-Ile-His-Pro-Phe and Arg-Val-Tyr-Nle-His-Pro-Phe. In some embodiments, provided is a peptide having the sequence Asp-Arg-Pro-Tyr-Ile-His-Pro-Phe; His-Pro-Phe; and Tyr-Ile-His-Pro-Phe.

A class of analogues of angiotensin(1-7) may be those with the following general structure: $R_1$-Arg-$R_2$—$R_3$—$R_4$-His-Pro-$R_5$, wherein $R^1$ is selected from the group consisting of H and Asp; $R_2$ is selected from the group consisting of Val and Pro; $R_3$ is selected from the group consisting of Tyr and Tyr(PO_3)_2; $R_4$ is selected from the group consisting of Ala, Ile, Leu, and Nle; and $R_5$ is Phe, Ile, or is absent.

In any embodiment of the present disclosure, an analogue of angiotensin(1-7) may also comprise a sequence of the general formula (ii) Ala_1-$R_2$—$R_3$—$R_4$—$R_5$—$R_6$—$R_7$ wherein $R_2$ is selected from Arg, Lys, Ala, Cit, Orn, Ser(Ac), Sar, D-Arg, and D-Lys; $R_3$ is selected from the group consisting of Val, Ala, Leu, Nle, Ile, Gly, Pro, Aib, Acpc, Lys, and Tyr; $R_4$ is Ser, or forms a cyclic thioether with $R_7$; $R_5$ is selected from the group consisting of Ile, Ala, Leu, Nle, Val, and Gly; $R_6$ is His, Arg, 6-NH_2-Phe, Lys, and glycosylated forms thereof; and $R_7$ is Cys or forms a cyclic thioether with $R_4$.

A779 is a peptide MAS receptor antagonist (i.e., an inhibitor) of the amino acid sequence Asp-Arg-Val-Tyr-Ile-His-D-Ala (where D-Ala is the D-enantiomer of alanine). A779 may be used in MAS receptor inhibition experiments, competitive binding assays, or other purposes.

Abbreviations used herein for the canonical proteinogenic amino acids adhere to industry standards, and should be readily understood by persons having ordinary skill in the art. Amino acids abbreviated with the prefix D-refer to the D-enantiomer, but without any prefix shall be understood as referring to the L-enantiomer, unless indicated otherwise by context. As used herein, modified, uncommon, non-proteinogenic amino acids and other groups shall be abbreviated as follows: Aad=2-aminoadipic acid; bAad=3-aminoadipic acid; Acpc=1-aminocyclopropanecarboxylic acid; bAla=β-alanine (i.e., β-aminoproprionic acid); Abu=2-aminobutyric acid; 4Abu=4-aminobutyric acid (i.e., piperidinic acid); Acp=6-aminocaproic acid; Ahe=2-aminoheptanoic acid; Aib=2-aminoisobutyric acid; bAib=3-aminoisobutyric acid; Bet=1-carboxy-N,N,N-trimethylmethanaminium hydroxide inner salt (betaine); Apm=2-aminopimelic acid; Dbu=2,4-diaminobutyric acid; Des=desmosine; Dpm=2,2'-diaminoproprionic acid; Dpr=2,3-diaminoproprionic acid; EtGly=N-ethylglycine; EtAsn=N-ethylasparagine; Hse=homoserine (i.e., isothreonine); Hyl=hydroxylysine; aHyl=allo-hydroxylysine; 3Hyp=3-hydroxyproline; 4Hyp=4-hydroxyproline; Ide=isodesmosine; alle=allo-Isoleucine; MeGly=N-methylglycine (i.e., sarcosine); Me2Gly=dimethylglycine; MeIle=N-methylisoleucine; MeLys=6-N-methyllysine; MeVal=N-methylvaline; Nva=norvaline; Nle=norleucine; Orn=ornithine; Sar=sarcosine; Suc=succinic acid. Additionally, some alternative abbreviations for uncommon amino acids may be known to those having ordinary skill in the art, and may be readily understood from their context. For example, sometimes norleucine may be abbreviated as "nor-Leu" and homoserine may be abbreviated as "homoSer."

In some embodiments, an analogue of angiotensin(1-7) is A-1317 (wherein the amino acid L-arginine to the N-terminal of Ang(1-7)).

In some embodiments, the MAS receptor agonist is a compound of Formula (III).

In some embodiments, the MAS receptor agonist is selected from the group consisting of:
a heterocyclic non-peptidic angiotensin(1-7) mimetic or analogue thereof;
angiotensin(1-7) or an analogue thereof:
Nle$^3$-A(1-7) or an analogue thereof;
a 1-(p-thienylbenzyl)imidazole analogue; and
20-hydroxyecdysone or an analogue thereof.

In some embodiments, the MAS receptor agonist is selected from the group consisting of
Compound 7;
Compound 10;
Nle$^3$-A(1-7);
angiotensin(1-7);
the Ang-1-6-Ser-O-glycosylated analogue of angiotensin (1-7); and
5-formyl-4-methoxy-2-phenyl-1-[[4-[2-(ethylaminocarbonylsulfonamido)-5-isobutyl-3-thienyl]phenyl]methyl]imidazole.

In some embodiments, the MAS receptor agonist is Compound 7. In some embodiments, the MAS receptor agonist is Compound 10. In some embodiments, the MAS receptor agonist is Nle$^3$-A(1-7). In some embodiments, the MAS receptor agonist is angiotensin(1-7). In some embodiments, the MAS receptor agonist is 20-hydroxyecdysone or an analogue thereof. In some embodiments, the MAS receptor agonist is 5-formyl-4-methoxy-2-phenyl-1-[[4-[2-(ethylaminocarbonylsulfonamido)-5-isobutyl-3-thienyl]phenyl]methyl]imidazole.

Pharmaceutical Compositions

Provided herein are pharmaceutical compositions comprising a compound as described herein. In some embodiments, the pharmaceutical composition further comprises one or more pharmaceutically acceptable carriers, excipients and/or diluents.

In some embodiments, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present disclosure also includes "pharmaceutically acceptable salts" of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compound of the disclosure include the conventional non-toxic salts of the parent compound formed, for example, from non-toxic inorganic or organic acids. The pharmaceutically acceptable salts of the compound of the disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media, such as ether, ethyl acetate, ethanol, isopropanol, and acetonitrile, may be used.

The pharmaceutically acceptable salts of the compound of the disclosure can be also obtained by converting derivatives which possess tertiary amino groups into the corresponding quaternary ammonium salts in a manner known per se using quaternizing agents. Examples of suitable quaternizing agents are alkyl halides, such as methyl iodide, ethyl bromide, and n-propyl chloride, and also arylalkyl halides, such as benzyl chloride or 2-phenylethyl bromide. In some embodiments, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

Possible pharmaceutically acceptable salts are well known in the art. For example, S. M. Berge, et al. describe pharmaceutically acceptable salts in detail in J. Pharmaceutical Sciences, 66: 1-19, 1977; incorporated herein by reference.

Typically, a pharmaceutically acceptable salt form of a compound can be prepared in situ during the final isolation and purification of the compound, or separately by reacting the free base functionality with a suitable organic or inorganic acid. Examples of typical pharmaceutically acceptable, nontoxic acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods used in the art such as ion exchange.

Other pharmaceutically acceptable salts can include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and quaternary ammonium salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

This disclosure further includes derivatives of the compound of the disclosure. The term "derivatives" includes but is not limited to ether derivatives, acid derivatives, amide derivatives, ester derivatives and the like. In addition, this disclosure further includes hydrates or solvates of the compound of the disclosure. The term "hydrate" includes but is not limited to hemihydrate, monohydrate, dihydrate, trihydrate and the like.

This disclosure further includes metabolites of the compound of the disclosure. The term "metabolite" means any substance produced from another substance by metabolism or a metabolic process.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used herein includes both one and more than one such excipient.

"Pharmaceutically acceptable carriers" include any excipient which is nontoxic to the cell or subject being exposed thereto at the dosages and concentrations employed. The pharmaceutical composition may include one or additional therapeutic agents.

Pharmaceutically acceptable carriers include solvents, dispersion media, buffers, coatings, antibacterial and antifungal agents, wetting agents, preservatives, buggers, chelating agents, antioxidants, isotonic agents and absorption delaying agents.

Pharmaceutically acceptable carriers include water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN®, polyethylene glycol (PEG), and PLURONICS; isotonic agents such as sugars, polyalcohols such as mannitol and sorbitol, and sodium chloride; as well as combinations thereof. Antibacterial and antifungal agents include parabens, chlorobutanol, phenol, ascorbic acid, and thimerosal.

This disclosure further includes pharmaceutical compositions and pharmaceutical products of the compound of the disclosure. The terms "pharmaceutical composition" and "pharmaceutical product" means a composition suitable for pharmaceutical use (pharmaceutical composition), as defined herein. In some embodiments, as used herein, "pharmaceutical composition" also refers to therapeutically effective amounts of the compound of the disclosure together with suitable diluents, preservatives, solubilizers, emulsifiers, adjuvant and/or carriers.

In practice, the compounds of the disclosure, for example, represented by Formula (I), Formula (III), and other compounds or formulas as described herein, or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non aqueous liquid, as an oil in water emulsion, or as a water in oil liquid emulsion.

In addition to the common dosage forms set out above, the compounds as described herein, such as compounds represented by Formula (I) or (III) or other formulas as described herein, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Solid medicinal forms can comprise inert components and carrier substances, such as calcium carbonate, calcium phosphate, sodium phosphate, lactose, starch, mannitol, alginates, gelatine, guar gum, magnesium stearate, aluminum stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavorings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators. Examples of such additives are tartrate and citrate buffers, ethanol and sequestering agents (such as ethylenediaminetetraacetic acid and its nontoxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats, and solid high molecular weight polymers, such as polyethylene glycol.

Oily suspensions for parenteral or topical applications can be vegetable synthetic or semisynthetic oils, such as liquid fatty acid esters having in each case from 8 to 22 C atoms in the fatty acid chains, for example palmitic acid, lauric acid, tridecanoic acid, margaric acid, stearic acid, arachidic acid, myristic acid, behenic acid, pentadecanoic acid, linoleic acid, elaidic acid, brasidic acid, erucic acid or oleic acid, which are esterified with monohydric to trihydric alcohols having from 1 to 6 C atoms, such as methanol, ethanol, propanol, butanol, pentanol or their isomers, glycol or glycerol. Examples of such fatty acid esters are commercially available miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters, such as artificial ducktail gland fat, coconut fatty acid isopropyl ester, oleyl oleate, decyl oleate, ethyl lactate, dibutyl phthalate, diisopropyl adipate, polyol fatty acid esters, inter alia. Silicone oils of differing viscosity, or fatty alcohols, such as isotridecyl alcohol, 2-octyldodecanol, cetylstearyl alcohol or oleyl alcohol, or fatty acids, such as oleic acid, are also suitable. It is furthermore possible to use vegetable oils, such as castor oil, almond oil, olive oil, sesame oil, cotton seed oil, groundnut oil or soybean oil.

Suitable solvents, gelatinizing agents and solubilizers are water or watermiscible solvents. Examples of suitable substances are alcohols, such as ethanol or isopropyl alcohol, benzyl alcohol, 2-octyldodecanol, polyethylene glycols, phthalates, adipates, propylene glycol, glycerol, di- or tripropylene glycol, waxes, methyl cellosolve, cellosolve, esters, morpholines, dioxane, dimethyl sulphoxide, dimethylformamide, tetrahydrofuran, cyclohexanone, etc.

Mixtures of gelatinizing agents and film-forming agents are also perfectly possible. In this case, use is made, in particular, of ionic macromolecules such as sodium carboxymethyl cellulose, polyacrylic acid, polymethacrylic acid and their salts, sodium amylopectin semiglycolate, alginic acid or propylene glycol alginate as the sodium salt, gum arabic, xanthan gum, guar gum or carrageenan. The following can be used as additional formulation aids: glycerol, paraffin of differing viscosity, triethanolamine, collagen, allantoin and novantisolic acid. Use of surfactants, emulsifiers or wetting agents, for example of Na lauryl sulphate, fatty alcohol ether sulphates, di-Na—N-lauryl-β-iminodipropionate, polyethoxylated castor oil or sorbitan monooleate, sorbitan monostearate, polysorbates (e.g. Tween®), cetyl alcohol, lecithin, glycerol monostearate, polyoxyethylene stearate, alkylphenol polyglycol ethers, cetyltrimethylammonium chloride or mono-/dialkylpolyglycol ether orthophosphoric acid monoethanolamine salts can also be required for the formulation. Stabilizers, such as montmorillonites or colloidal silicic acids, for stabilizing emulsions or preventing the breakdown of active substances such as antioxidants, for example tocopherols or butylhydroxyanisole, or preservatives, such as p-hydroxybenzoic acid esters, can likewise be used for preparing the desired formulations.

Preparations for parenteral administration can be present in separate dose unit forms, such as ampoules or vials. Use is made of solutions of the active compound, such as aqueous solution and, in some embodiments, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

Inhalable preparations can present as powders, solutions or suspensions. In some embodiments, inhalable preparations are in the form of powders, e.g., as a mixture of the active ingredient with a suitable formulation aid such as lactose.

The preparations are produced, aliquoted and sealed under the customary antimicrobial and aseptic conditions.

Thus, the present disclosure further provides a pharmaceutical composition comprising a compound of the disclosure as described herein, or a pharmaceutically acceptable salt thereof, and a pharmaceutically acceptable carrier.

The term "carrier" refers to any chemical entity that can be incorporated into a composition containing an active agent (e.g., compounds described herein such as a compound of formula (I) or (III)) without interfering with the stability and/or activity of the agent. In some embodiments, the term "carrier" refers to a pharmaceutically acceptable carrier. An exemplary carrier herein is water.

Also comprehended by the disclosure are particulate compositions coated with polymers (e.g., poloxamers or poloxamines). Other embodiments of the compositions of the disclosure incorporate particulate forms protective coatings, protease inhibitors or permeation enhancers for various routes of administration, including parenteral, pulmonary, nasal and oral. In some embodiments, the pharmaceutical composition is administered parenterally, paracancerally, transmucosally, transdermally, intramuscularly, intravenously, intradermally, subcutaneously, intraperitoneally, intraventricularly, intravaginally, intracranially and intratumorally.

This disclosure further includes prodrugs of the compound of the disclosure. Compounds of the disclosure can also be prepared as prodrugs, for example pharmaceutically acceptable prodrugs. The terms "pro-drug" and "prodrug" are used interchangeably herein and may refer to any compound which releases an active parent drug in vivo. Since prodrugs are known to enhance numerous desirable qualities of pharmaceuticals (e.g., solubility, bioavailability, manufacturing, etc.) the compounds of the present disclosure can be delivered in prodrug form.

The term "prodrug" or "pro-drug" means a substance which can be converted in vivo into a biologically active agent by such reactions as hydrolysis, esterification, de-esterification, activation, salt formation and the like.

This disclosure further includes crystals of the compound of the disclosure. Further, this disclosure provides polymorphs of the compound of the disclosure. The term "crystal" means a substance in a crystalline state. The term "polymorph" refers to a particular crystalline state of a substance, having particular physical properties such as X-ray diffraction, IR spectra, melting point, and the like.

The pharmaceutical compositions of the disclosure may be formulated in a variety of ways, including for example, solid, semi-solid (e.g., cream, ointment, and gel), and liquid dosage forms, such as liquid solutions (e.g., topical lotion or spray), dispersions or suspensions, tablets, pills, powders, liposomes and suppositories. In some embodiments, the compositions are in the form of injectable or infusible solutions. The composition is in a form suitable for oral, intravenous, intraarterial, intramuscular, subcutaneous, parenteral, transmucosal, transdermal, or topical administration. The composition may be formulated as an immediate, controlled, extended or delayed release composition.

Pharmaceutical compositions suitable for use include sterile aqueous solutions (where water soluble) or dispersions and sterile powders for the extemporaneous preparation of sterile solutions or dispersions. It should be stable under the conditions of manufacture and storage and may be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

In some embodiments, the composition includes isotonic agents, for example, sugars, polyalcohols, such as mannitol, sorbitol, or sodium chloride. Prolonged absorption of injectable compositions can be brought about by including in the composition an agent which delays absorption, for example, aluminum monostearate and gelatin.

Sterile solutions can be prepared by incorporating the molecule, by itself or in combination with other active agents, in the required amount in an appropriate solvent with one or a combination of ingredients enumerated herein, as required, followed by filtered sterilization.

Generally, dispersions are prepared by incorporating the active compound into a sterile vehicle, which contains a basic dispersion medium and the required other ingredients from those enumerated above. In the case of sterile powders for the preparation of sterile injectable solutions, one method of preparation is vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art.

Further, the preparations may be packaged and sold in the form of a kit. Such articles of manufacture may have labels or package inserts indicating that the associated compositions are useful for treating a subject suffering a disease or condition as described herein.

Methods of Treatment and Uses

Effective doses of the compositions of the present disclosure, for treatment of conditions or diseases as described herein vary depending upon many different factors, including means of administration, target site, physiological state of the patient, whether the patient is human or an animal, other medications administered, and whether treatment is prophylactic or therapeutic. Usually, the patient is a human, but non-human organisms, including non-human mammals and birds, as well as transgenic organisms, can also be treated. Treatment dosages may be titrated using routine methods known to those of skill in the art to optimize safety and efficacy.

The pharmaceutical compositions of the disclosure may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, species, age, sex, and weight of the individual, and the ability of the molecule to elicit a desired response in the individual. A therapeutically effective amount is also one in which any toxic or detrimental effects of the molecule are outweighed by the therapeutically beneficial effects.

Also as used herein, in some embodiments, the terms "therapeutically effective amount" and "effective amount" of an agent refer to an amount sufficient to provide a therapeutic benefit in the treatment, prevention and/or management of a disease, disorder, or condition, e.g., to delay onset of or minimize (e.g., reduce the incidence, frequency, and/or magnitude of) one or more symptoms associated with the disease, disorder or condition to be treated. Those of ordinary skill in the art will appreciate that, a composition may be said to contain a "therapeutically effective amount" of an agent if it contains an amount that is effective when administered as a single dose within the context of a therapeutic regimen. In some embodiments, a therapeutically effective amount is an amount that, when administered as part of a dosing regimen, is statistically likely to delay onset of or minimize (reduce the incidence and/or magnitude of) one or more symptoms or side effects of a disease, disorder or condition. In some embodiments, a "therapeutically effective amount" is an amount that enhances therapeutic efficacy of another agent with which the composition is administered in combination.

In some embodiments, a therapeutically effective amount for administration to a human corresponds to a reference amount (e.g., a therapeutically effective amount in an animal model such as a mouse model) adjusted for body surface area of a human as compared with body surface area of the animal model, as is known in the art (see, for example Reagan-Shaw et al., "Dose translation from animal to human studies revisited," The FASEB Journal 22: 659-661 (2007), the entirety of which is herein incorporated by reference). In some embodiments, the reference therapeutically effective amount is an amount that is therapeutically effective in an animal model (e.g., in a mouse model). In some embodiments, the reference therapeutically effective amount is within the range of about 0.01 mg/kg to about 500 mg/kg. In some embodiments, the reference therapeutically effective amount is within the range of about 0.01 mg/kg to about 0.1 mg/kg. In some embodiments, the reference therapeutically effective amount is within the range of about 0.1 mg/kg to about 0.5 mg/kg. In some embodiments, the reference therapeutically effective amount is within the range of about 0.5 mg/kg to about 1 mg/kg. In some embodiments, the reference therapeutically effective amount is within the range of about 1 mg/kg to about 2.5 mg/kg. In some embodiments, the reference therapeutically effective amount is within the range of about 2.5 mg/kg to about 10 mg/kg. In some embodiments, the reference therapeutically effective amount is within the range of about 10 mg/kg to about 50 mg/kg. In some embodiments, the reference therapeutically effective amount is within the range of about 50 mg/kg to about 100 mg/kg. In some embodiments, the reference therapeutically effective amount is within the range of about 100 mg/kg to about 250 mg/kg. In some embodiments, the reference therapeutically effective amount is within the range of about 250 mg/kg to about 500 mg/kg.

As used herein, "modulating" refers to "stimulating" or "inhibiting" an activity of a molecular target or pathway. For example, a composition modulates the activity of a molecular target or pathway if it stimulates or inhibits the activity of the molecular target or pathway by at least 10%, by at least about 20%, by at least about 25%, by at least about 30%, by at least about 40%, by at least about 50%, by at least about 60%, by at least about 70%, by at least about 75%, by at least about 80%, by at least about 90%, by at least about 95%, by at least about 98%, or by about 99% or more relative to the activity of the molecular target or pathway under the same conditions but lacking only the presence of the composition. In another example, a composition modulates the activity of a molecular target or pathway if it stimulates or inhibits the activity of the molecular target or pathway by at least 2-fold, at least 5-fold, at least 10-fold, at least 20-fold, at least 50-fold, at least 100-fold relative to the activity of the molecular target or pathway under the same conditions but lacking only the presence of the composition. The activity of a molecular target or pathway may be measured by any reproducible means. The activity of a molecular target or pathway may be measured in vitro or in vivo. For example, the activity of a molecular target or pathway may be measured in vitro or in vivo by an appropriate assay known in the art measuring the activity. Control samples (untreated with the composition) can be assigned a relative activity value of 100%. A change in activity caused by the composition can be measured in the assays.

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

In one example, a single bolus may be administered. In another example, several divided doses may be administered over time. In yet another example, a dose may be proportionally reduced or increased as indicated by the exigencies of the therapeutic situation. Dosage unit form, as used herein, refers to physically discrete units suited as unitary dosages for treating mammalian subjects. Each unit may contain a predetermined quantity of active compound calculated to produce a desired therapeutic effect. In some embodiments, the dosage unit forms of the disclosure are dictated by and directly dependent on the unique characteristics of the active compound and the particular therapeutic or prophylactic effect to be achieved.

The composition of the disclosure may be administered only once, or it may be administered multiple times. For multiple dosages, the composition may be, for example, administered three times a day, twice a day, once a day, once every two days, twice a week, weekly, once every two weeks, or monthly.

As used herein, a compound "activates" an activity if the compound reduces the desired activity by at least 10% relative to the activity under the same conditions but lacking only the presence of the compound. The activity may be measured by any reproducible means. The activity may be measured in vitro or in vivo. In some embodiments, compounds used in the methods described herein activate MAS receptor activity by at least about 20%, by at least about 25%, by at least about 30%, by at least about 40%, by at least about 50%, by at least about 60%, by at least about 70%, by at least about 75%, by at least about 80%, by at least about 90%, by about 95%, by about 98%, or by about 99% or more.

In some embodiments, "stimulating mitophagy" refers to increasing mitophagy by at least 5%, by at least 10%, by at least about 20%, by at least about 25%, by at least about 30%, by at least about 40%, by at least about 50%, by at least about 60%, by at least about 70%, by at least about 75%, by at least about 80%, by at least about 90%, by at least about 95%, by at least about 98%, or by about 99% or more relative to the amount of mitophagy prior to the administration of an active agent (including but not limited to a MAS agonist) to a subject in need thereof.

As used herein, "mitophagy-stimulating amount" refers to an amount of an active agent (including but not limited to a MAS agonist) that increases mitophagy in a subject relative to the amount of mitophagy in a subject prior to administration of the active agent to the subject. In some embodiments, mitophagy is increased by about 5%, about 10%, about 15%, about 20%, about 25%, about 30%, about 35%, about 40%, about 50%, or more than about 50% as compared to the level of mitophagy in the subject prior to administration of the active agent to the subject.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

"Administration" to a subject is not limited to any particular delivery system and may include, without limitation, topical, transdermal, oral (for example, in capsules, suspensions or tablets), parenteral (including subcutaneous, intravenous, intramedullary, intraarticular, intramuscular, or intraperitoneal injection), or rectal. Administration to a subject may occur in a single dose or in repeat administrations, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, for example, Remington's Pharmaceutical Sciences, Mack Publishing Co.).

The term "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In some embodiments, the subject is a human patient. In some embodiments, the subject is male human or a female human.

The present disclosure further provides a method for preventing, treating or intervening in the recurrence of a disease or condition as described herein in a subject comprising administering to the subject a compound of the disclosure as described herein, or a pharmaceutically acceptable salt thereof, or a pharmaceutical composition thereof.

Treatment of a human or mammalian subject with a compound of the disclosure for any one of the conditions or diseases as described herein is typically achieved by administration of the compound in a pharmaceutical composition. The disclosure also encompasses a pharmaceutical composition that is comprised of a compound of Formula (I) in combination with a pharmaceutically acceptable carrier. Some embodiments provide for a pharmaceutical composition comprising a compound of Formula (III) and a pharmaceutically acceptable carrier.

Exemplary diseases that may be treated by stimulating mitochondrial turnover include mitochondrial diseases and non-mitochondrial diseases; vascular diseases; inflammatory diseases; renal diseases; ocular diseases; neurological diseases; neurodegenerative diseases.

Exemplary diseases shown to have a direct pathogenic link to mitochondrial turnover include Alzheimer's disease; amyotrophic lateral sclerosis (ALS); frontotemporal dementia; cardiovascular disease; Parkinson's disease; hematopoietic disorders; primary biliary cirrhosis/cholangitis (PBC); sepsis; and renal injury/damage.

Some embodiments provide for treating a disease or condition in a subject in need thereof, wherein the disease or condition exhibits a defect in mitochondrial function (including but not limited to accumulation of damaged mitochondria or impaired biogenesis) or a defect in mitophagy (such as blocked mitophagy or impaired mitophagy).

In some embodiments, the disease or condition (for example, a disease or condition that exhibits a defect in mitochondrial function or a defect in mitophagy) is MELAS, MERRF, Leigh Syndrome, progeria, Werner syndrome, Parkinson Juvenile type, late onset Parkinson's disease, early onset Parkinson's disease, or Rett Syndrome.

Some embodiments provide for treating a disease or condition in a subject in need thereof, wherein the disease or condition is a primary mitochondrial disease.

Some embodiments provide for treating a disease or condition in a subject in need thereof comprising administering to the subject an effective amount of a MAS receptor agonist or substance that triggers endogenous production of a MAS receptor agonist, wherein the disease or condition is:

Sjorgen's syndrome, progeria, Rett Syndrome, Down Syndrome; ataxia-telangiectasia; autosomal dominant optic atrophy; Barth syndrome; Charcot-Marie-Tooth disease; Charlevoix-Saguenay spastic ataxia; Cockayne syndrome; Danon disease; Fabry disease; Fanconi anemia; Friedrich's ataxia; Fuchs endothelial dystrophy; Gaucher disease; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Pearson syndrome; Pompe disease; rhabdomyosarcoma; schizophrenia; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof.

Some embodiments provide for treating a disease or condition in a subject in need thereof comprising administering to the subject an effective amount of a MAS receptor agonist or substance that triggers endogenous production of a MAS receptor agonist, wherein the disease or condition is:

Sjorgen's syndrome, progeria, Rett Syndrome, Down Syndrome; ataxia-telangiectasia; autosomal dominant optic atrophy; Barth syndrome; Charcot-Marie-Tooth disease; Charlevoix-Saguenay spastic ataxia; Cockayne syndrome; Danon disease; Fabry disease; Fanconi anemia; Friedrich's ataxia; Fuchs endothelial dystrophy; Gaucher disease; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Pearson syndrome; Pompe disease; rhabdomyosarcoma; schizophrenia; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof; and wherein the MAS receptor agonist is a compound of formula (III).

Some embodiments provide for treating a disease or condition in a subject in need thereof comprising administering to the subject an effective amount of a MAS receptor agonist or substance that triggers endogenous production of a MAS receptor agonist, wherein the disease or condition is:

Sjorgen's syndrome, progeria, Rett Syndrome, Down Syndrome; ataxia-telangiectasia; autosomal dominant optic atrophy; Barth syndrome; Charcot-Marie-Tooth disease; Charlevoix-Saguenay spastic ataxia; Cockayne syndrome; Danon disease; Fabry disease; Fanconi anemia; Friedrich's ataxia; Fuchs endothelial dystrophy; Gaucher disease; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Pearson syndrome; Pompe disease; rhabdomyosarcoma; schizophrenia; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof; and wherein the MAS receptor agonist is selected from the group consisting of: Compound 7; Compound 10; Nle$^3$-A(1-7); and angiotensin (1-7).

Some embodiments herein provide for methods for treating a disease or condition in a subject in need thereof comprising stimulating mitophagy in the subject by administering to the subject a mitophagy-stimulating amount of a MAS receptor agonist or substance that triggers endogenous production of a MAS receptor agonist.

It is contemplated that stimulation of mitophagy may improve mitochondria function and integrity. To assess mitochondrial function and integrity, it is contemplated that multiple parameters can be evaluated, such as morphological changes and total mass, mtDNA copy number and heteroplasmy shift, ROS production, electron chain function, and ATP synthase hydrolytic capability.

Mitochondrial morphology can be altered by the accumulation of damage as well as mitophagy induction. Specifically, when sustained depolarization of mitochondrial membrane potential occurs, mitochondria fission is needed to isolate the damaged mitochondria for degradation. Conversely, keeping the membrane potential will not allow this degradation and in healthy cells, elongated morphology is observed. In this way, mitochondrial morphology is a critical parameter to assess mitochondrial integrity. Morphology is assessed by confocal microscopy, and the images are quantified to measure mitochondrial size and shape (i.e., aspect ratio and circularity) according to methods known in the art. In the same way, mitochondrial mass can be assessed by total volume or area, but complementary methods may also be used. For that, total amount of integral proteins in cell lysates by western blotting and mtDNA copy number measurable by RT-PCR can be used to determine mitochondrial mass.

In cells with mtDNA mutations and deletions with variable heteroplasmy levels, the shift from disease causing alterations to wild-type DNA may be used to assess clearance by mitophagy. For that, evaluation of % heteroplasmy can be performed by methods known in the art, such as NGS sequencing, single-cell droplet digital PCR, or random mutation capture assay depending on the sensibility needed to detect heteroplasmy levels and the type of alteration (point mutation or deletion). Mitochondrial dysfunction can also increase ROS levels, creating an optimal environment for more structural and mtDNA damage. In some embodiments, evaluation of ROS levels by imaging cells loaded with mitochondrial targeted fluorescence tools like mitosox or ratiometric probes can be performed according to methods known in the art using microscopy.

Mitochondrial damage and mitophagy can also impact ETC function, and respirometry or specific complex activity may be evaluated in certain disease scenarios. More specifically, the capability of ATP synthase to produce ATP is a way to evaluate how healthy is the mitochondrial population. Under certain conditions, when the electrochemical proton gradient begins to fall, ATP synthase can reverse direction to rotate counterclockwise, hydrolyzing ATP to actively transport protons from the mitochondrial matrix into the intermembrane space thereby maintaining a proton gradient across the inner mitochondrial membrane, preventing depolarization. As a result of ATP hydrolysis by CV, less ATP will be available for other cellular processes and the prevention of depolarization will also block mitophagy.

Some embodiments herein provide for methods for treating a disease or condition in a subject in need thereof comprising stimulating mitophagy in the subject by administering to the subject a mitophagy-stimulating amount of a MAS receptor agonist or substance that triggers endogenous production of a MAS receptor agonist; wherein the MAS receptor agonist is a compound of formula (III).

Some embodiments herein provide for methods for treating a disease or condition in a subject in need thereof comprising stimulating mitophagy in the subject by administering to the subject a mitophagy-stimulating amount of a MAS receptor agonist or substance that triggers endogenous production of a MAS receptor agonist; wherein the MAS receptor agonist is selected from the group consisting of: Compound 7; Compound 10; Nle$^3$-A(1-7); and angiotensin (1-7).

Some embodiments provide for treating a disease or condition in a subject in need thereof comprising stimulating mitophagy in the subject by administering to the subject a mitophagy-stimulating amount of a MAS receptor agonist or substance that triggers endogenous production of a MAS receptor agonist, wherein the disease or condition is:

Sjorgen's syndrome, progeria, Rett Syndrome, Down Syndrome; ataxia-telangiectasia; autosomal dominant optic atrophy; Barth syndrome; Charcot-Marie-Tooth disease; Charlevoix-Saguenay spastic ataxia; Cockayne syndrome; Danon disease; Fabry disease; Fanconi anemia; Friedrich's ataxia; Fuchs endothelial dystrophy; Gaucher disease; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Pearson syndrome; Pompe disease; rhabdomyosarcoma; schizophrenia; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof.

Some embodiments provide for treating a disease or condition in a subject in need thereof comprising stimulating mitophagy in the subject by administering to the subject a mitophagy-stimulating amount of a MAS receptor agonist or substance that triggers endogenous production of a MAS receptor agonist, wherein the disease or condition is:

Sjorgen's syndrome, progeria, Rett Syndrome, Down Syndrome; ataxia-telangiectasia; autosomal dominant optic atrophy; Barth syndrome; Charcot-Marie-Tooth disease; Charlevoix-Saguenay spastic ataxia; Cockayne syndrome; Danon disease; Fabry disease; Fanconi anemia; Friedrich's ataxia; Fuchs endothelial dystrophy; Gaucher disease; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Pearson syndrome; Pompe disease; rhabdomyosarcoma; schizophrenia; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof; and wherein the MAS receptor agonist is a compound of formula (III).

Some embodiments provide for treating a disease or condition in a subject in need thereof comprising stimulating mitophagy in the subject by administering to the subject a mitophagy-stimulating amount of a MAS receptor agonist or substance that triggers endogenous production of a MAS receptor agonist, wherein the disease or condition is:

Sjorgen's syndrome, progeria, Rett Syndrome, Down Syndrome; ataxia-telangiectasia; autosomal dominant optic atrophy; Barth syndrome; Charcot-Marie-Tooth disease; Charlevoix-Saguenay spastic ataxia; Cockayne syndrome; Danon disease; Fabry disease; Fanconi anemia; Friedrich's ataxia; Fuchs endothelial dystrophy; Gaucher disease; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Pearson syndrome; Pompe disease; rhabdomyosarcoma; schizophrenia; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof; and wherein the MAS receptor agonist is selected from the group consisting of: Compound 7; Compound 10; Nle$^3$-A(1-7); and angiotensin (1-7).

Some embodiments provide for a method for treating a disease or condition in a subject in need thereof comprising administering to the subject a mitophagy-stimulating amount of a MAS receptor agonist or substance that triggers endogenous production of a MAS receptor agonist, wherein the disease or condition is:

Sjorgen's syndrome, progeria, Rett Syndrome, Down Syndrome; ataxia-telangiectasia; autosomal dominant optic atrophy; Barth syndrome; Charcot-Marie-Tooth disease; Charlevoix-Saguenay spastic ataxia; Cockayne syndrome; Danon disease; Fabry disease; Fanconi anemia; Friedrich's ataxia; Fuchs endothelial dystrophy; Gaucher disease; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodege2.2neration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Pearson syndrome; Pompe disease; rhabdomyosarcoma; schizophrenia; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof.

Some embodiments provide for a method for treating a disease or condition in a subject in need thereof comprising administering to the subject a mitophagy-stimulating amount of a MAS receptor agonist or substance that triggers endogenous production of a MAS receptor agonist, wherein the disease or condition is:

Sjorgen's syndrome, progeria, Rett Syndrome, Down Syndrome; ataxia-telangiectasia; autosomal dominant optic atrophy; Barth syndrome; Charcot-Marie-Tooth disease; Charlevoix-Saguenay spastic ataxia; Cockayne syndrome; Danon disease; Fabry disease; Fanconi anemia; Friedrich's ataxia; Fuchs endothelial dystrophy; Gaucher disease; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodege2.2neration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Pearson syndrome; Pompe disease; rhabdomyosarcoma; schizophrenia; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof; and wherein the MAS receptor agonist is a compound of formula (III).

Some embodiments provide for a method for treating a disease or condition in a subject in need thereof comprising administering to the subject a mitophagy-stimulating amount of a MAS receptor agonist or substance that triggers endogenous production of a MAS receptor agonist, wherein the disease or condition is:

Sjorgen's syndrome, progeria, Rett Syndrome, Down Syndrome; ataxia-telangiectasia; autosomal dominant optic atrophy; Barth syndrome; Charcot-Marie-Tooth disease; Charlevoix-Saguenay spastic ataxia; Cockayne syndrome; Danon disease; Fabry disease; Fanconi anemia; Friedrich's ataxia; Fuchs endothelial dystrophy; Gaucher disease; intellectual developmental disorder with short stature and variable skeletal anomalies; Kearns-Sayre syndrome; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodege2.2neration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Pearson syndrome; Pompe disease; rhabdomyosarcoma; schizophrenia; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof; and wherein the MAS receptor agonist is selected from the group consisting of: Compound 7; Compound 10; $Nle^3$-A(1-7); and angiotensin (1-7).

Some embodiments provide for a method for treating amyotrophic lateral sclerosis (ALS) in a subject in need thereof comprising stimulating mitophagy in the subject by administering to the subject a mitophagy-stimulating amount of a MAS receptor agonist or substance that triggers endogenous production of a MAS receptor agonist; wherein the subject exhibits a C9orf72 mutation, Optn (optineurin) mutation or TBK1 mutation.

Some embodiments provide for a method for treating amyotrophic lateral sclerosis (ALS) in a subject in need thereof comprising stimulating mitophagy in the subject by administering to the subject a mitophagy-stimulating amount of a MAS receptor agonist or substance that triggers endogenous production of a MAS receptor agonist; wherein the subject exhibits a C9orf72 mutation, Optn (optineurin) mutation or TBK1 mutation; and wherein the MAS receptor agonist is a compound of formula (III).

Some embodiments provide for a method for treating amyotrophic lateral sclerosis (ALS) in a subject in need thereof comprising stimulating mitophagy in the subject by administering to the subject a mitophagy-stimulating amount of a MAS receptor agonist or substance that triggers endogenous production of a MAS receptor agonist; wherein the subject exhibits a C9orf72 mutation, Optn (optineurin) mutation or TBK1 mutation; and wherein the MAS receptor agonist is selected from the group consisting of: Compound 7; Compound 10; $Nle^3$-A(1-7); and angiotensin(1-7).

Some embodiments provide for a method for treating Parkinson's Disease in a subject in need thereof comprising stimulating mitophagy in the subject by administering to the subject a mitophagy-stimulating amount of a MAS receptor agonist or substance that triggers endogenous production of a MAS receptor agonist; wherein the subject exhibits a LRRK2 mutation, GBA mutation, Pink1 mutation, or Prkn2 mutation.

Some embodiments provide for a method for treating Parkinson's Disease in a subject in need thereof comprising stimulating mitophagy in the subject by administering to the subject a mitophagy-stimulating amount of a MAS receptor agonist or substance that triggers endogenous production of a MAS receptor agonist; wherein the subject exhibits a LRRK2 mutation, GBA mutation, Pink1 mutation, or Prkn2 mutation; and wherein the MAS receptor agonist is a compound of formula (III).

Some embodiments provide for a method for treating Parkinson's Disease in a subject in need thereof comprising stimulating mitophagy in the subject by administering to the subject a mitophagy-stimulating amount of a MAS receptor agonist or substance that triggers endogenous production of a MAS receptor agonist; wherein the subject exhibits a LRRK2 mutation, GBA mutation, Pink1 mutation, or Prkn2 mutation; and wherein the MAS receptor agonist is selected from the group consisting of: Compound 7; Compound 10; Nle$^3$-A(1-7); and angiotensin(1-7).

Some embodiments provide for a method for treating a disease or condition in a subject in need thereof comprising:
  stimulating mitophagy in the subject by
    administering to the subject a mitophagy-stimulating amount of a MAS receptor agonist or substance that triggers endogenous production of a MAS receptor agonist, and
    administering to the subject an effective amount of an agent that stimulates mitochondrial biogenesis;
    wherein the disease or condition is Alzheimer's disease; amyotrophic lateral sclerosis (ALS); cardiovascular disease; frontotemporal dementia; hematopoietic disorders; Parkinson's disease; primary biliary cirrhosis/cholangitis (PBC); sepsis; renal injury/damage, hypertension, cancer, or any combination thereof.

In some embodiments, the disease or condition is Alzheimer's disease. In some embodiments, the disease or condition is ALS. In some embodiments, the disease or condition is hypertension. In some embodiments, the disease or condition is cancer. In some embodiments, the cancer is a bone cancer. In some embodiments, the cancer is osteosarcoma.

Some embodiments further comprises administering to the subject an effective amount of an additional therapeutic agent. In some embodiments, the additional therapeutic agent is urolithin A.

Some embodiments further comprise administering to the subject an effective amount of an agent that stimulates mitochondrial biogenesis. Non-limiting examples of an agent that stimulates mitochondrial biogenesis are AMPK activators (such as AICAR); SIRT1 activators (such as resveratrol, SRT1720, SRT1460, SRT2104, and SRT2379); β2-adrenergic agonists (such as formoterol); 5HT agonists (such as LY344,864 and DOI); CB1 agonists (such as rimonabant); PPARα agonists (such as fibrates and thiazolidinediones); PPARγ agonists (such as GW501516); glucocorticoid agonists (such as dexamethasone); PDE inhibitors (such as sildenafil or vardenafil); nitric oxide mimetics (DETA-NO); GC activators (such as BAY-41-2272, cinaciguat, and riociguat); natriuetic peptides (ANP or BNP); natural products (such as green tea polyphenols, lipoamide, isoflavones, quercetin); and genetic modulators (such as recombinant TFAM or donor mtDNA).

Some embodiments provide for methods for treating a disease or condition in a subject in need thereof comprising stimulating mitophagy in the subject by administering to the subject a mitophagy-stimulating amount of a MAS receptor agonist or substance that triggers endogenous production of a MAS receptor agonist,
  wherein the disease or condition is: Alzheimer's disease; amyotrophic lateral sclerosis (ALS); cardiovascular disease; frontotemporal dementia; hematopoietic disorders; Parkinson's disease; primary biliary cirrhosis/cholangitis (PBC); sepsis; renal injury/damage, hypertension, cancer, or any combination thereof; and
  wherein the subject exhibits, prior to administration of the MAS receptor agonist or substance that triggers endogenous production of a MAS receptor agonist, one or more of the following:
    increased lactate levels; impaired phosphocreatine recovery; decreased mitochondrial respiratory complex protein and activity levels; down-regulated mitochondrial genes; increased plasma acylcarnitines levels; increased mitochondrial DNA (mtDNA) deletion mutation frequency; increased levels of creatine; increased levels of fibroblast growth factor 21 (FGF21); increased levels of growth/differentiation factor 15 (GDF-15); increased levels of cell free circulating-mtDNA (ccf-mtDNA); increased levels of neurofilament light-chain (NF-L); increased levels of depolarized mitochondria or mitochondria with oxidized content, damaged content, or disturbed structure; increased heterogenity in mitochondria; or increased levels of mtDNA released in cytosol or plasma.

Also provided herein are methods to treat a disease or condition caused by a dysfunctional macrophage, monocyte, microglial cell, or neutrophil in a subject in need thereof, comprising stimulating mitophagy in the subject by administering to the subject a mitophagy-stimulating amount of a MAS receptor agonist or substance that triggers endogenous production of a MAS receptor agonist. Non-limiting examples of a disease or condition caused by a dysfunctional macrophage, monocyte, microglial cell, or neutrophil may be a disease or condition caused by senescent and exhausted macrophages, monocytes and microglial cells having limited phagocytic activities and antigen presentation capabilities.

EXAMPLES

Methods

The following examples are put forth so as to provide persons having ordinary skill in the art with a complete disclosure and description of how to make and use the subject disclosure, and are not intended to limit the scope of what the inventor regards as the disclosure. Efforts have been made to ensure accuracy with respect to the numbers used (e.g., quantities, amounts, temperature, concentrations, etc.) but some experimental errors and deviations should be allowed for. Unless otherwise indicated, parts are parts by weight, molecular weight is average molecular weight, temperature is in degrees Celsius; and pressure is at or near atmospheric pressure.

The following methods were used for studies described herein conducted with the INS1 cell line or the U2OS cell line. Data described in Examples 1-5 were achieved in INS1 cell line unless otherwise noted.

Viral Transduction

Cells were seeded and culture in pre-placed coverslips in a 24-well plate. No need to coat the coverslips. Cells were transduced with 1 ml of working stock of mCherry-GFP-Fis1101-152 adenovirus. The working stock was prepared first by diluting 1 µl of stock mCherry-GFP-Fis1101-152 virus (1×10$^{12}$ vp/mL; Welgen™) into 500 µl of 5 mM RPMI solution ("Roswell Park Memorial Institute" solution) (solution A) then further diluted by transferring 0.75 µl/well of solution A into 24 ml of 5 mM RPMI. Viral incubation was performed for 24 hrs at 37° C. in a 5% CO$_2$ incubator. After 24 hours, treatments were performed. Different compounds were treated for 8 h, 24 h and 72 h. When treatments were completed cells were fixed with pre-warmed 4% paraformaldehyde (PFA). PFA was removed by 2 washes of PBS-0.2% TWEEN® solution.

Imaging Apparatus

All imaging was performed on Zeiss™ LSM880. Super-resolution imaging was performed with 63× Apochromat oil-immersion lens and AiryScan™ super-resolution detector (Huff et al., 2015). All fluorophores were excited on separate tracks to avoid artifacts due to bleed-through emission. GFP and MitoTrackerGreen™ was excited with 488 nm, 25 mW Argon-ion laser, and their emission captured through 500-550 nm band-pass filter. mCherry was excited with 543 nm, 1 mW Helium-Neon laser, or 561 nm, 20 mW diode-pumped solid-state laser and their emission captured through a 580-650 nm band-pass filter.

Image Analysis of MitoQC

All image analysis was performed in the CellProfiler™ software (cellprofiler.org) to distinguish mitochondrial structures for morphological characteristics and mitophagic events. Individual mitochondrial fluorescence intensity and area were measured in CellProfiler™ and imported into Microsoft Excel®. Mitochondria smaller than 2 pixels in area were not included in final analyses. Images were subjected to top hat filtering followed by global threshold Otsu method to segment mitochondria. This was performed on both red and green channels.

Mitochondrial Respirometry

Respirometry of INS1 and U2OS cells were performed using the Seahorse Bioscience™ XF96 platform (Agilent Technologies, Santa Clara, CA) as previously described (Ferrick et al., 2008). The oxygen consumption of the R cells in each well is measured by oxygen concentration changes versus time. And mitochondrial glycolysis was measured as a readout of extracellular acidification rate (ECAR), measured by the changes to pH versus time. INS1 cells were seeded in 22,000 cells/well of 120 L/well of 5 mM RPMI a XF96 microplate and allowed to seed overnight before treatments were performed 24 hours later. After 2 days, respirometry was performed using the Seahorse™ XF 96.

Prior to the assay, INS1 or U2OS cells were incubated for 1 hour in 150-185 μL/well Seahorse™ assay media (XF Base Media Minimal DMEM, pH 7.4, supplemented with 2 mmol/L glucose, 1 mM sodium pyruvate, and 2 mM 1-glutamine) at 37° C. For port injections, nutrients/compounds were injected as such, Oligomycin (final concentration 3 mol/L) in port A, carbonyl cyanide p-trifluoromethoxyphenylhydrazone (FCCP) diluted in a mixture of 80% sodium pyruvate and 20% of 1:1 L-leucine/L-glutamine (final concentration 1.27 mol/L FCCP in 11.4 mmol/L sodium pyruvate and 2.9 mmol/L each of leucine/glutamine) in port B, and rotenone and antimycin A (final concentration 2.5 mol/L) in port C. When the Seahorse™ run is complete, oxygen consumption rate (OCR) and extracellular acidification rate (ECAR) were exported from the Agilent Wave™ software and normalized by cell count in Microsoft Excel®.

Cells were imaged after Seahorse™ experiments using an Operetta high-throughput imaging device (PerkinElmer) in brightfield mode with 2× or 10× objectives.

Mitochondrial Content

Cells were cultured on coverslips inside a Petri dish filled with the appropriate culture medium or grown directly into a four-chamber glass bottom dish and cells were subsequently imaged on the LSM880. At least 30 cells per condition per experiment were collected, at least three separate experiments were performed for imaging clonal cells. Image analysis was performed in the CellProfiler™ software (cellprofiler.org) to measure mitophagic events. Individual mitochondrial fluorescence intensity and area were measured in CellProfiler™ and imported into Microsoft Excel®. Mitochondria smaller than 2 pixels in area were not included in final analyses. Images were subjected to top hat filtering followed by global threshold Otsu method to segment mitochondria. To assess amount of mitochondrial content, green fluorescence intensity of objects identified as mitochondrial structures were quantitated. Data has been normalized to the control treatment, dimethyl sulfoxide (DMSO).

Morphology

All image analysis was performed in the CellProfiler software (cellprofiler.org) to distinguish mitochondrial structures for mitophagic events. Individual mitochondrial fluorescence intensity and area were measured in CellProfiler and imported into Microsoft Excel®. Mitochondria smaller than 2 pixels in area were not included in final analyses. Images were subjected to top hat filtering followed by global threshold OTSU method to segment mitochondria. This was performed on both red and green channels. Length was calculated using the major axes of the ellipse equivalent to the mitochondria (long axis over short axis) and form factor measured the degree of branching (FF; perimeter2/ $4\pi$*area).

Mitophagy

INS1 cells were seeded into four compartment CELL-VIEW™ glass bottom cell culture dishes at a density of $2\times10^4$ cells/compartment. After 48 h cells were transduced with an adenoviral construct encoding the fluorescent mitophagy reporter mCherry-GFP-Fis1101-152 for 24 h. A media change containing the indicated treatment concentration or 0.1% DMSO as vehicle control was performed 8 h before the imaging session. Imaging was performed using a 63× Plan Neofluar objective and the Airyscan module of a Zeiss™ LSM880 confocal microscope. Twenty-five visual fields containing 59-85 cells in total were imaged per condition. The experiment was repeated three times independently. Image analysis was performed with FIJI ImageJ 1.51p and CellProfiler 2.2.0 rev ac0529e. Briefly, individual cells were cropped and the background was subtracted using a median filter assisted processing method. Ratios of red/green fluorescence channels were computed and mitophagy positive structures were recognized based on a lower ratio cut-off of 2.5 of red over green. Mitophagy events per cell were determined by the following formula: Mitophagy events per cell ¼ Total area of mitophagy positive structures per cell Average area of one mitophagy structure. Data were normalized to DMSO controls to account for day-to-day variation. Statistical analysis was performed using GraphPad Prism™ 7.02. Significant treatment differences were determined using One-way ANOVA and Tukey post-hoc analysis. Values of $P<0.05$ (*) were considered significant.

Fibroblasts

Control and patient skin derived fibroblasts were fixed (4% paraformaldehyde in Phosphate-buffered Saline—PBS), permeabilized (0.1% Triton X-100 in PBS) and stained with anti-LC3, anti-TOMM20 and secondary antibodies (Invitrogen) in blocking solution (5% goat serum). Confocal image acquisition of 3D Z-stacks was performed using a Zeiss™ LSM880 with Airyscan equipped with a Zeiss™ Pla-Apochromat 40×/1.2 objective. Quantification of mitophagosomes (LC3+TOMM20 co-localization) was performed using Aivia™ v.10 software (Leica™ Microsystem). Both channels were used to create a confidence map with pixel classification machine learning technique. 3D co-localization was performed and LC3 vesicles were counted. Graph shows % of co-localized LC3 vesicles with TOMM20 from total LC3 count. Approximately 50 cells from each condition were acquired and analyzed randomly. One-way ANOVA with Dunnett's multiple comparisons was used for statistics between control and patients cell lines.

Example 1. Compounds Stimulate Mitophagy

Figure 6A:
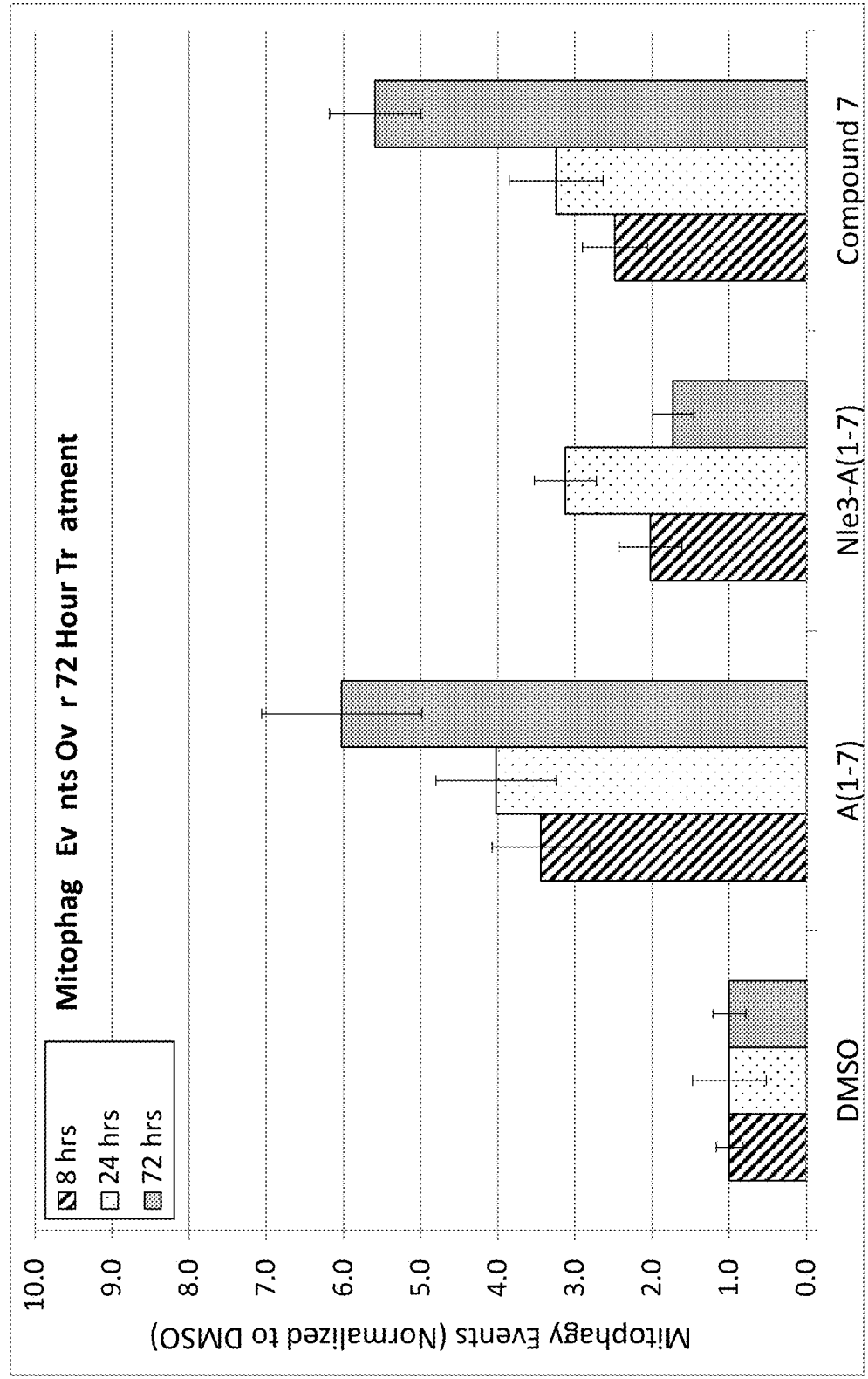
FIG. 6A depicts rate of mitophagy after three durations of treatment with various test compounds, including dimethyl sulfoxide (DMSO) negative control and 50 nM of angiotensin(1-7), $Nle^3$-A(1-7), and Compound 7.

FIG. 6A depicts the rate of mitophagy after three durations of treatment with various test compounds, including 50 nM of DMSO negative control, angiotensin(1-7), Nle$^3$-A(1-7), and Compound 7.

Figure 6B:
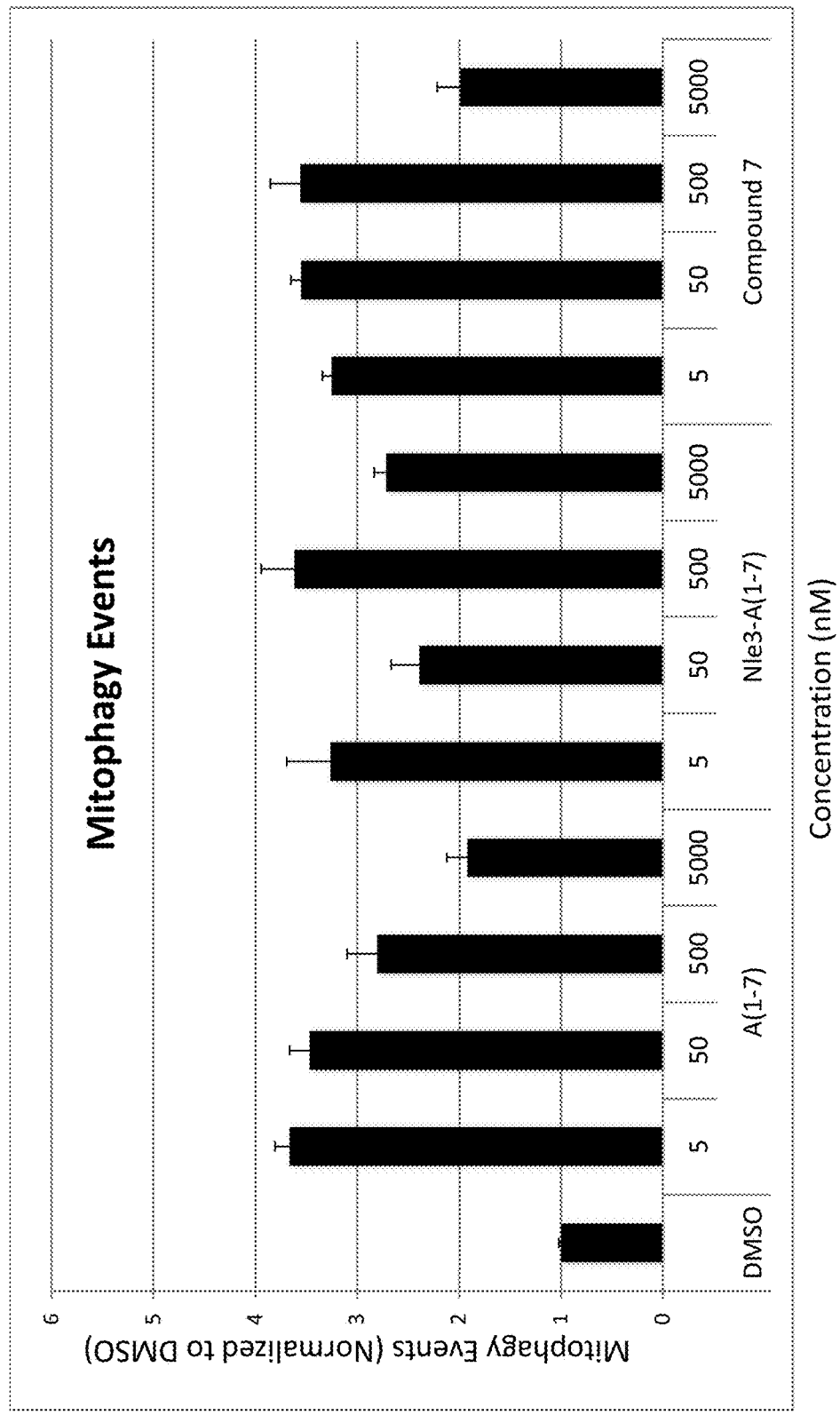
FIG. 6B depicts rate of mitophagy after 8 hours treatment with four different dose levels of DMSO negative control and MAS receptor agonists angiotensin(1-7), $Nle^3$-A(1-7), and Compound 7.

FIG. 6B depicts rate of mitophagy after 8 hours treatment with DMSO negative control and four different doses of MAS receptor agonists angiotensin(1-7), Nle$^3$-A(1-7), and Compound 7.

Figure 6C:
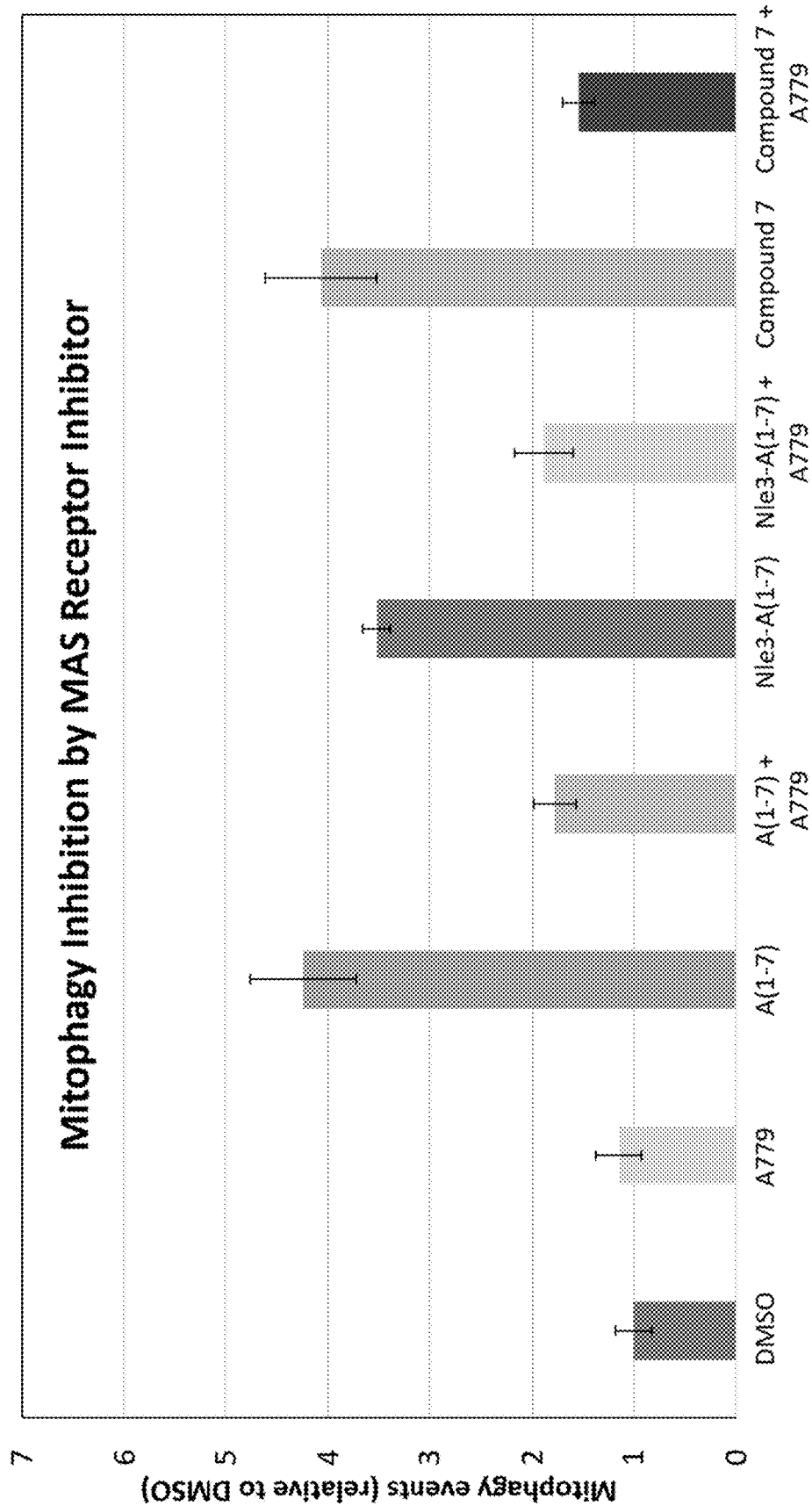
FIG. 6C depicts mitophagic responses to MAS receptor activation and MAS receptor chemical knockdown. Cells were treated with DMSO negative control; 1 M MAS receptor inhibitor (antagonist) A779; angiotensin(1-7); angiotensin(1-7)+A779; $Nle^3$-A(1-7); $Nle^3$-A(1-7)+A779; Compound 7; and Compound 7+A779. The results of the experiment are strong evidence that MAS receptor activity directly impacts mitochondrial turnover.

FIG. 6C depicts mitophagic responses to MAS receptor activation and MAS receptor chemical knockdown. Cells were treated DMSO negative control; 1 M MAS receptor inhibitor A779; angiotensin(1-7); angiotensin(1-7)+A779; Nle$^3$-A(1-7); Nle$^3$-A(1-7)+A779; Compound 7; and Compound 7+A779. The results of the experiment are strong evidence that MAS receptor activity directly impacts mitochondrial turnover.

Figure 14:
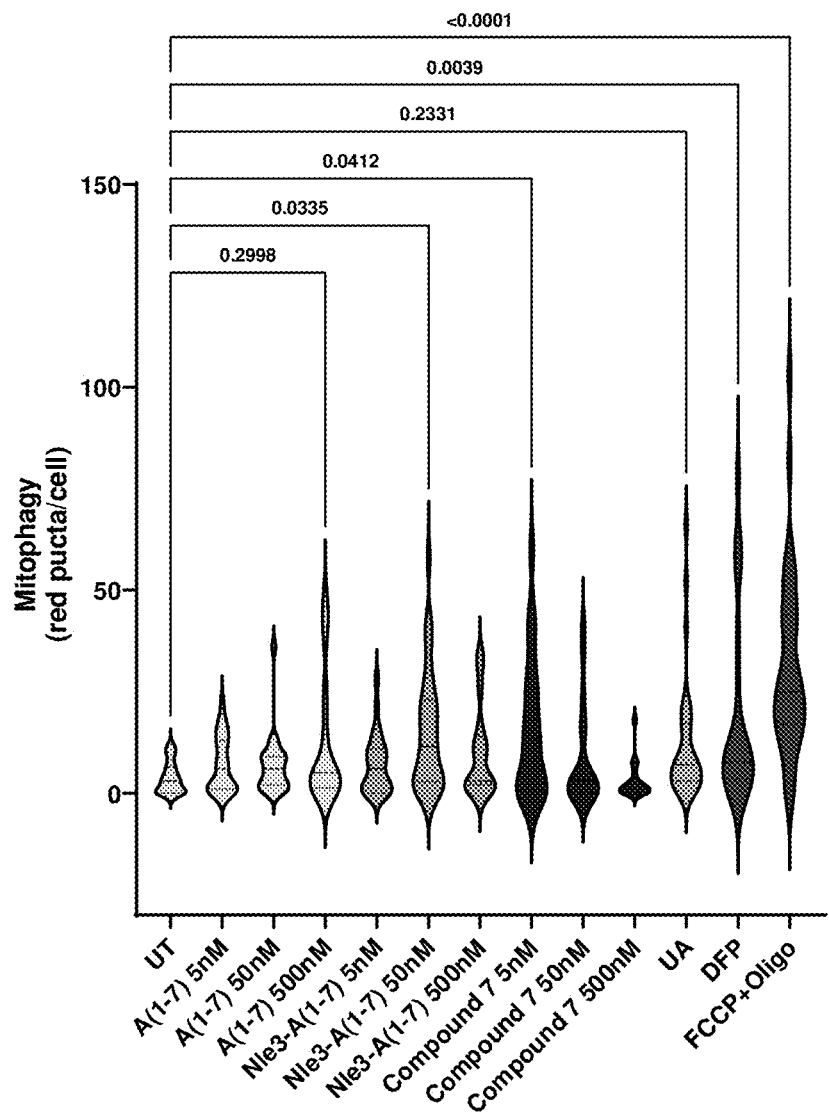
FIG. 14 demonstrates that MAS agonists tested induced mitophagy in U2-OS cells. UT=Untreated, UA=Urolithin A, DFP=deferiprone, FCCP+Oligo=Carbonyl cyanide-4 (trifluoromethoxy) phenylhydrazone+Oligomycin; and A(1-7) =angiotensin(1-7).

FIG. 14 demonstrates that MAS agonists tested induced mitophagy in U2-OS cells.

Example 2. Mitochondrial Function is Normal after Compound Treatment

Figure 7A:
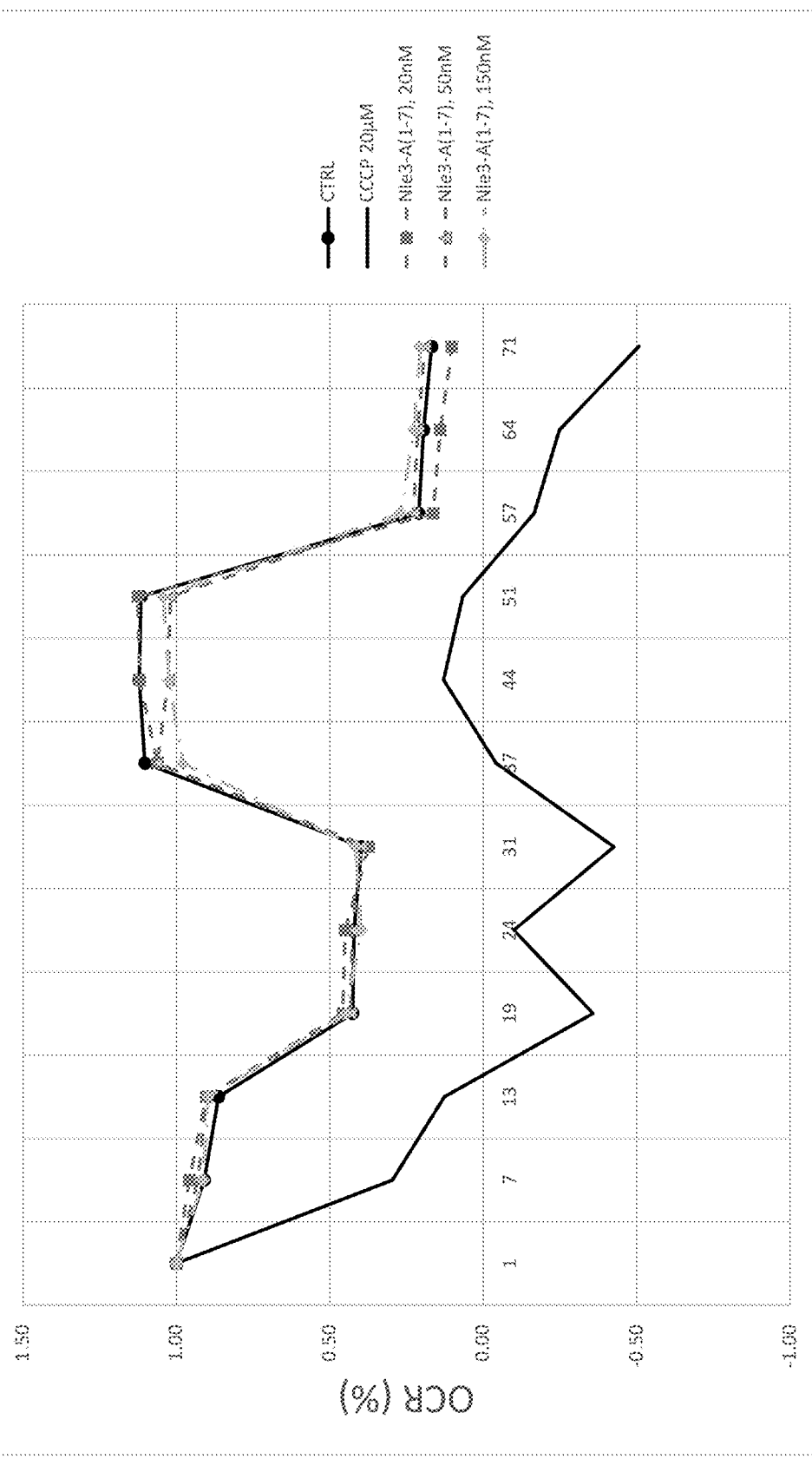
FIGS. 7A, 7B, and 7C depict the oxygen consumption rate (OCR) in cells treated with of DMSO negative control, no-mitochondrial control, and with three different concentrations of MAS receptor agonists $Nle^3$-A(1-7) (FIG. 7A), angiotensin(1-7) (FIG. 7B), and Compound 7 (FIG. 7C). CCCP is carbonyl cyanide m-chlorophenyl hydrazone, a chemical inhibitor of OXPHOS, which operates in these experiments as a negative control for mitochondrial activity.
Figure 7B:
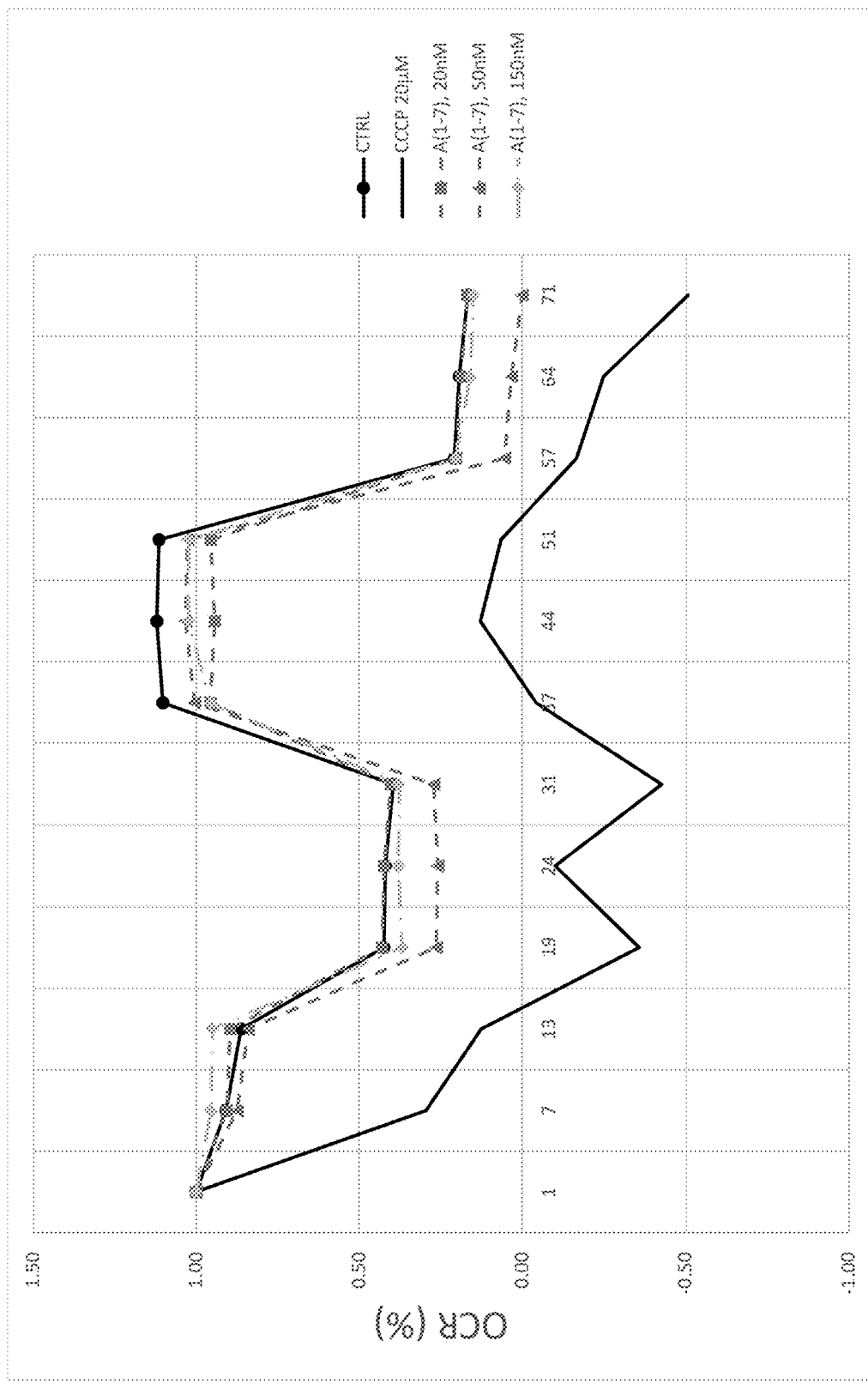
Figure 7C:
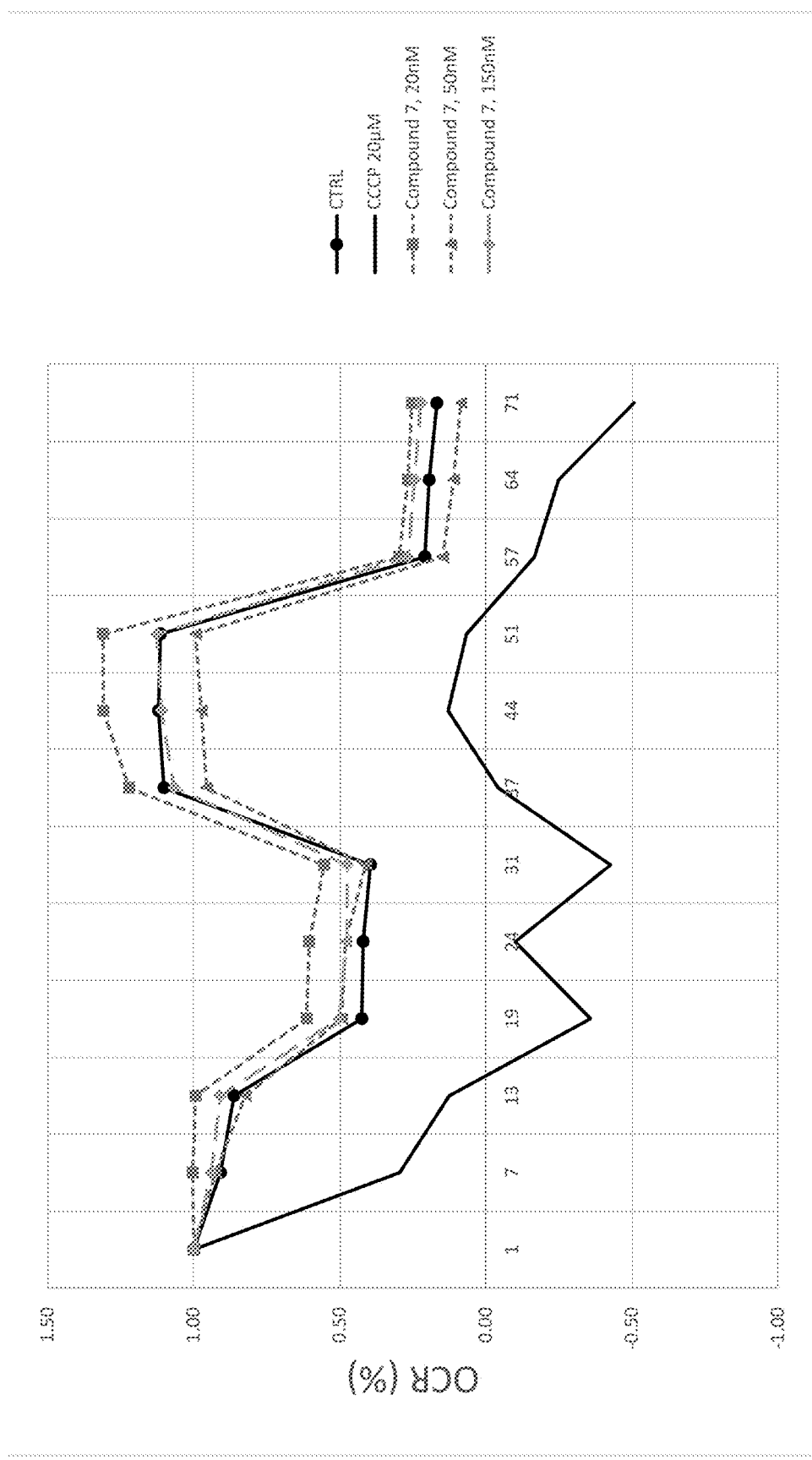

FIGS. 7A, 7B, and 7C depict the oxygen consumption rate (OCR) in cells treated with of negative control, no-mitochondrial control, and with three different concentrations of MAS receptor agonists Nle$^3$-A(1-7) (FIG. 7A), angiotensin (1-7) (FIG. 7B), and Compound 7 (FIG. 7C). CCCP is carbonyl cyanide m-chlorophenyl hydrazone, a chemical inhibitor of OXPHOS, which operates in these experiments as a negative control for mitochondrial activity.

Example 3. Extracellular Acidification Rate is Unchanged by Test Compounds

Figure 8A:
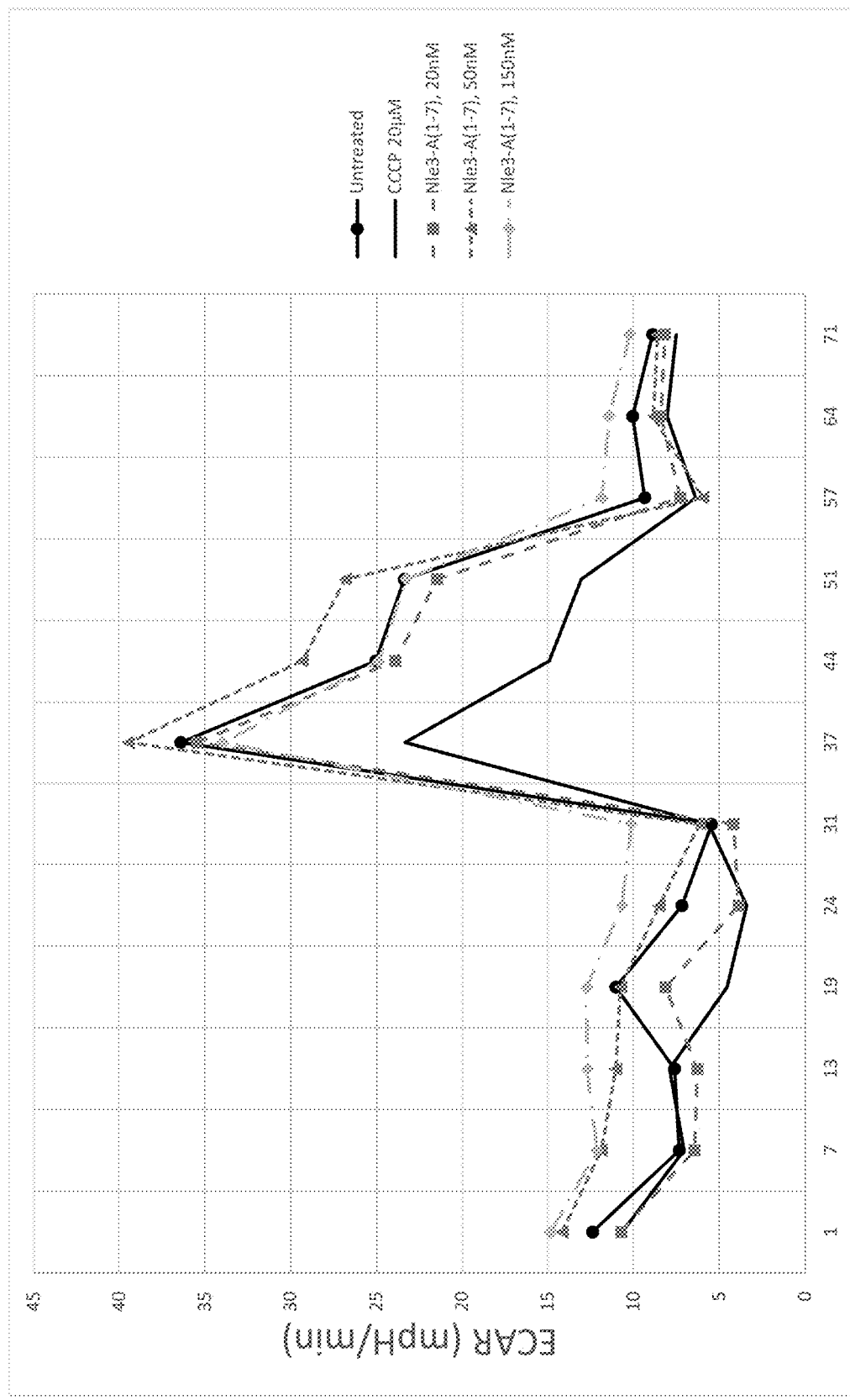
FIGS. 8A, 8B, and 8C depict the extracellular acidification rate (ECAR) in cells treated with a negative control, no-mitochondrial control, and three different concentrations of MAS receptor agonists $Nle^3$-A(1-7) (FIG. 8A), angiotensin(1-7) (FIG. 8B), and Compound 7 (FIG. 8C). CCCP operates in these experiments as a negative control for mitochondrial activity.
Figure 8B:
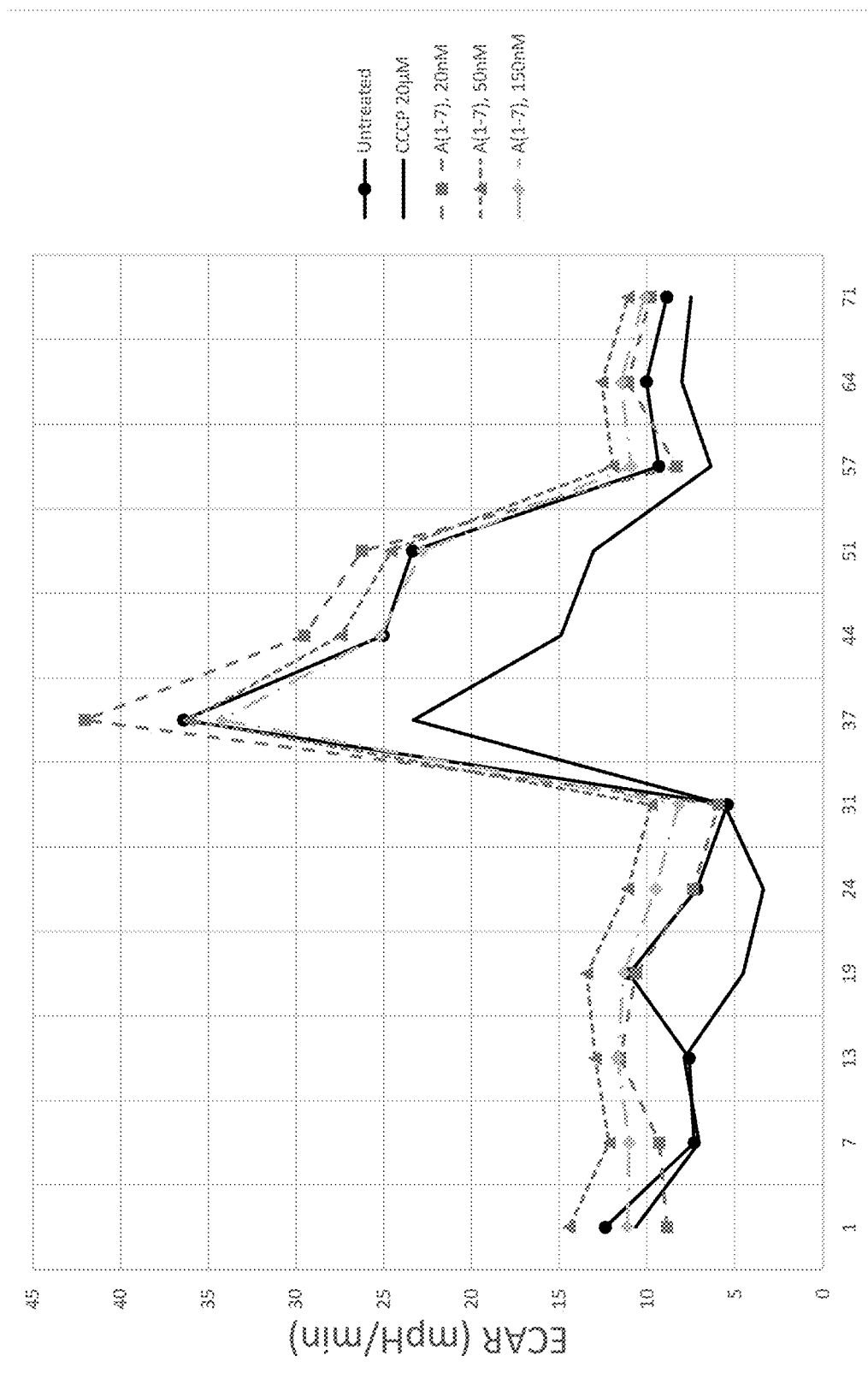
Figure 8C:
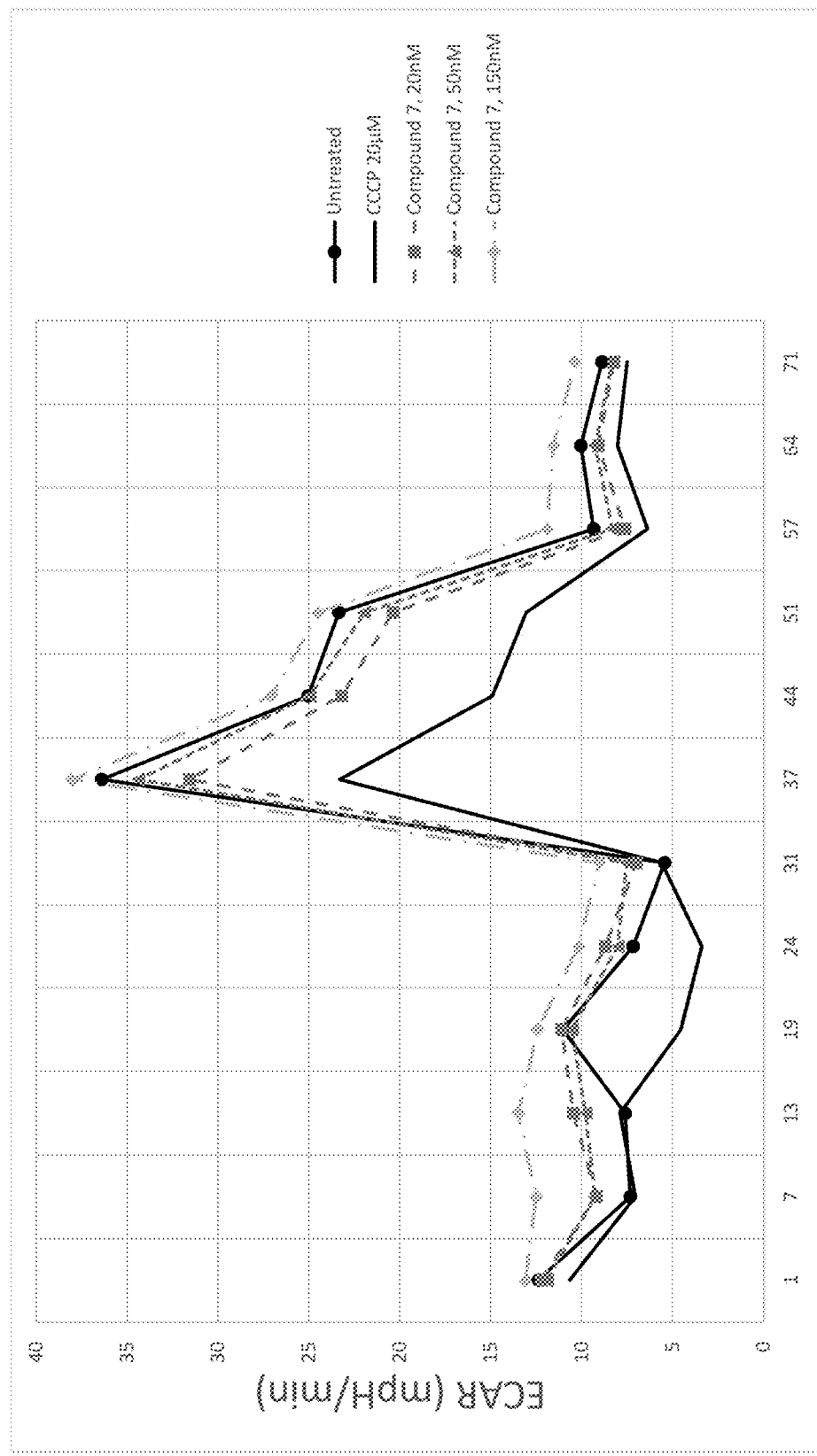

FIGS. 8A, 8B, and 8C depict the extracellular acidification rate (ECAR) in cells treated with a negative control, no-mitochondrial control, and three different concentrations of MAS receptor agonists Nle$^3$-A(1-7) (FIG. 8A), angiotensin(1-7) (FIG. 8B), and Compound 7 (FIG. 8C). CCCP operates in these experiments as a negative control for mitochondrial activity.

Example 4. Effect of Compounds on Mitochondrial Mass

Figure 9:
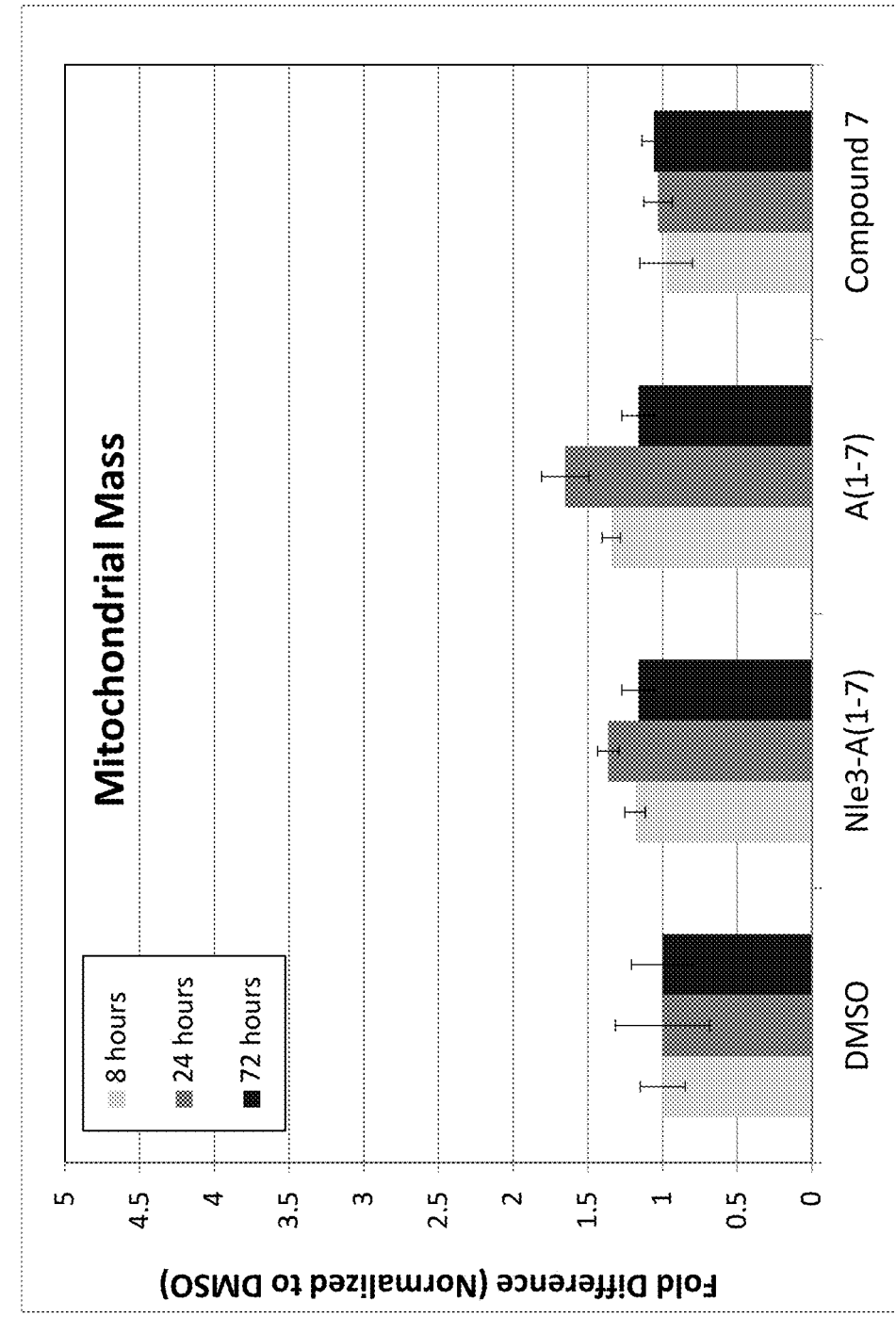
FIG. 9 depicts the cellular mitochondrial mass following test treatments of various durations, concentrations, and test compounds. Cells were treated with 8 hours, 24 hours, and 72 hours of three concentrations of DMSO negative control, $Nle^3$-A(1-7), angiotensin(1-7), and Compound 7. The stable cellular mitochondrial content is strong evidence that mitophaged mitochondria are being replaced by new mitochondria via biogenesis.
Figure 10A:
FIGS. 10A, 10B, 10C, 10D, 10E, 10F, 10G, 10H, 10I, 10J, 10K, 10L, and 10M depict super-resolution micrographs following treatment with DMSO negative control, and with 5 nM, 50 nM, 500 nM, and 5 M concentrations respectively of angiotensin(1-7), $Nle^3$-A(1-7), and Compound 7 respectively.
Figure 10B:
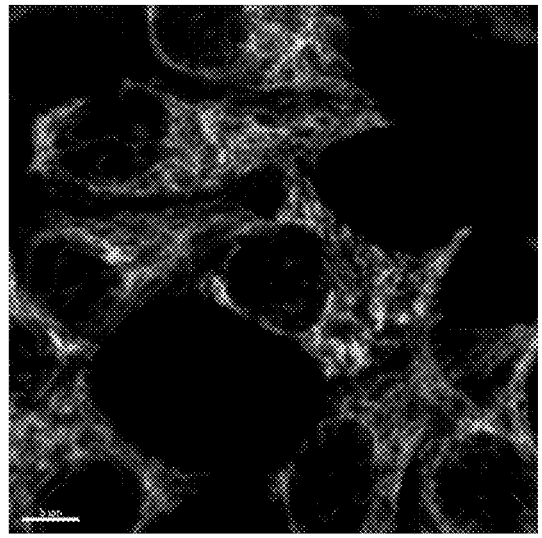
Figure 10C:
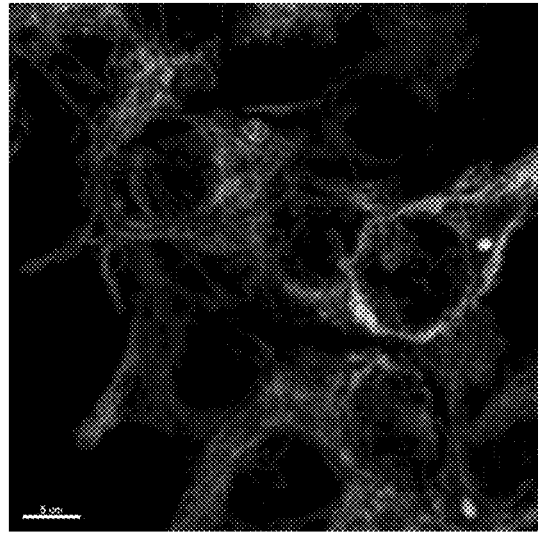
Figure 10D:
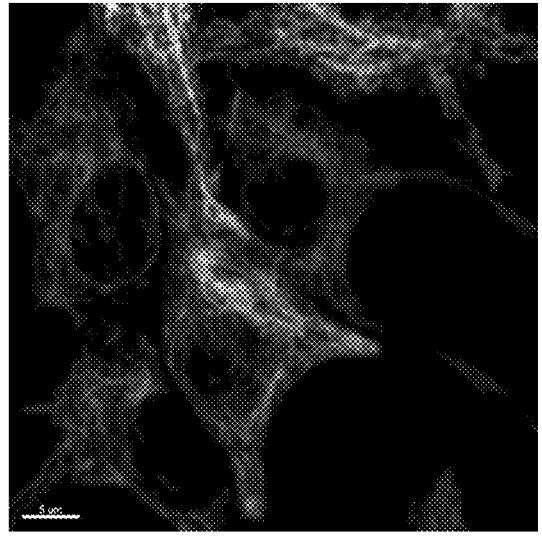
Figure 10E:
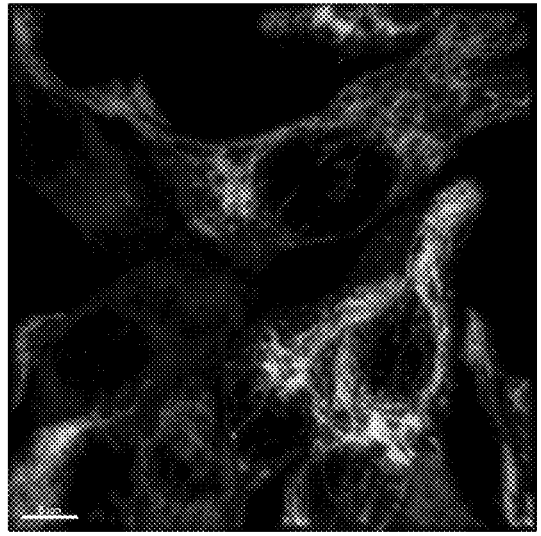
Figure 10F:
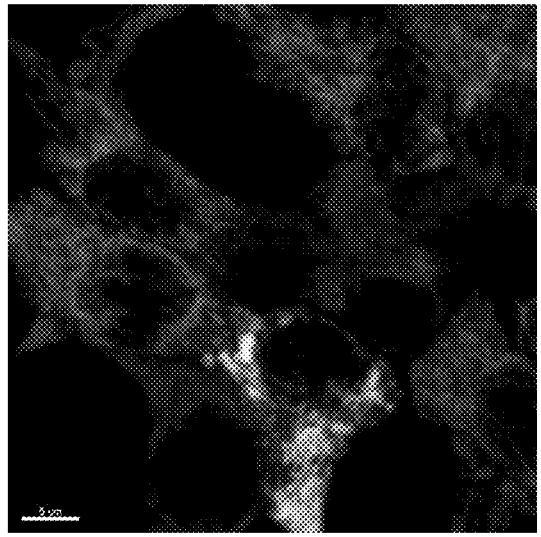
Figure 10G:
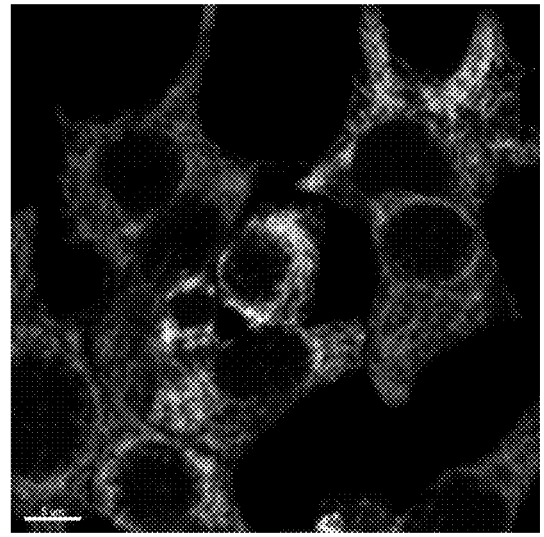
Figure 10H:
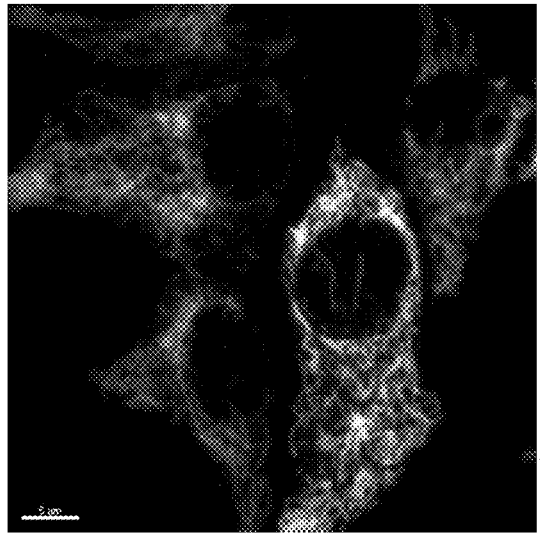
Figure 10I:
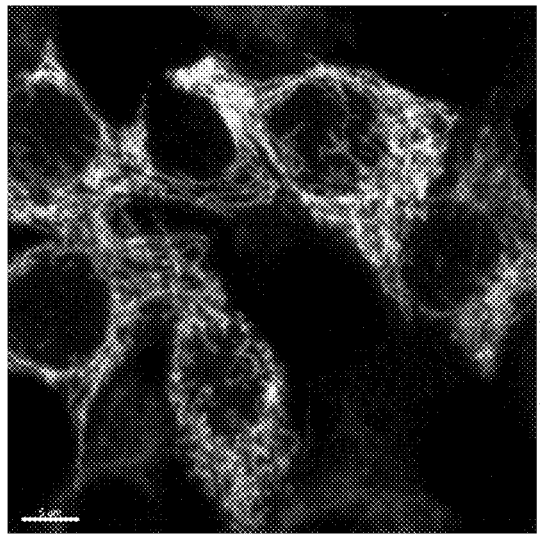
Figure 10J:
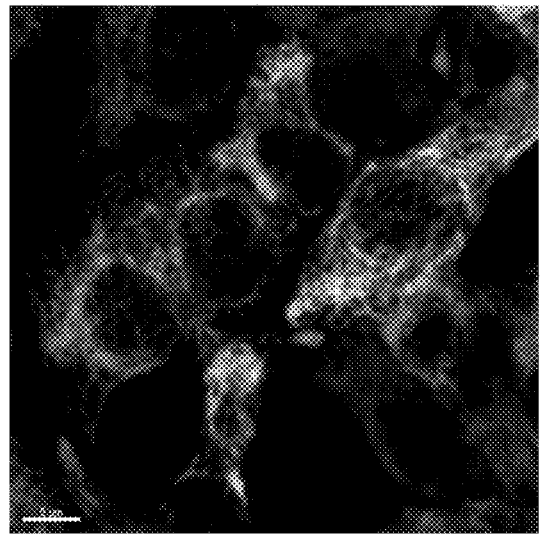
Figure 10K:
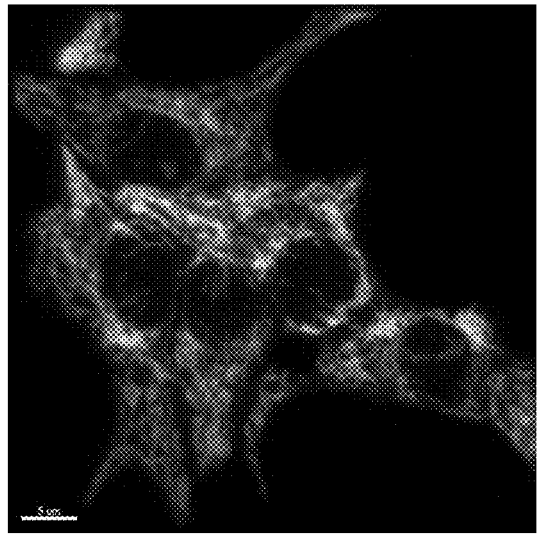
Figure 10L:
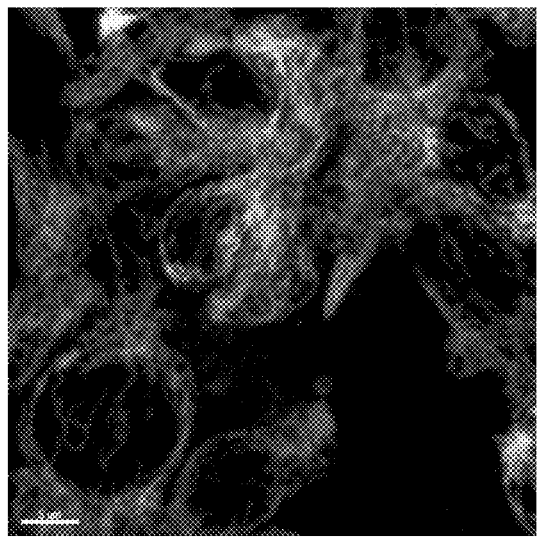
Figure 10M:
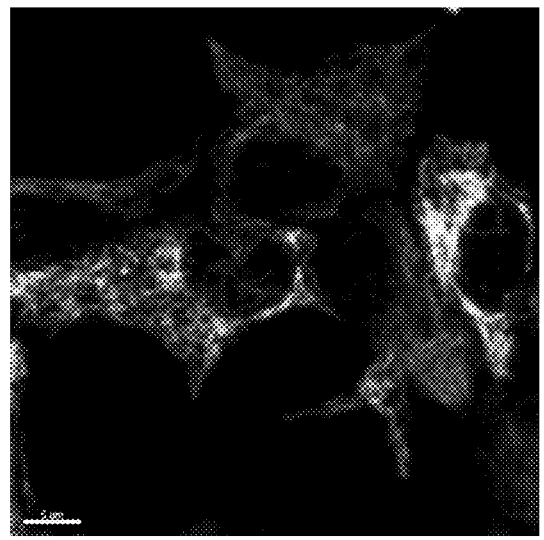

FIG. 9 depicts the cellular mitochondrial mass following test treatments of various durations, concentrations, and test compounds. Cells were treated with 8 hours, 24 hours, and 72 hours of three concentrations of DMSO negative control, Nle$^3$-A(1-7), angiotensin(1-7), and Compound 7. The stable cellular mitochondrial content is strong evidence that mitophaged mitochondria are being replaced by new mitochondria via biogenesis.

Example 5. Morphology of Mitochondria After Compound Treatment

FIGS. 10A, 10B, 10C, 10D, 10E, 10F, 10G, 10H, 10I, 10J, 10K, 10L, and 10M depict super-resolution micrographs cells following treatment with DMSO negative control, and with 5 nM, 50 nM, 500 nM, and 5 M concentrations respectively of angiotensin(1-7), Nle$^3$-A(1-7), and Compound 7 respectively.

FIGS. 11A, 11B, 11C, 11D, 11E, 11F, 11G, and 11H depict super-resolution micrographs cells following treatment with DMSO negative control; A779 (MAS receptor inhibitor); angiotensin(1-7); angiotensin(1-7)+A779; Nle$^3$-A(1-7); Nle$^3$-A(1-7)+A779; Compound 7; and Compound 7+A779.

FIG. 12 depicts a table briefly describing the morphology of cellular mitochondria in cells following 8 hours, 24 hours, and 72 hours treatment with angiotensin(1-7), Nle$^3$-A(1-7), or Compound 7.

A decrease in connectivity and formation of short, or round mitochondria occurs under conditions that conpromise mitochondiial function, such as mtDNA depletion, or treatment with mitochondrial toxins. These shifts from highly elongated and branched to fragmented norphologies. Treatment with the MAS agonists does not induce changes to mitochondrial morphology associated with mitochondrial stress such as global fragmentation at the doses tested.

Example 6: Fibroblast studies

Figure 13:
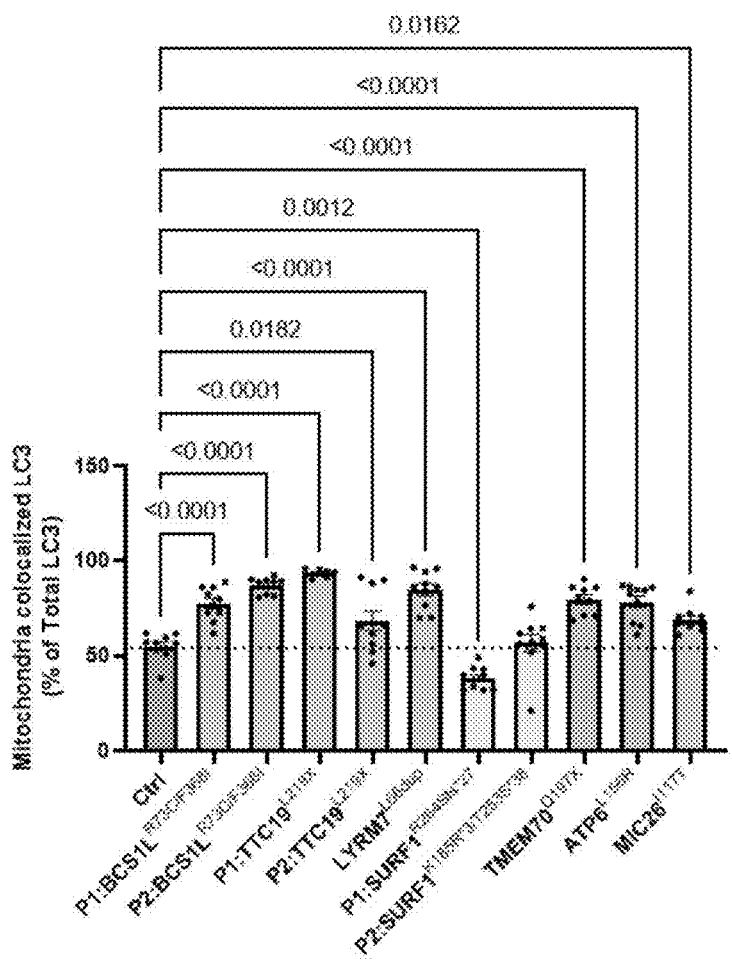
FIG. 13 shows mitochondria colocalized LC3 in certain cell lines as indicated.

Mitochondrial genetic mutations leading to defects in mitophagy in certain diseases were identified as summarized in the following table (see also FIG. 13). It is contemplated, in such diseases, stimulating mitophagy (e.g., via administration of a MAS agonist) could treat patients suffering from such diseases.

| Disease | Gene | Mutation |
| --- | --- | --- |
| LHON, Leigh Syndrome, NARP (CV Deficiency) | MTATP6 | L156R |
| CV Deficiency | TMEM70 | Q197X |
| Mitochondrial miopathy (MICOS deficiency) | MIC26 | I117T |
| Leigh Syndrome (CIII Deficiency) | TTC19 | L219X |
| GRACILE and Bjornstad Syndrome (CIII Deficiency) | BCS1L | R73C + F368I |
| GRACILE and Bjornstad Syndrome (CIII Deficiency) | BCS1L | R183C + R184C |
| CI Deficiency | NDUFA6 | A178P/c.420 + 784C > T |
| CIII Deficiency | LYRM7 | L66dup |
| Charcot-Marie-Tooth, Leigh Syndrome (CIV Deficiency) | SURF1 | R264fs |
| Charcot-Marie-Tooth, Leigh Syndrome (CIV Deficiency) | SURF1 | L185R * fs/T253S * fs |

What is claimed is:

1. A method for treating a disease or condition in a subject in need thereof comprising administering to the subject a mitophagy-stimulating amount of a MAS receptor agonist, wherein the disease or condition is:
progeria; Down Syndrome; ataxia-telangiectasia; autosomal dominant optic atrophy; Barth syndrome; Charcot-Marie-Tooth disease; Charlevoix-Saguenay spastic ataxia; Cockayne syndrome; Danon disease; Fabry disease; Friedrich's ataxia; Fuchs endothelial dystrophy; Gaucher disease; intellectual developmental disorder with short stature and variable skeletal anomalies; Krabbe disease; lactic acidosis; Lafora disease; Leber's hereditary optic neuropathy (LHON); Leigh syndrome; mental retardation, X-linked, syndromic, Turner type (MRXST); maternally inherited diabetes and deafness syndrome (MIDD); microcephaly 18 (MCPH18); microphthalmia syndromic 7; mitochondrial DNA depletion syndromes (MDDS); mitochondrial encephalopathy, lactic acidosis, and stroke-like episodes (MELAS); mitochondrial neurogastrointestinal encephalomyopathy (MNGIE); mitochondrial recessive ataxia syndrome (MIRAS); mtDNA heteroplasmy; methylmalonic acidemia (MMA); mucolipidosis II (ML II); multiple sulfatase deficiency; neurodegeneration with ataxia, dystonia, and gaze palsy (NADGP); myoclonus epilepsy with ragged red fibers (MERRF); neurodegeneration with brain iron accumulation 5 (NBIA5); neurodevelopment disorder with spastic quadriplegia and brain abnormalities with or without seizures (NEDSBAS); neuronal ceroid lipofuscinosis; Niemann-Pick disease; neuropathy, ataxia, and retinitis pigmentosa (NARP); Pearson syndrome; Pompe disease; rhabdomyosarcoma; spastic paraplegia type 15; spastic paraplegia type 49; spinocerebellar ataxia 4 (SCA4); spinocerebellar ataxia 25 (SCA25); Vici syndrome; Werner syndrome; Wolfram syndrome; xeroderma pigmentosum (XP) group A; Zellweger syndrome; or any combination thereof; and wherein the MAS receptor agonist is Compound 7, having the formula:

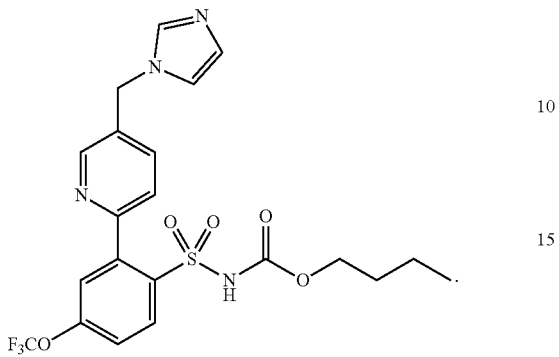

2. The method of claim 1, further comprising administering to the subject an effective amount of an agent that stimulates mitochondrial biogenesis.

3. The method of claim 1, wherein the subject is a human patient.

4. The method of claim 1, wherein the MAS receptor agonist is administered as a pharmaceutical composition.

* * * * *